United States Patent
Guyer et al.

(10) Patent No.: US 8,425,602 B2
(45) Date of Patent: Apr. 23, 2013

(54) CURVILINEAR SPINAL ACCESS METHOD AND DEVICE

(75) Inventors: Jeffrey Guyer, San Diego, CA (US); Thomas Purcell, Del Mar, CA (US); Jens Peter Timm, Carlsbad, CA (US); Ali Araghi, Phoenix, AZ (US); Javier Garcia-Bengochea, Jacksonville, FL (US); Carl Lauryssen, Beverly Hills, CA (US); Morgan Lorio, Bristol, TN (US)

(73) Assignee: Alphatec Spine, Inc., Carlsbad, CA (US)

( * ) Notice: Subject to any disclaimer, the term of this patent is extended or adjusted under 35 U.S.C. 154(b) by 724 days.

(21) Appl. No.: 12/460,795

(22) Filed: Jul. 23, 2009

(65) Prior Publication Data
US 2010/0076502 A1 Mar. 25, 2010

Related U.S. Application Data

(63) Continuation-in-part of application No. 12/069,721, filed on Feb. 11, 2008, now Pat. No. 8,152,714.

(60) Provisional application No. 60/900,554, filed on Feb. 9, 2007, provisional application No. 61/135,829, filed on Jul. 23, 2008, provisional application No. 61/195,848, filed on Oct. 10, 2008, provisional application No. 61/175,460, filed on May 5, 2009, provisional application No. 61/192,210, filed on Sep. 16, 2008.

(51) Int. Cl.
A61F 2/44 (2006.01)
A61B 17/56 (2006.01)

(52) U.S. Cl.
USPC .............. 623/17.11; 606/86 A; 606/99

(58) Field of Classification Search ............... 606/86 A, 606/99; 600/114, 184
See application file for complete search history.

(56) References Cited

U.S. PATENT DOCUMENTS

| | | | | |
|---|---|---|---|---|
| 4,877,016 | A * | 10/1989 | Kantor et al. | 600/109 |
| 4,982,729 | A * | 1/1991 | Wu | 600/187 |
| 2004/0117019 | A1* | 6/2004 | Trieu et al. | 623/17.11 |
| 2006/0247655 | A1* | 11/2006 | Francis et al. | 606/99 |
| 2008/0097154 | A1* | 4/2008 | Makower et al. | 600/114 |

FOREIGN PATENT DOCUMENTS
WO WO2006/041963 5/2006

* cited by examiner

*Primary Examiner* — Nicholas Woodall
(74) *Attorney, Agent, or Firm* — Michael J. Loi

(57) ABSTRACT

A curvilinear spinal access device having an expandable working portal. The device includes a slide having a channel with an open top and a movable top sized to cover the open top of the channel forming an expandable working portal with a proximal end and a distal end. The movable top can be moved between a closed position and an open position, wherein in the closed position the movable top blocks direct visualization between the proximal end and the distal end of the expandable working portal and in the open position movement of the movable top results in direct visualization from the proximal end to the distal end of the expandable working portal.

22 Claims, 61 Drawing Sheets

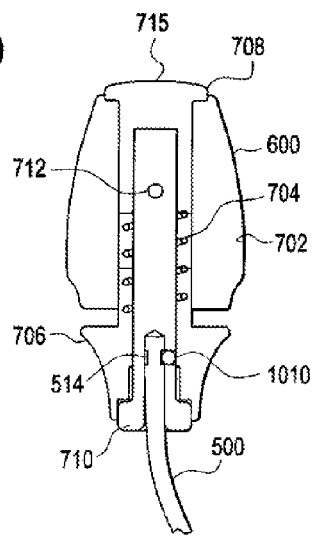
FIG. 10
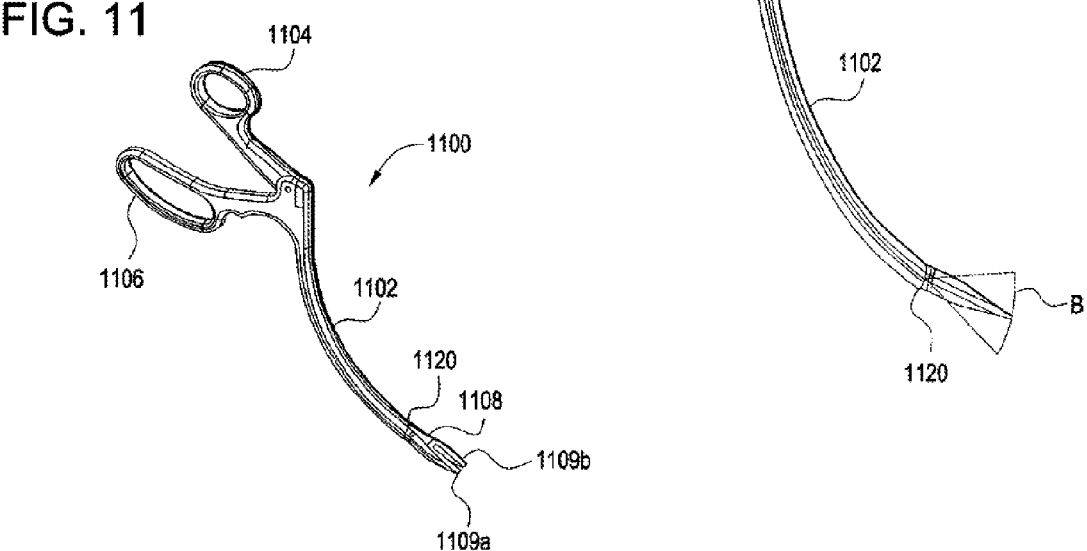
FIG. 11
FIG. 12

FIG. 13
FIG. 14
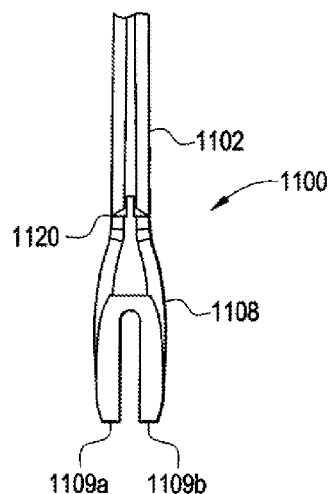
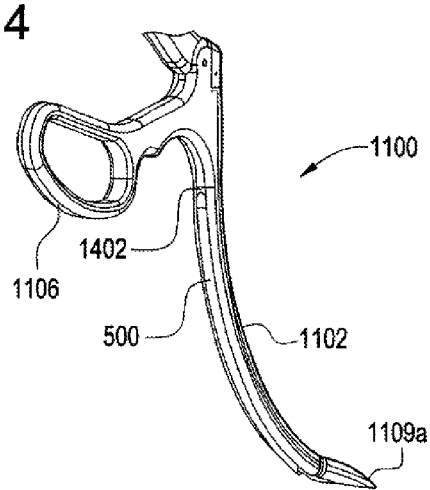
FIG. 15
FIG. 16
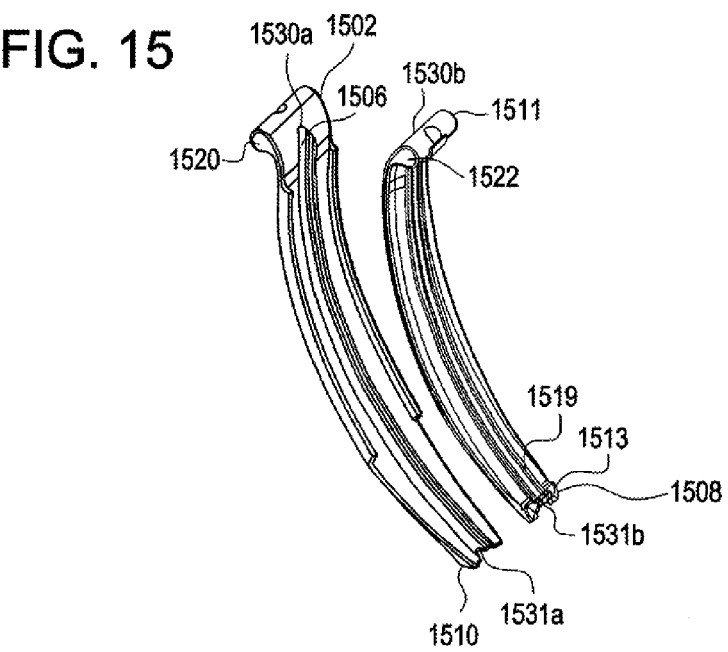
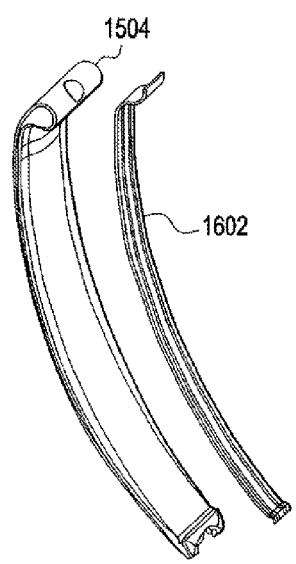

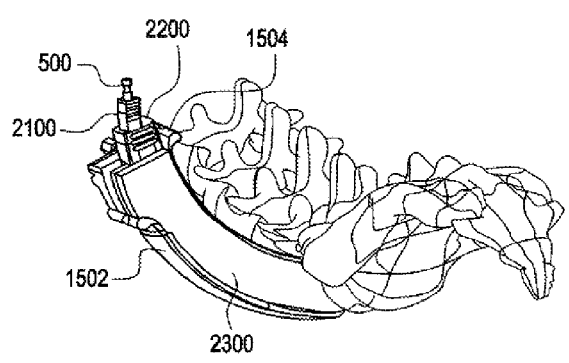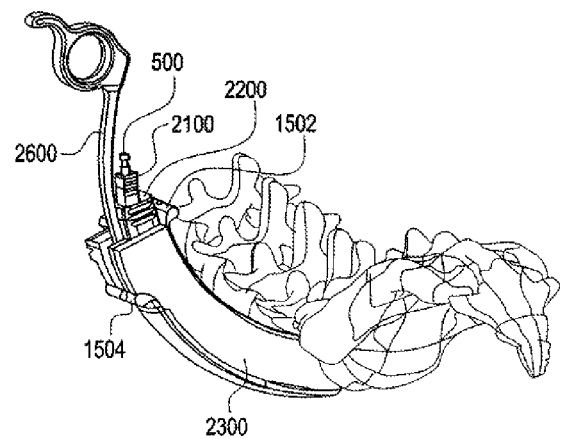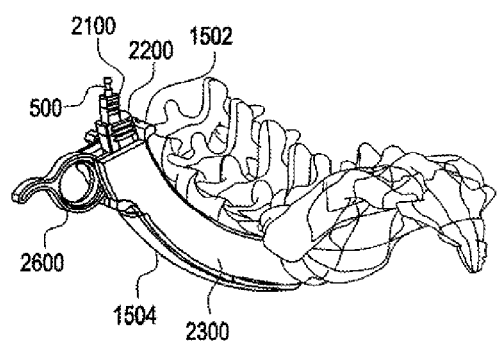

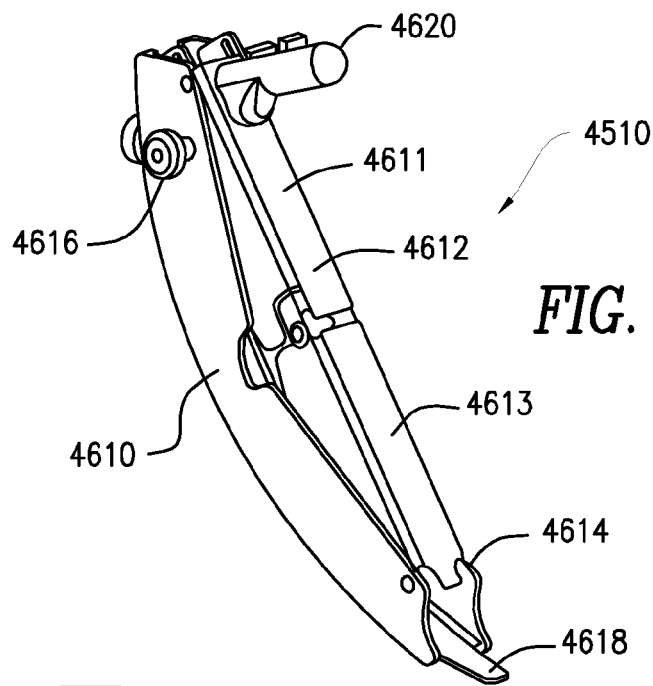
FIG. 46a
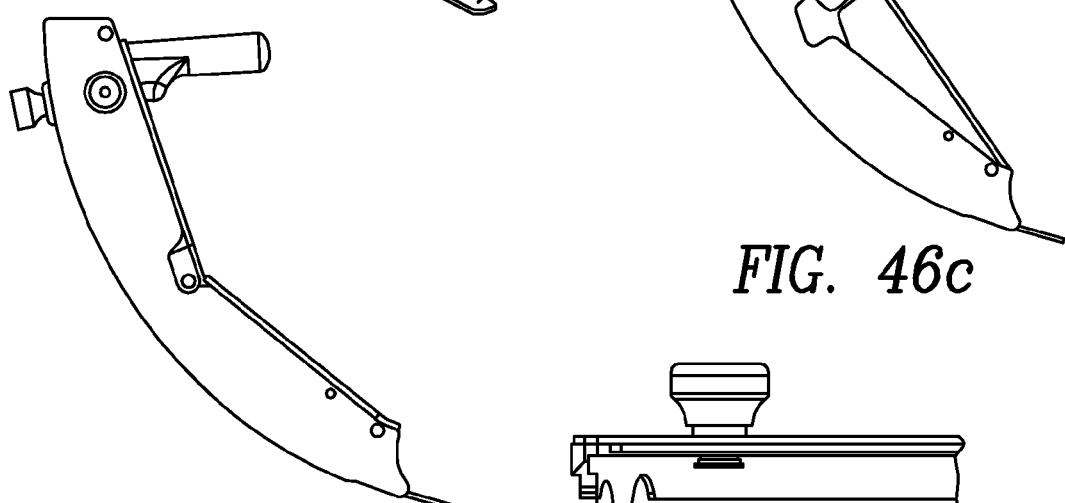
FIG. 46b
FIG. 46c
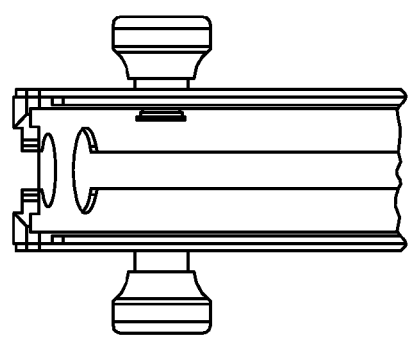
FIG. 46d

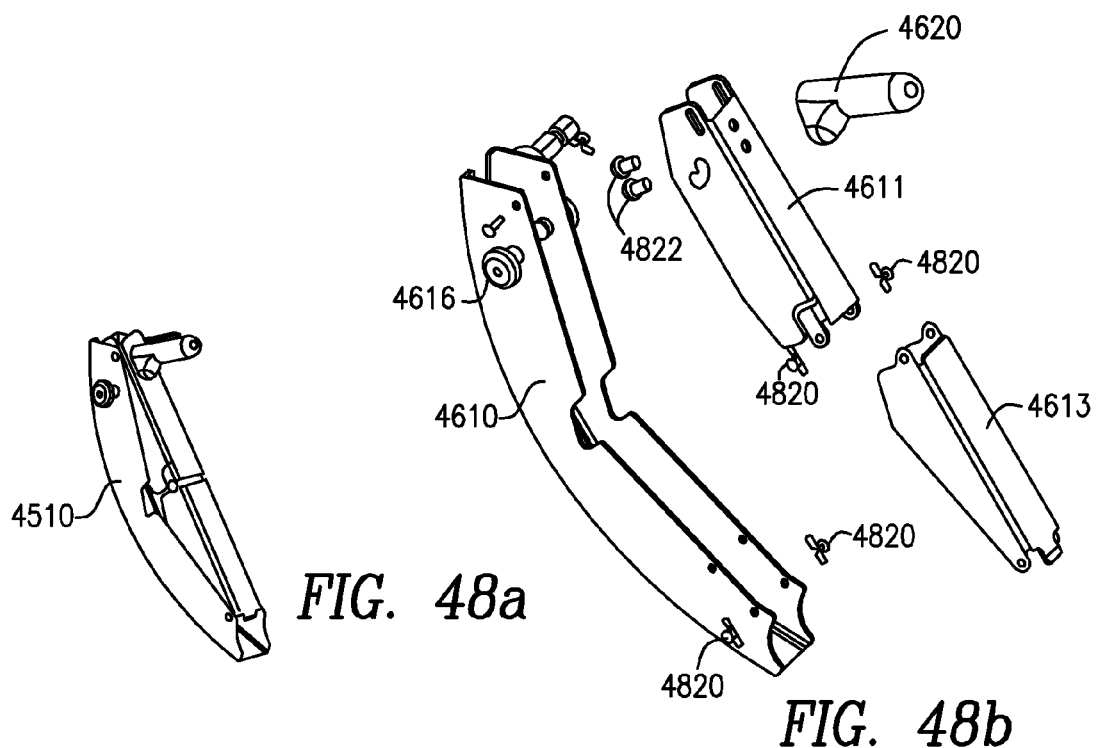
FIG. 48a
FIG. 48b
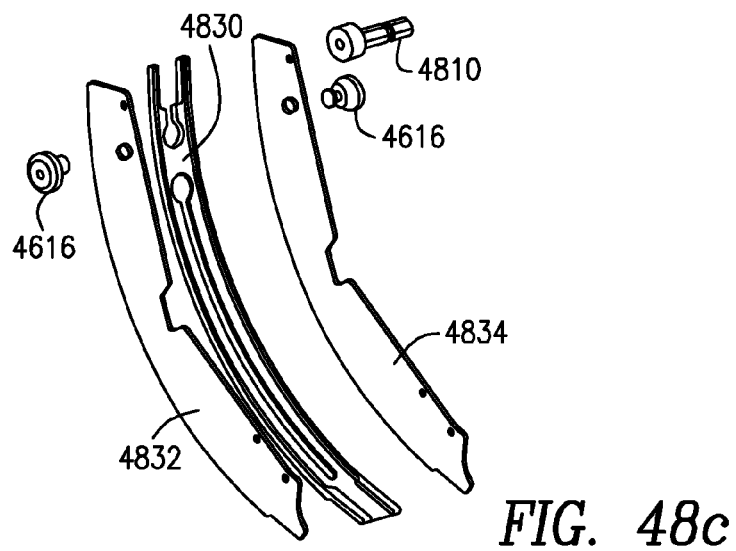
FIG. 48c

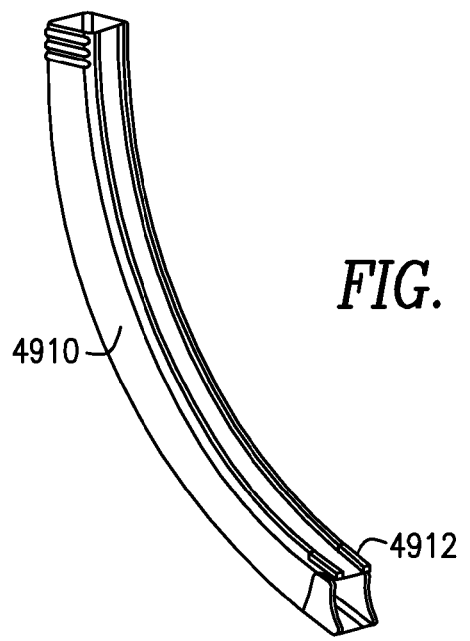
FIG. 49a
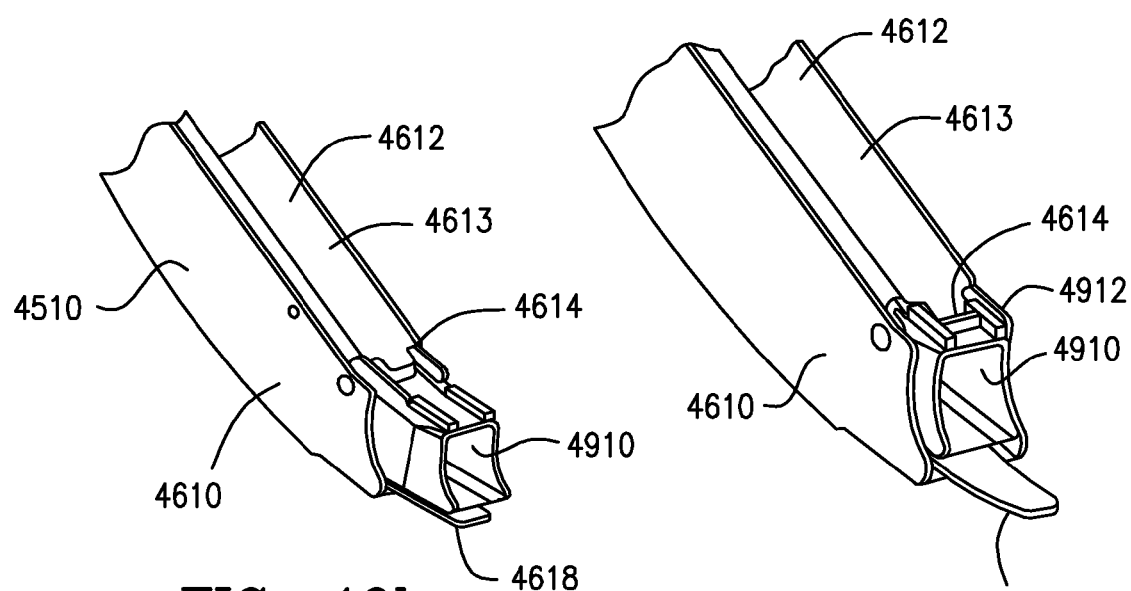
FIG. 49b
FIG. 49c

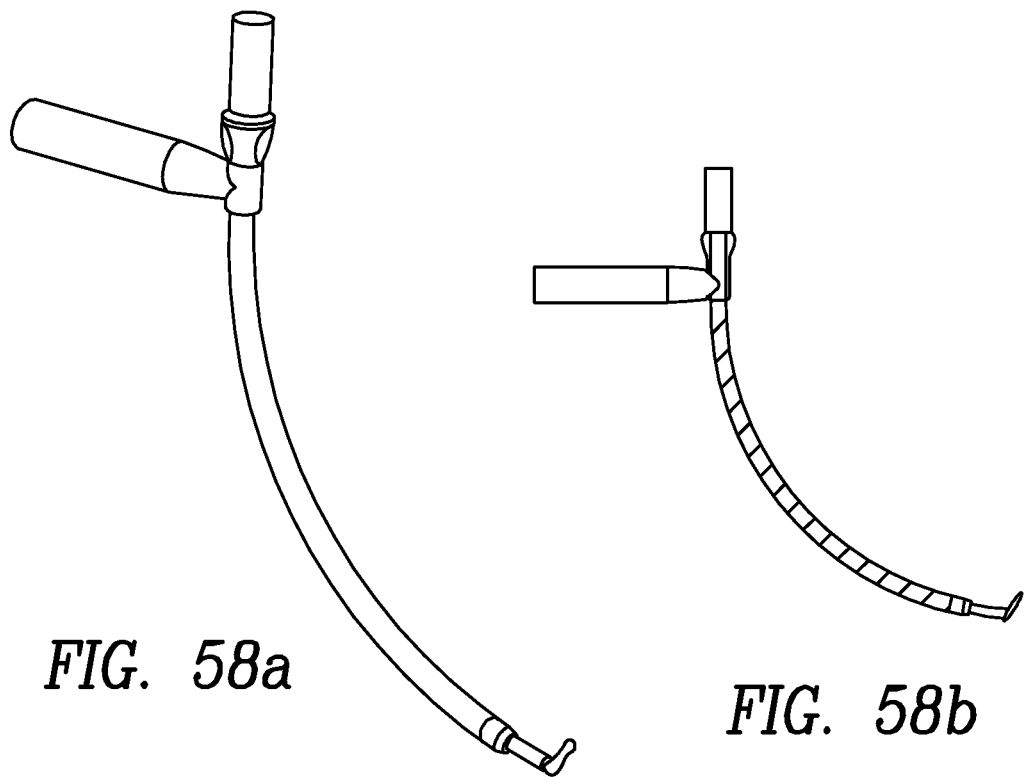
FIG. 58a
FIG. 58b
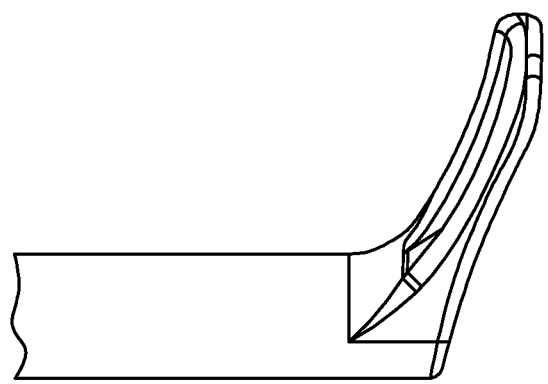
FIG. 58c

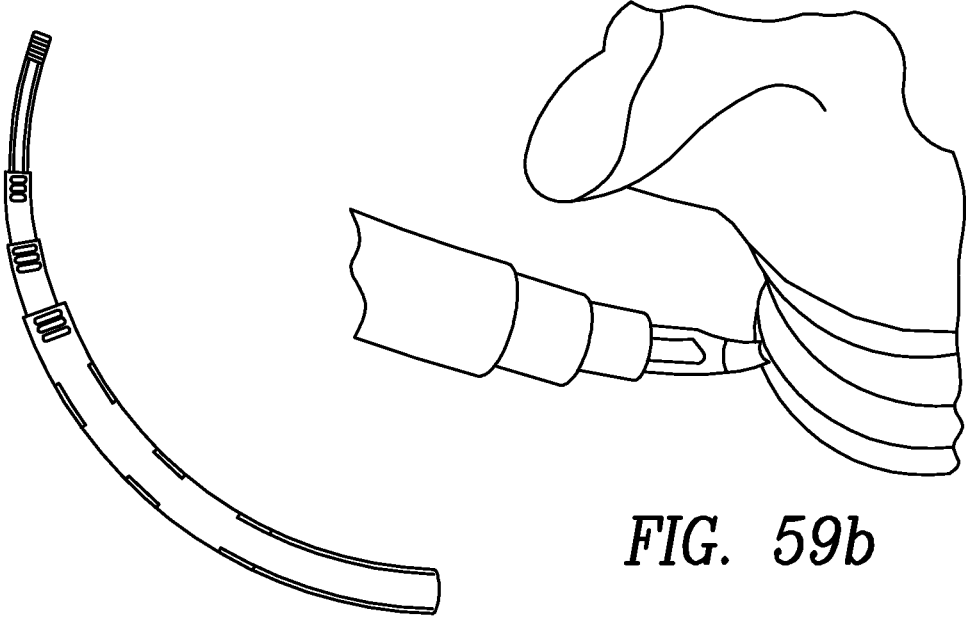
FIG. 59b
FIG. 59a
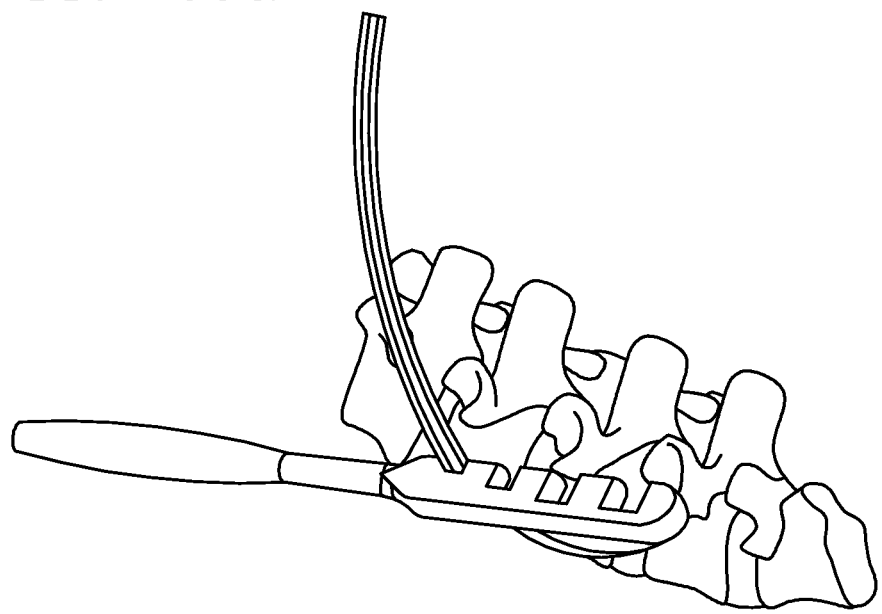
FIG. 59c

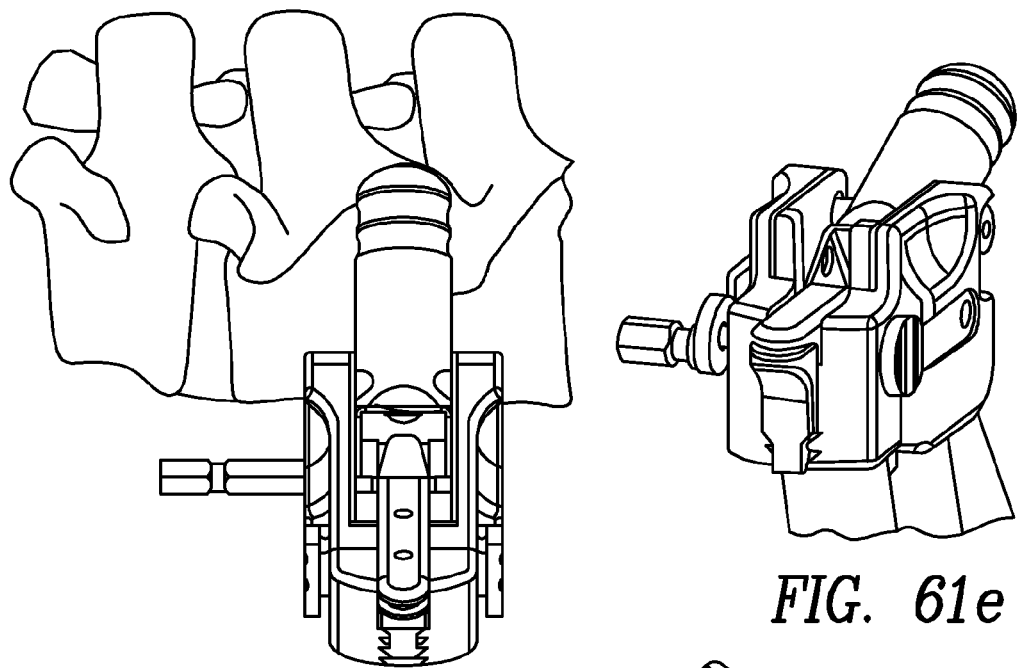
FIG. 61d
FIG. 61e
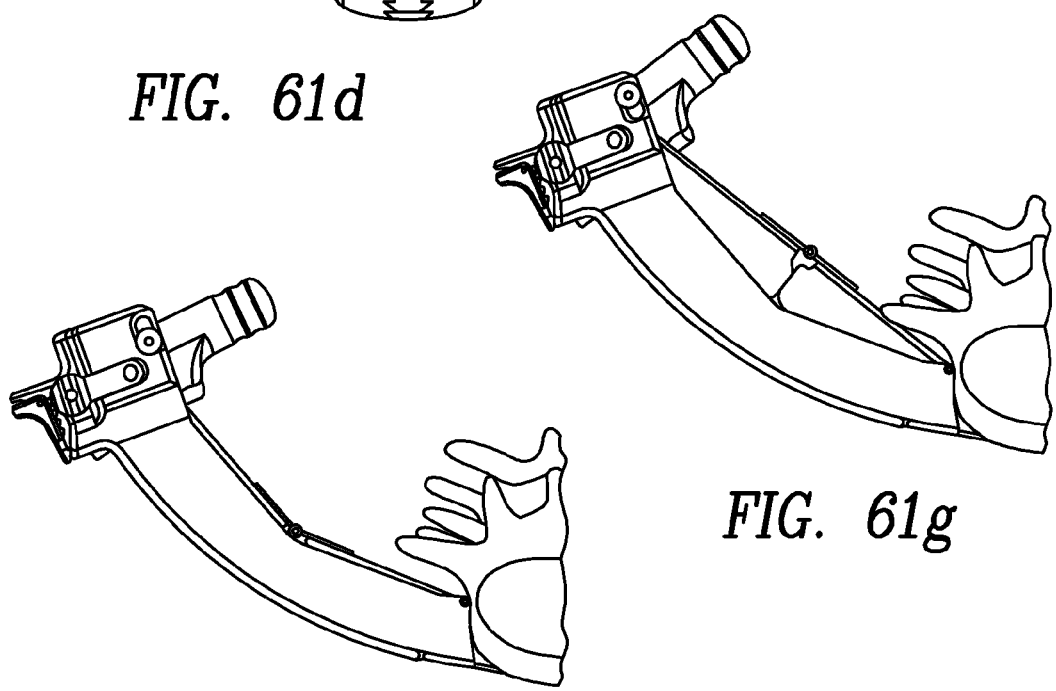
FIG. 61f
FIG. 61g

Three connection points, including anterior attachment for modified ALIF

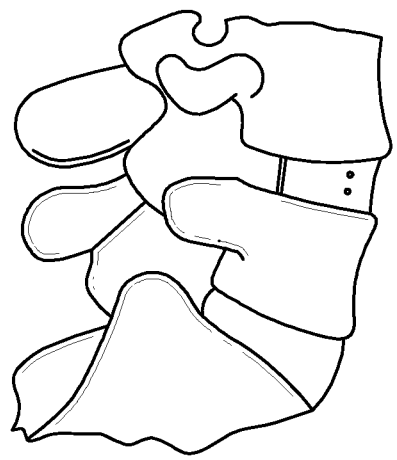
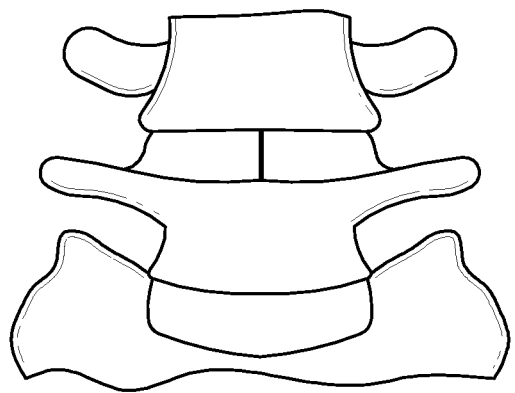
FIG. 71a  FIG. 71b
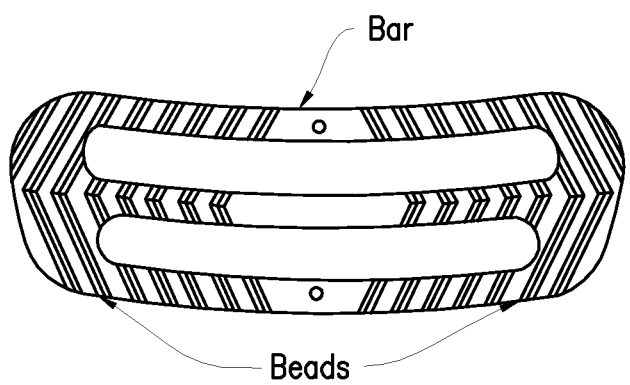
FIG. 71c

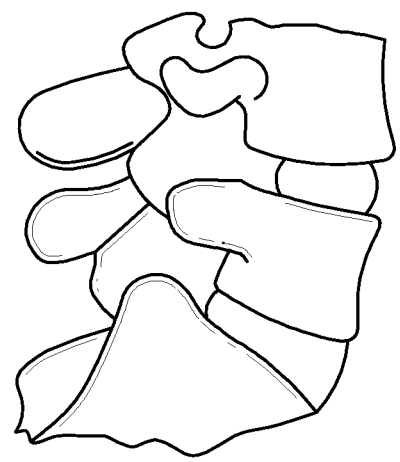 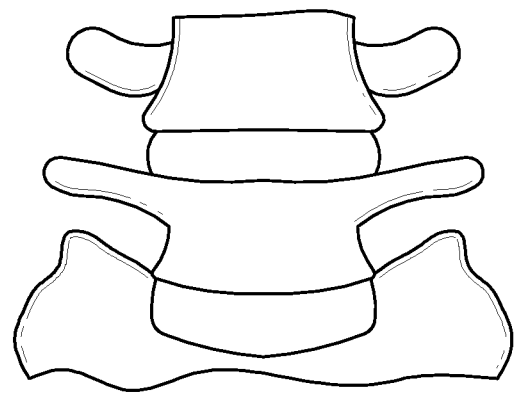
FIG. 72a    FIG. 72b
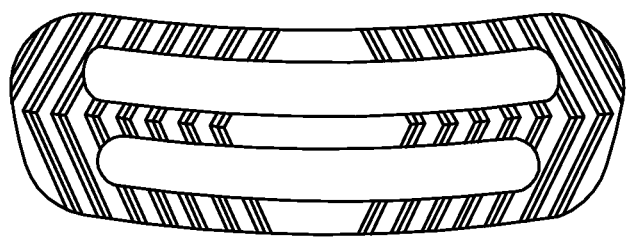
FIG. 72c

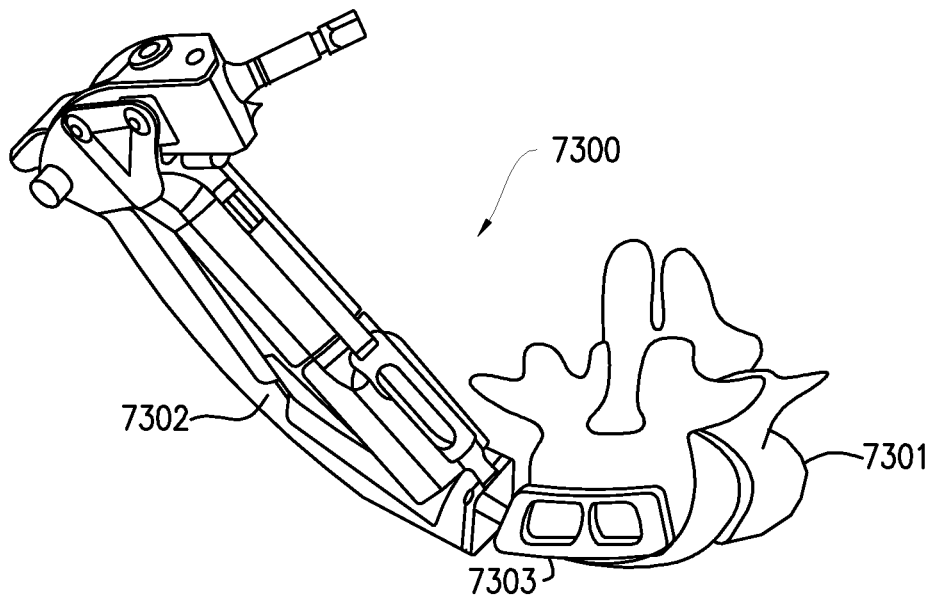
FIG. 73
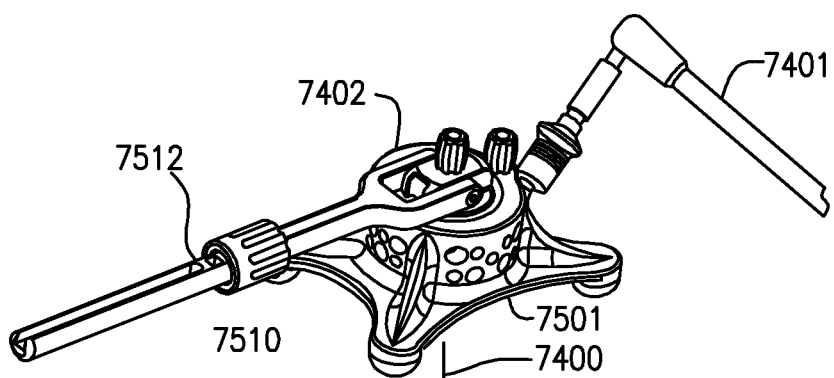
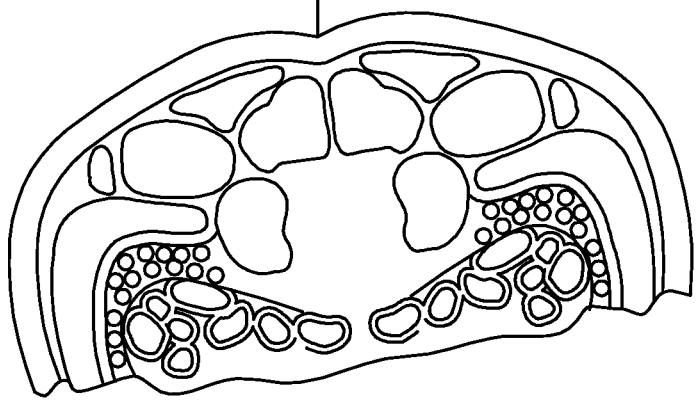
FIG. 74

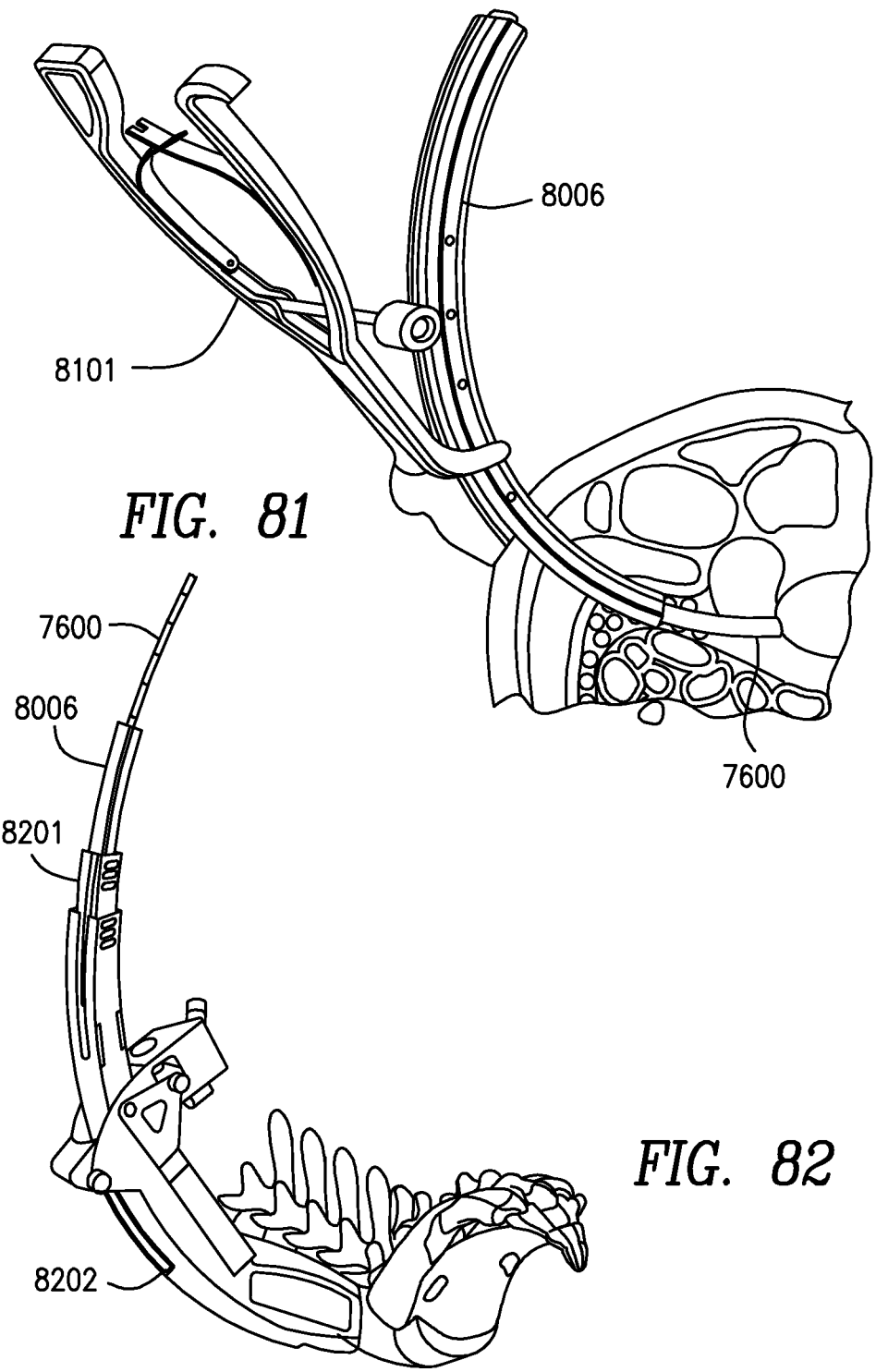

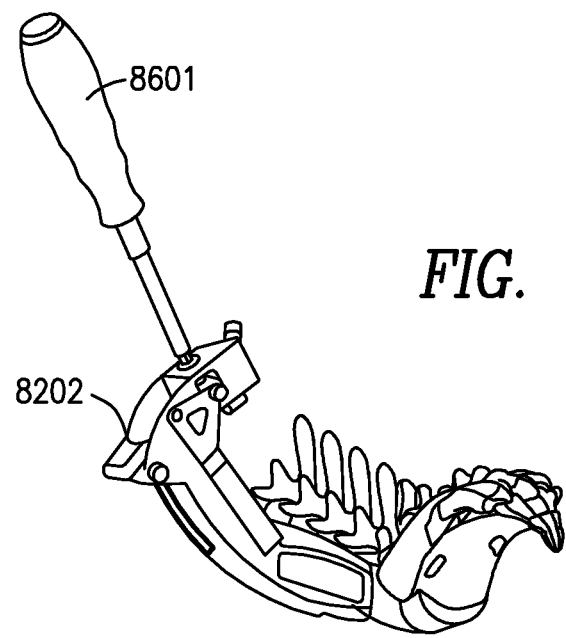
FIG. 86
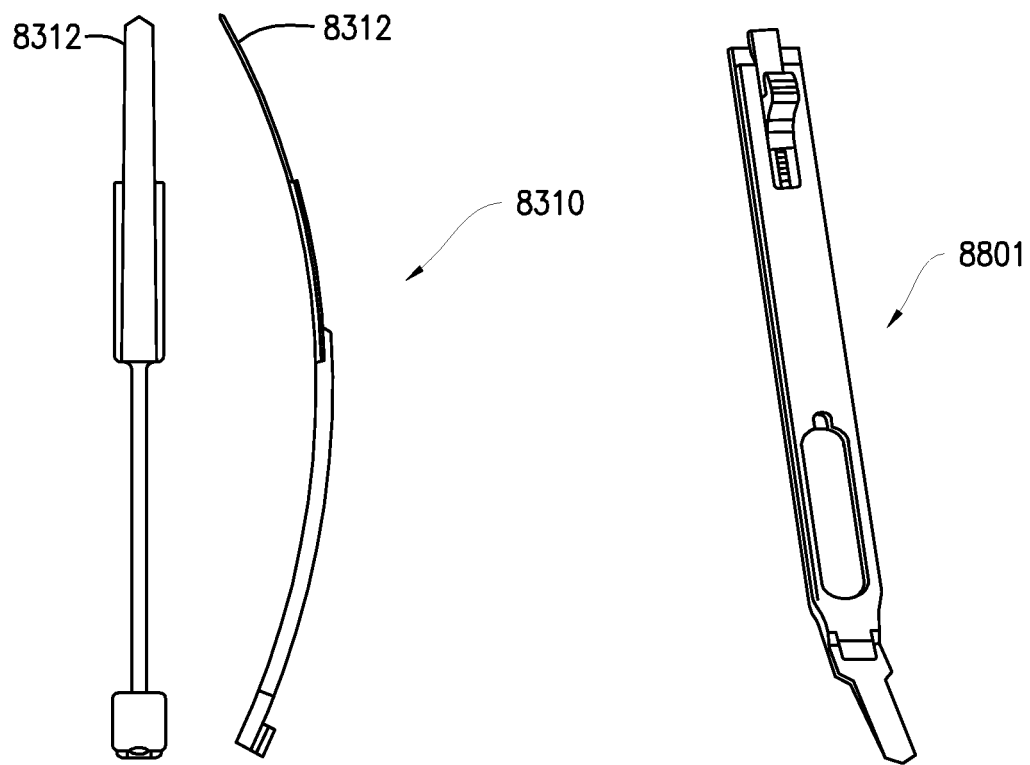
FIG. 87
FIG. 88

CURVILINEAR SPINAL ACCESS METHOD AND DEVICE

CROSS-REFERENCE TO RELATED APPLICATIONS

The present application is a Continuation-in-Part of U.S. patent application Ser. No. 12/069,721, to Garcia-Bengochea, filed Feb. 11, 2008, which claims priority to U.S. Provisional Application No. 60/900,554, to Garcia-Bengochea, filed Feb. 9, 2007, entitled "GUIDED LUMBAR INTERBODY FUSION METHOD AND SYSTEM". The present application also claims priority to U.S. Provisional Patent Application Nos. 61/135,829, filed Jul. 23, 2008; 61/195,848, filed Oct. 10, 2008; and 61/175,460 filed May 5, 2009, all entitled "CURVILINEAR SPINAL ACCESS METHOD AND DEVICE"; and U.S. Provisional Patent Application No. 61/192,210, filed Sep. 16, 2008, entitled "INTERBODY SPACER". The present application incorporates the entire disclosures of these applications herein by reference.

BACKGROUND OF THE INVENTION

1. Field of the Invention

This invention relates generally to the field of surgery. In particular, the present invention relates to the field of surgical access to the spine.

2. Background of the Invention

This invention relates generally to the field of devices, methodologies and systems involved in lumbar interbody fusion, wherein an interbody device or implant is positioned between adjacent vertebrae in order to stabilize or fuse the vertebrae. Modern surgical techniques for this are relatively minimally invasive, in that improved techniques, instrumentation and implant design allow the site to be prepared and the implant to be introduced through one or several small incisions in the patient.

Surgical procedures known as lumbar interbody fusion (LIF) have become common over the past ten years. Particular techniques are typically designated by the direction of approach relative to the spine—anterior (ALIF), posterior (PLIF), transverse (TLIF), and extreme lateral (XLIF). While these procedures are an improvement over conventional surgery in that muscular disruption and trauma are minimized, difficulties in the techniques have limited widespread adoption in the medical community.

For example, anterior approaches require the use of an access surgeon in addition to the spinal surgeon to navigate through the belly and require mobilization of the abdominal viscera and great vessels. Anterior approaches also do not safely allow for revision or re-exploration and can incur additional complication such as ileus and abdominal pain. Should further fixation be required these approaches do not allow posterior fixation without repositioning the patient; this procedure is commonly called a 360 operation where the operation begins with the patient in the supine position for the ALIF procedure and then flipped, re-sterilized and posterior fixation is applied with the patient in the prone position. These procedures increase time of operations which directly relates to blood loss, recovery time and hospital fees.

Posterior and transverse approaches require provide some advantages over anterior approaches yet still require some exposure of the nerves or theral sac, making placement of large (and therefore more stable) implants difficult; therefore posterior and transverse approaches use fixation devices smaller than anterior approaches.

Extreme lateral approaches still provide some advantages over previously discussed procedures yet require cumbersome positioning, long operating distances and provide no access to the spinal canal. In these approaches the patient is placed on their side which allows a larger access area to implant a bigger device but does not overcome the setback of repositioning the patient should posterior fixation be required.

It would be desirable to develop a posterior-lateral approach that combines the advantages of both the posterior and lateral approaches.

SUMMARY OF THE INVENTION

In a first aspect, embodiments of the present invention provide a curvilinear access device having an expandable working portal. The device includes a slide having an channel with an open top and a movable top sized to cover the open top of the channel forming an expandable working portal with a proximal end and a distal end, wherein the movable top is movable between a closed position and an open position, wherein in the closed position the movable top blocks direct visualization between the proximal end and the distal end of the expandable working portal, and in the open position movement of the movable top results in direct visualization from the proximal end to the distal end of the expandable working portal.

In many embodiments, the movable top is positioned proximate the open top of the channel in the closed position and portions of the movable top are positioned away from the open top of the channel in the open position.

In many embodiments, the movable top includes a proximal end and distal end, the proximal end being pivotally secured near the proximal end of the working portal and the distal portion being pivotally secured near the distal end of the working portal.

In many embodiments, the movable top comprises a proximal portion pivotally secured to a distal portion.

In many embodiments, the device further includes opening means configured to move the movable top between the closed and open positions.

In many embodiments, the opening means is selected from a group consisting of a handle, actuation screw, screw actuator, expansion screw and push buttons.

In many embodiments, the movable top is in the closed position during insertion of the device to a surgical site.

In many embodiments, the slide is substantially curved.

In many embodiments, the device is used to access a surgical site, the device having a distal end configured to be disposed at the surgical site and a proximal end disposed away from the surgical site, and wherein the open position allows direct visualization through the expandable working portal of the surgical site.

In many embodiments, the expandable working portal is configured to allow advancement of at least one surgical tool and/or at least one implant toward a surgical site in the open position.

In many embodiments, the channel includes a back portion with side portions.

In many embodiments, the expandable working portal has a width in a range of 5 mm to 30 mm and an expandable height in a range of 5 mm to 30 mm.

In many embodiments, the expandable working portal is configured to accommodate insertion of an implant having a height in the range of 8 mm to 18 mm, an anterior-posterior depth in a range of 8 mm to 30 mm, and a lateral width in the range of 20 mm to 70 mm.

In many embodiments, the expandable working portal has a cross-section selected from the group consisting of: square, rectangular, oval, polygonal.

In many embodiments, the device is used in a surgical procedure selected from a group consisting of nucleus replacement, total disc replacement, interbody fusion, discectomy, neural decompression, implant delivery and any other surgical procedure.

In many embodiments, the device is used to deliver an implant selected from a group consisting of a bone screw, a plate, an interbody device, an artificial disc, and any other implantable device.

In many embodiments, the device further includes an anterior awl having an anterior tang slidaby coupled to the slide, the anterior tang configured to extend distally proximate a lower portion of the expandable working portal.

In many embodiments, the device further includes a posterior tang slidaby coupled to the slide or top and configured to extend distally proximate an upper portion of the expandable working portal.

In many embodiments, the device further includes a post configure to engage a holding arm assembly.

In many embodiments, the slide and/or top are made from metal, plastic, polymer, or other suitable material.

In many embodiments, the slide and/or top are made from polyetheretherketone ("PEEK").

In another aspect, embodiments of the present invention provide a system for performing a procedure at a surgical site of the spine of a patient. The system includes a curvilinear access device having a distal end configured to be disposed at the surgical site and a proximal end disposed away from the surgical site, the curvilinear access device including a slide having a channel with an open top, and a movable top sized to cover the open top of the channel forming an expandable working portal with a proximal end and a distal end, wherein the movable top is movable between a closed position and an open position, wherein in the closed position the movable top blocks direct visualization between the proximal end and the distal end of the expandable working portal and in the open position movement of the movable top results in direct visualization from the proximal end to the distal end of the expandable working portal, and at least one surgical tool configured to pass through the working channel in the open position to the surgical site to perform the surgical procedure.

In many embodiments, the system further includes a guide wire delivery instrument configured to deliver a guide wire to the surgical site and one or more sequential dilators configured to slide on the guide wire to open tissue, wherein the working portal is configured to slide on the one or more sequential dilators when accessing the surgical site.

In many embodiments, the guide wire delivery instrument includes a calibrated introducer configured to locate an external reference point for insertion of a first dilator from the skin to the surgical site, advancing the guide wire through a cannula of the first dilator into the surgical site.

In many embodiments, the procedure is selected from a group consisting of: nucleus replacement, total disc replacement, interbody fusion, discectomy, neural decompression, implant delivery and any other surgical procedure.

In many embodiments, the surgical tool is selected from the group consisting of a psoas muscle separator, a tissue retractor, an osteotome, an instrument for removing the annulus, a rongeur tool, a plurality of curettes, a rasp, a disk whisk tool, an implant inserter, a nerve retractor a drill, and an endoscope.

In many embodiments, the system further includes an implant delivered to the surgical site through the expandable working portal, wherein the implant is selected from a group consisting of: a bone screw, a plate, an interbody device, an artificial disc, and any other implantable device.

In many embodiments, the system further includes a holding arm assembly coupled to the slide.

In another aspect, embodiments of the present invention provide a method for performing a surgical procedure on the spine of a patient. The method includes advancing a distal end of a curvilinear access device at a surgical site located at the spine of the patient, the curvilinear access device including a slide having a channel with an open top and a movable top sized to cover the open top of the channel forming an expandable working portal with a proximal end and a distal end, wherein the movable top is movable between a closed position and an open position, wherein in the closed position the movable top blocks direct visualization between the proximal end and the distal end of the expandable working portal and in the open position movement of the movable top results in direct visualization from the proximal end to the distal end of the expandable working portal, moving the movable top from the closed to the open position, directly viewing the surgical site through working portal and advancing at least one surgical tool and/or at least one implant toward the surgical site via the working portal to perform the surgical procedure.

In many embodiments, the method further including locking the curvilinear access device to the surgical site with an anterior tang of an anterior awl slidaby coupled to the slide extending distally proximate a lower portion of the expandable working portal.

In many embodiments, the system further including sweeping the distal end of the working portal clear of tissue and/or nerve roots with a posterior tang slidaby coupled to the slide or top extending distally proximate an upper portion of the expandable working portal.

In many embodiments, the system further including delivering a guide wire to the surgical site using a guide wire delivery instrument, sliding one or more sequential dilators on the guide wire opening tissue and sliding the working portal on the one or more sequential dilators.

In many embodiments, the guide wire delivery instrument includes a calibrated introducer configured to locate an external reference point for insertion of a first dilator from the skin to the surgical site, and advancing the guide wire through a cannula of the first dilator into the surgical site.

In another aspect, embodiments of the present invention provide a device for performing a procedure on the spine of a patient. The device includes a working portal configured to be advanced toward a surgical site of the spine of the patient, the working portal including a distal end and a proximal end, a working portal housing having an interior channel with an open top disposed between the distal end and the proximal end, a movable top configured to be secured to the working portal housing, the distal end is configured to be disposed at the surgical site and the proximal end is disposed away from the surgical site, the housing has a curved shape defined between the proximal end and the distal end, the movable top is configured to cover the open top of the interior channel of the working portal housing, and the working channel is configured to allow advancement of at least one surgical tool and/or at least one implant toward the surgical site.

In many embodiments, the proximal end is disposed at an angle with respect to the distal end.

In many embodiments, the movable top includes a proximal portion and distal portion, the proximal portion is pivotally secured to the proximal end of the working portal housing and the distal portion is pivotally secured to the distal end of the working portal housing, and the proximal portion is pivotally secured to the distal portion.

In many embodiments, the working portal housing includes at least one actuation means configured to open and close the movable top.

In many embodiments, the device further including an anterior awl configured to be advanced toward the surgical site along the working portal housing and further configured to anchor the working portal at the surgical site.

In many embodiments, the device further including a nerve retracting mechanism configured to remove nerve tissue away from the surgical site In many embodiments, the surgical procedure is selected from a group consisting of: nucleus replacement, total disc replacement, interbody fusion, discectomy, neural decompression, implant delivery and any other surgical procedure.

In many embodiments, the working portal is used to deliver an implant, wherein the implant is selected from a group consisting of: a bone screw, a plate, an interbody device, an artificial disc, and any other implantable device.

In many embodiments, the device can be implemented with a guide wire delivery instrument configured to deliver a guide wire to the surgical site.

In many embodiments, the surgical tool is selected from the group consisting of a psoas muscle separator, a tissue retractor, an osteotome, an instrument for removing the annulus, a rongeur tool, a plurality of curettes, a rasp, a disk whisk tool, an implant inserter, a nerve retractor, a drill and an endoscope.

In many embodiments, the device can be implemented with a plurality of sequential dilators configured to open tissue for delivery of the portal.

In many embodiments, the sequential dilators can be implemented with an impacting wand configured to aid in impacting an initial dilator in the plurality of sequential dilators into annulus.

In many embodiments, the sequential dilators further include connection points for connecting a dilator impactor configured to provide an impacting surface for advancing sequential dilators.

In another aspect, embodiments of the present invention provide a method for performing a surgical procedure on the spine of a patient. The method including advancing a working portal toward a surgical site located at the spine of the patient, the working portal including a distal end and a proximal end, a working portal housing having an interior channel with an open top disposed between the distal end and the proximal end, a movable top configured to be secured to the working portal housing, the distal end is configured to be disposed at the surgical site and the proximal end is disposed away from the surgical site, the movable top is configured to cover the open top of the interior channel of the working portal housing, the housing has a curved shape defined between the proximal end and the distal end, wherein the proximal end is disposed at an angle with respect to the distal end, and advancing at least one surgical tool and/or at least one implant toward the surgical site via the working channel to perform the procedure.

In many embodiments, the method further includes locking the working portal to the surgical site with an anterior tang of an anterior awl extending from the distal end proximate a lower portion of the working portal.

In many embodiments, the method further includes sweeping the distal end of the working portal clear of tissue and/or nerve roots with a posterior tang extending from the distal end proximate an upper portion of the working portal.

In many embodiments, the method further includes delivering a guide wire to the surgical site using a guide wire delivery instrument, sliding one or more sequential dilators on the guide wire opening tissue, and sliding the working portal on the one or more sequential dilators.

In many embodiments, the guide wire delivery instrument includes a calibrated introducer configured to locate an external reference point for insertion of a first dilator from the skin to the surgical site, and advancing the guide wire through a cannula of the first dilator into the surgical site.

In many embodiments, the surgical procedure is selected from a group consisting of: nucleus replacement, total disc replacement, interbody fusion, discectomy, neural decompression, implant delivery and any other surgical procedure.

In many embodiments, the working portal is used to deliver an implant, wherein the implant is selected from a group consisting of: a bone screw, a plate, an interbody device, an artificial disc, and any other implantable device.

In another aspect, embodiments of the present invention provide a method for performing a surgical procedure on the spine of a patient. The method including advancing a curvilinear access device to the surgical site, the curvilinear access device having an expandable working portal with a movable top, the movable top being movable between a closed position and an open position, wherein in the closed position the movable top blocks direct visualization between the proximal end and the distal end of the expandable working portal and in the open position movement of the movable top results in direct visualization from the proximal end to the distal end of the expandable working portal, moving the movable top from the closed to the open position, directly viewing the surgical site through working portal, and advancing at least one surgical tool and/or at least one implant toward the surgical site via the working portal to perform the procedure.

In many embodiments, the method further includes delivering a guide wire to the surgical site using a guide wire delivery instrument, sliding one or more sequential dilators on the guide wire and open tissue, and sliding the working portal on the one or more sequential dilators.

In many embodiments, the guide wire delivery instrument includes a calibrated introducer configured to locate an external reference point for insertion of a first dilator from the skin to the surgical site, advancing the guide wire through a cannula of the first dilator into the surgical site.

In many embodiments, advancing the curvilinear access device is from a posterior-lateral approach.

Further features and advantages of the invention, as well as structure and operation of various embodiments of the invention, are disclosed in detail below with references to the accompanying drawings.

BRIEF DESCRIPTION OF THE DRAWINGS

The present invention is described with reference to the accompanying drawings. In the drawings, like reference numbers indicate identical or functionally similar elements.

FIG. 10 is detailed sectional view of the trocar/trocar handle interaction, according to some embodiments of the present invention.

FIG. 11 illustrates an exemplary tissue separator, according to some embodiments of the present invention.

FIG. 12 illustrates exemplary working aspects of the tissue separator, according to some embodiments of the present invention.

FIG. 13 illustrates the tear-drop working end geometry of the tissue separator shown in FIG. 11.

FIG. 14 illustrates an exemplary trocar channel cutout on the underside of the tissue separator, according to some embodiments of the present invention.

FIG. 15 illustrates exemplary anterior and dorsal tissue distracters, according to some embodiments of the present invention.

FIG. 16 illustrates an exemplary assembly of a neuro monitoring ribbon installed on the dorsal tissue distracter shown in FIG. 15, according to some embodiments of the present invention.

FIG. 37 illustrates the portal sliding over the dilators, according to some embodiments of the present invention.

FIG. 38 illustrates the anterior awl securing the portal, according to some embodiments of the present invention.

FIG. 39 illustrates the anterior awl being fully seated, according to some embodiments of the present invention.

FIGS. 45, 46*a*-*d*, 47*a*-*d*, 48*a*-*c*, 49*a*-*c*, 50*a*-*b* illustrate an exemplary curved access portal having a movable top for accessing vertebrae, according to some embodiments of the present invention.

FIGS. 58*a*-58*c* illustrate an exemplary psoas muscle separator, according to some embodiments of the present invention.

FIGS. 59a-59c illustrate exemplary sequential dilators, according to some embodiments of the present invention.

FIGS. 61a-61g illustrate an exemplary portal, according to some embodiments of the present invention.

FIGS. 71a-71c illustrate an exemplary implant having a fluoroscopic marker, according to some embodiments of the present invention.

FIGS. 72a-72c illustrate another exemplary implant having a fluoroscopic marker, according to some embodiments of the present invention.

FIG. 73 illustrates an exemplary implant and portal system, according to some embodiments of the present invention.

FIG. 74 illustrates the calibrated introducer and a cross-sectional view of the operative space, according to some embodiments of the present invention.

FIG. 81 illustrates an exemplary dilator impactor tool, according to some embodiments of the present invention.

FIG. 82 illustrates the curved portal as well as the serial dilators, according to some embodiments of the present invention.

FIG. 86 illustrates an exemplary toeing wrench which may be used to expand the curved portal, according to some embodiments of the present invention.

FIG. 87 anterior awl, according to some embodiments of the present invention.

FIG. 88 is a posterior tang or posterior tab, according to some embodiments of the present invention.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Many of the embodiments disclosed herein are directed to curvilinear spinal access methods and devices using in a posterior-lateral approach to the spine. In this approach, the curvilinear device is introduced posterior to the transverse processes of the spine in an arced approach, with the distal end ending up in a lateral position proximate the spine. This allows the patient to be operated on in the prone position while still being able to access the lateral portion of the spine to perform a procedure. In the embodiments having the movable top, direct visualization of the critical anatomy through the device at the operative site is achieved when the top is in the open position. The embodiments of the curvilinear access methods and devices disclosed herein should not be limited to the posterior-lateral approach. The embodiments of the curvilinear access methods and devices disclosed herein should not be limited to the spine and may be used in other orientations and other surgical sites within the body.

The following descriptions provide a general overview of the concepts discussed in the present application. Example procedures A and B are disclosed for many of the embodiments discusses herein. Additional embodiments are discussed below with regard to FIGS. 1-44c and 45-98.

Example Procedure A—This example procedure is generally related to many of the embodiments disclosed in FIGS. 1-44c.

The procedure begins with placing the patient in a prone position and arranging the proper drapery to establish proper sterilization of the operation site. Next, the surgeon uses a measuring device to measure a specified distance from the midline. At this point, the surgeon will make a mark using some marking device as a reference point to create an incision. The specified distance can be calculated using a chart or sliding scale that determines the appropriate distance to make the incision. This distance is directly related to the distance of the center of the vertebral body to the flat surface of the patient's back; given this distance along with the known arc angle of the portal and known center of the midline, the incision distance can be properly calculated.

Figure 28:
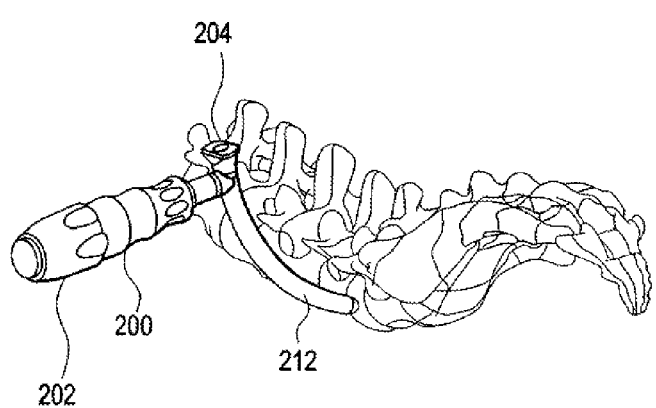
FIG. 28 illustrates an exemplary usage of the trocar guide to reach a "50-yard line" of a vertebral disc, according to some embodiments of the present invention.

An incision is created at the marked point and the surgeon performs blunt dissection with a finger to estimate retroperitoneal space ("RPS") and tissue, such as the psoas muscle. Then, the trocar guide is advanced over the finger of the surgeon into the tissue splitting the fibers vertically until it abuts the spine on the centerline of the vertebral body (as shown in FIG. 28). Positioning of the trocar guide is confirmed with x-ray. The trocar guide has a curved body that has an inner cannulated channel and an offset handle. The instrument may have a small "tooth" on the inner wall to engage the spine and hold it in place. A neurophys stylette can be put in the trocar guide through this process to safely monitor potential nerve disruption. Once successful docking is achieved and the optional neurophys is acceptable, the neurophys stylette is removed.

A cutting trocar is assembled into the trocar handle in preparation for the next procedure. This assembly is created to increase control of the trocar which would be otherwise difficult to hold. In some embodiments, this is accomplished by squeezing a spring loaded collar in the trocar handle which releases a spherical ball while inserting the trocar. Squeezing the spring loaded collar again releases the trocar for removal. The trocar handle can have a solid core made of strong enough material to be hit with a hammer and maintain control of the trocar.

The cutting trocar of similar shape and size as the neurophys stylette with a 2.5 mm trocar tip is then passed through the cannulated channel in the trocar guide to pierce the annulus 15 mm deep. To facilitate better control the trocar handle can be applied to the cutting trocar. A mallet may also be used to pierce the stylette into the disc space approximately 1 cm. The cutting trocar is then replaced with the barbed trocar which is similarly sized and has a 15 mm tip that is pointed with a blunt tip and barbed features to anchor the trocar in the disc. The trocar handle can be similarly applied to facilitate handling of the barbed trocar. The barbed trocar can be "tapered" or "notched" so that the annulus "grabs" the anchor. The trocar handle is removed from the trocar and the trocar guide can be removed.

The tissue separator is followed down the length of the barbed trocar to the lateral surface of the spine, such as the vertebral disc annulus. The device is actuated to "peel" tissue, such as muscle, off the spine and prepare the surgical site for further instrumentation, similar to periosteal elevators. In some embodiments, a ringed handle is contracted and expanded to create a sweeping motion of a blade at the end of the tissue separator instrument. This blade can be of teardropped shape to better facilitate insertion and removal of the device with minimal anatomic disruption and can be bifurcated to enable "peeling" of the tissue above and below the trocar without removing the instrument to "peel" above then reinserting to "peel" below the trocar. There can also be features to help maintain the instrument along the trocar. The tissue separator is then removed.

The tissue distracters are then assembled in the tissue distracter alignment block so that the ends of the tissue distracters are together. The tissue distracters are curved instruments of suitable material and geometry to move anatomy without harming or otherwise disrupting the patient's internals. The tips of the tissue distracters contain a lip of approximately 5 mm in order to "catch" the tissue along the spine and maintain positioning against the lateral wall of the spine. The tips of the tissue distracters can also be tapered to aid in insertion. The opposite ends of the tissue distracters have geometry to interact with the alignment block. This end also has outwardly curved geometry to facilitate the later part of the procedure. The dorsal tissue distracter can have neurophys in the form of a cable or ribbon to help monitor nerve disruption during installation and through the remainder of the operation. To aid in keeping this assembly together, an elastic polymer sheath can be slipped over assembly before insertion. The alignment block is removed.

The small dilator is then pushed between outwardly curved geometry through the tissue distracters and over the barbed trocar until it abuts the lateral wall of the spine. This procedure in turn expands the distance between the tissue distracters. A second large dilator is then followed in a similar fashion to further distract tissue distracters. Though only two dilators are described in the above embodiment, more sequential smaller dilators can be used. The dilators are created in such fashion that they are consecutively smaller in length so that the end part from the preceding dilator protrudes from the subsequent dilator to aid in the later removal. Finger notches can be added for better grip while insertion and removal. Through this process the sheath aids in preventing tissue creep between tissue distracters.

The curved portal is then passed over the largest dilator between the tissue distracters. Proper location is verified and adjusted using X-ray and endoscopic visualization. Once proper location is achieved, the anterior awl is passed through a channel in the curved portal to firmly "dock" the assembly to the annulus. Further, a stabilization arm can be applied to a boss feature off the curved portal. At this point, the barbed trocar and dilators can be removed. The portal is securely docked and ready to begin the technique.

In some embodiments, to safely guide the portal to the surgical site, the curved portal has slots and/or rails that interact with preceding instrumentation that also includes corresponding slots and/or rails. Examples of the preceding instrumentation include, but are not limited to, trocars, tissue distracters, and/or dilators.

Specialized curved instrumentation, inserted through the curved portal, is then used to complete the surgical procedures. In some embodiments, this instrumentation can have slots and/or rails which interact with the curved portal to safely guide instrumentation to the surgical site. In at least one embodiment, these procedures include removing the annulus, cleaning and preparing the disc space, inserting and securing the implant. In these embodiments, instrumentation can include an annulotomy knife, disc whisk, curettes, chisels, implant trials and curved inserting devices. In the embodiments where an implant is used in the procedure, proper location of the implant is then confirmed via x-ray. Finally, the curved portal and tissue distracters are removed to complete the procedure. Posterior fixation can then begin, if needed.

Figure 45:
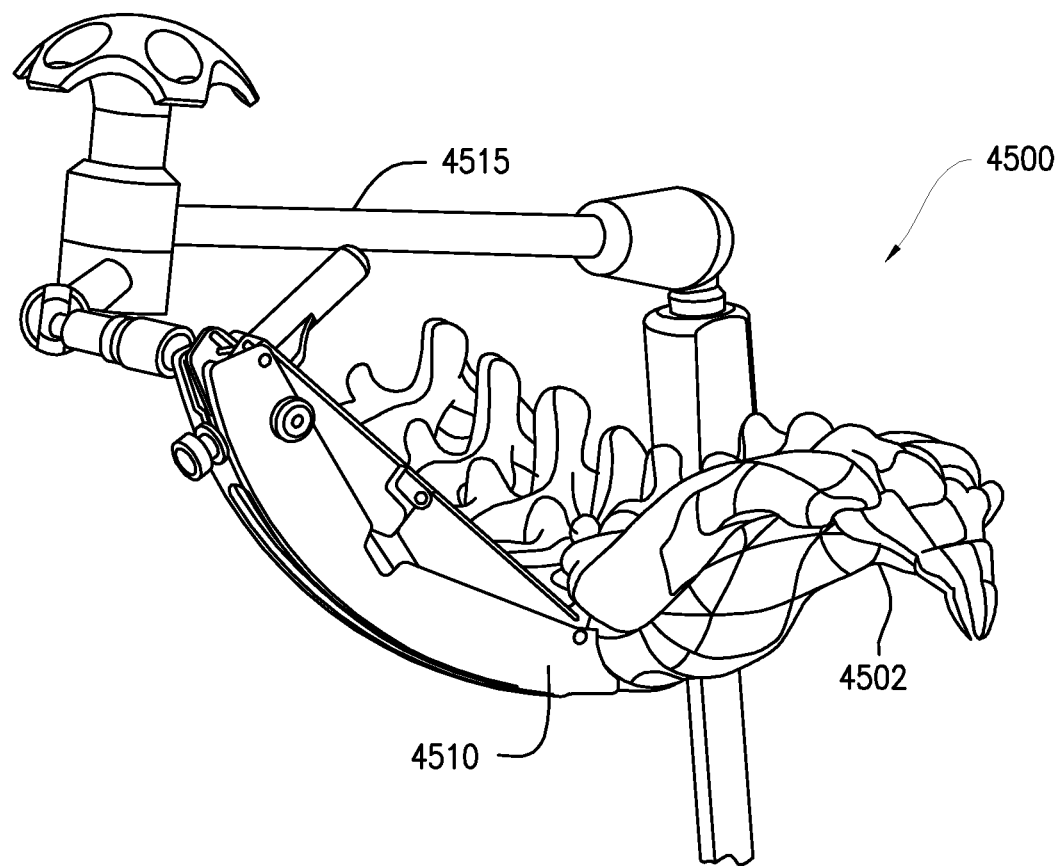
Figure 98:
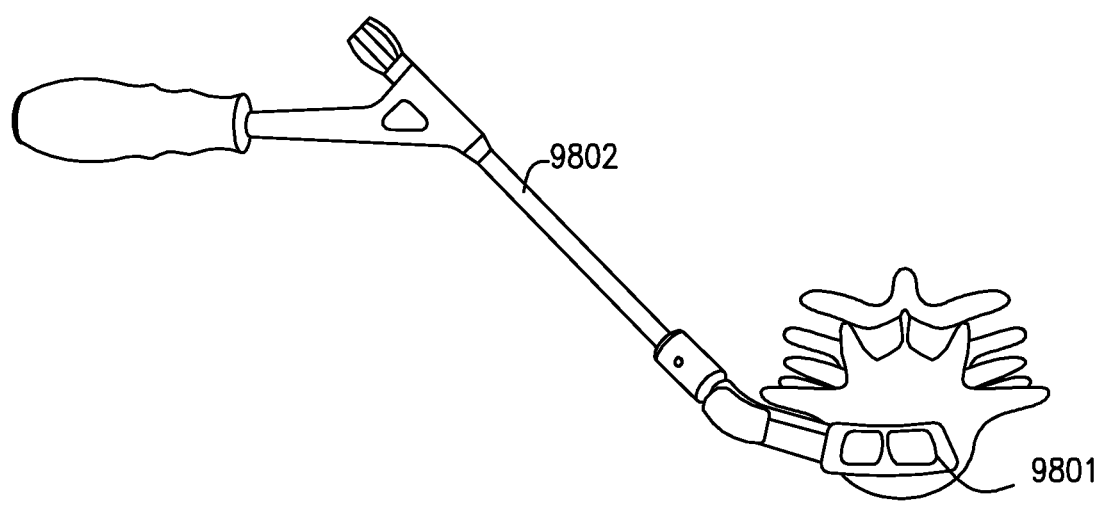
FIG. 98 illustrates the implant and implant inserter with respect to the vertebral body, according to some embodiments of the present invention.

Example Procedure B—This example procedure is generally related to many of the embodiments disclosed in FIGS. 45-98.

The procedure begins with placing the patient in a prone position on the surgical table and, with the aid of lateral fluoroscopy, adjusting the patient so that the operative disc space is generally perpendicular with the operating room floor. Using lateral fluoroscopy, a locating wire is placed directly posterior to the center of the disc space at the desired level. The locating wire is then advanced approximately 5 mm past the posterior portion of the localized spinous process. A calibrated introducer is placed over the locating wire. A vertical pin is then slid over the end of the swing arm of the calibrated introducer until the vertical pin is approximately 1 cm away from the patient's skin. Using lateral fluoroscopy, the height and positioning of the vertical pin is adjusted until a distal tip of the vertical pin approximately lines up with the center of the vertebral disc. Dilator A is then attached to the calibrated introducer at a marked location along the dilator.

A swing arm of the calibrated introducer is then rotated until the tip of dilator A contacts the patient's skin. The skin is marked to indicate the incision location. The surgeon then finger palpates through the subcutaneous tissue layers into the retroperitoneal space, typically indicated by a loss of muscle tissue resistance. Once inside the retroperitoneal space, the surgeon may use his index finger to create space and sweep the peritoneum anteriorly.

In some embodiments, the next step is to insert a neuromonitoring probe through of dilator A. With the surgeon's finger placed close to the distal tip of dilator A, he simultaneously advances his finger and rotates the swing arm to deliver dilator A into the retroperitoneal space through the psoas muscle up to the annular wall of the desired location. Proper dilator placement can be confirmed with lateral then anterior-posterior fluoroscopy followed by removal of the neuromonitoring probe. Through cannula of dilator A, a guidewire can now be delivered and impacted into the vertebral disc. Dilator A may be impacted into the vertebral disc space using a mallet and the dilator impactor.

The surgeon should next begin the soft tissue dilation by placing a neuromonitoring probe through preferred posterior channel of dilator B until the probe contacts the stops at the distal end of the dilator tip. Dilator B may now be placed over dilator A and advanced into the skin incision until it reaches the lateral wall of the anterior spinal column. The neuromonitoring probe should now be removed from dilator B. Successive dilators, such as dilator C, may then be delivered in a similar fashion.

The surgeon may now establish a working area by delivering a curved portal over dilator C and fully seated it against the lateral wall of the anterior spinal column. Lateral location of the curved portal can be verified using anterior-posterior fluoroscopy with dilators optionally still in place. Connect the anterior awl impactor to the anterior awl and impact the instrument to deliver the anterior awl into the disc space. Confirm depth of anterior awl delivery using anterior-posterior fluoroscopy and remove the anterior awl impactor. Remove all curved dilators from the patient starting with dilator A, then dilator B then dilator C.

A moveable top of the curved portal can now be opened with the toeing wrench allowing for direct visualization. The posterior tab is then connected to the posterior tab inserter and delivered through the curved portal. It may be necessary to impact the tab into the annulus. Securing of the posterior tab to the curved portal can be accomplished by engaging the distal portion of the tab into the slots of the curved portal and clipping the proximal portion of the tab into the tab holding clip. The posterior tab may be released from the posterior tab inserter by rotating the knob counter clockwise.

Now that the curved portal has been inserted into the patient, any one of many surgical procedures can now be performed through the portal, including removal of annulus material, vertebral distraction, implant insertion, fusion procedures. Tools used in these procedures may include a rotating actuator, shaver blade, osteotomes, cobbs.

In one particular embodiment the surgeon may choose to perform a discectomy and/or remove a portion or all of the patient's annulus in the following manner. The surgeon may use an annulotomy knife to make the initial incision into the annulus and then use curved pituitaries to remove annulus material and the nucleus if necessary. The surgeon may also use a curved Kerrisons to remove any osteophytes that may be present. Removal of the annulus may require the use of an annulus punch, which may be inserted through the curved portal and impacted with a mallet into the disc space. There may be use of curved curettes and curved rasps to remove the cartilaginous endplates. A rotating actuator with attached shaver blades or rotating distracter bits may be required to remove tissue.

Once the interdiscal area has been cleared of tissue, the next step is to determine the size of an implant that will be inserted between the vertebrae. One such tool to accomplish this may be an implant trial, which may be delivered into the portal and gently impacted into the disc space until the trial end is centered. Various sizes of trial implants may be provided to allow the surgeon should determine the best size for the patient. Optionally, a rotating distracter can also be used to determine implant size.

Once the surgeon has determined the proper sized implant, the next step is to insert the implant. Prior to insertion, the surgeon may choose to place graft material into the pores of the implant. The implant should be attached to an impacting inserter and the instrument/implant assembly delivered through the working portal and into the disc space. The placement of the implant can be verified using anterior-posterior and lateral fluoroscopy. Ideal implant placement is centered across the disc space from a medial-lateral perspective, and between the anterior third and middle of the disc space from and anterior-posterior perspective. Alternately, the implant can be placed between the posterior third and middle of the disc space. The implant is released from the inserter by rotating the inserter knob counterclockwise and removing the instrument from the portal. If implant repositioning or removal is desired, the inserter can be reconnected to the implant and used for repositioning or removal. The portal may then be closed using the toeing wrench to close the moveable lid of the curved portal and the portal can now be removed.

The following is a more detailed description of the exemplary interbody fusion procedure and instrumentation with regard to FIGS. 1-44c and 45-98, according to some embodiments of the present invention. In some embodiments, the present invention relates to a guided lumbar interbody fusion procedure and instrumentation.

Embodiments of the guided lumbar interbody fusion shown in FIGS. 1-44c will be discussed first, followed by additional embodiments. FIGS. 45-50b illustrate another embodiment of a system for curvilinear access to lateral spine, according to some embodiments of the present invention. FIGS. 51*a*-53*d* illustrate an exemplary guide wire delivery instrument, according to some embodiments of the present invention. FIGS. 54*a-b* illustrate another exemplary curved access portal, according to some embodiments of the present invention. FIGS. 55-72*c* illustrate additional embodiments of a guided lumbar interbody fusion systems and tools employed during a procedure performed by these systems. FIGS. 73-98 illustrate an exemplary system for curvilinear access to lateral spine of a patient, according to some embodiments of the present invention.

Embodiments Shown in FIGS. 1-44*c*

Figure 1:
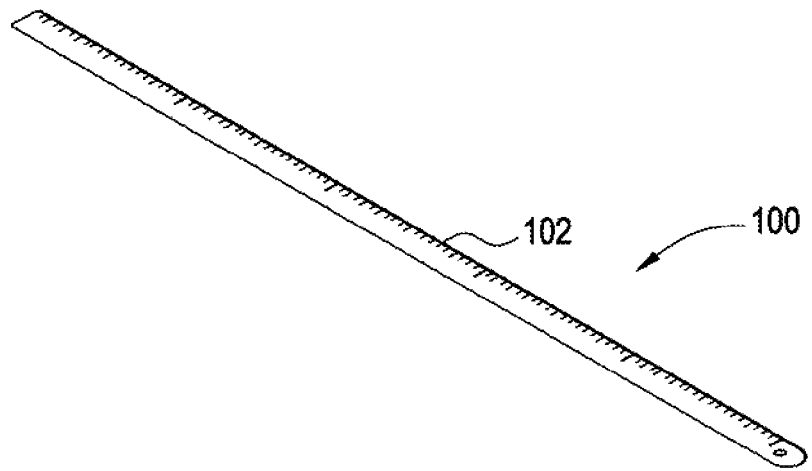
FIG. 1 illustrates an exemplary measuring device with cutout designations for locating a point of entry for delivering of instrumentation, according to some embodiments of the present invention.

FIG. 1 illustrates an exemplary measuring device 100 for locating a point of entry for delivering of instrumentation, according to some embodiments of the present invention. In some embodiments, the measuring device 100 can be a ruler. In some embodiments, the measuring device 100 can be a straight x-ray ruler with cutout designations 102 that include notches that can be seen in a fluoroscopy image.

Figure 27:
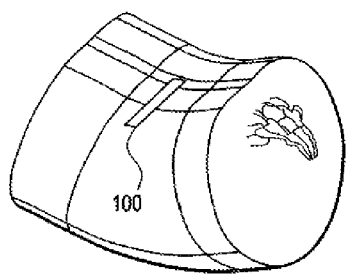
FIG. 27 illustrates an exemplary way of measurement from the midline of patient in order to locate incision, according to some embodiments of the present invention.
Figure 43:
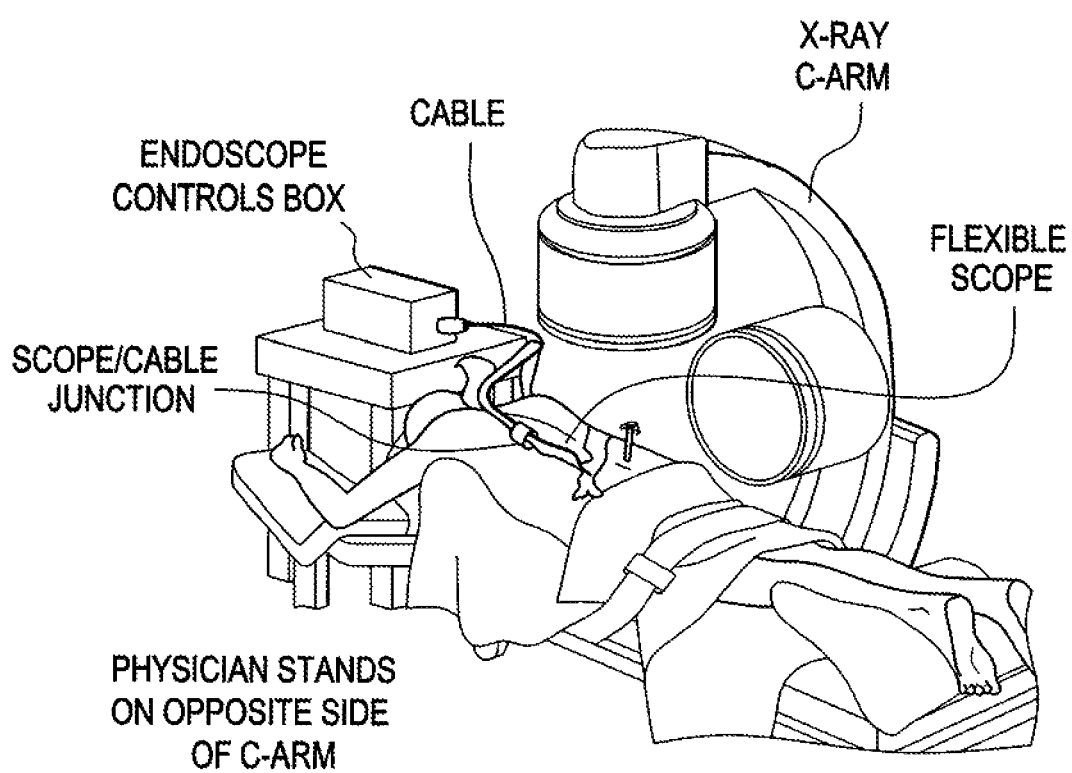
FIG. 43 illustrates a patient in a prone position for performance of the disclosed procedure, according to some embodiments of the present invention.

To perform the procedure, the patient is placed in a prone position, as illustrated in FIG. 43. Using the measuring device 100, the surgeon measures a specified distance from the midline of the back of the patient, as shown in FIG. 27. Once the measurement is made, the surgeon makes a mark using a marking device as a reference point to create an incision. In some embodiments, the incision can be about 4 to about 50 millimeters ("mm") wide. In some embodiments, the surgeon can use a chart, a sliding scale or any other methodology to determine location of the incision and the width of the incision. In some embodiments, based on this determination, the surgeon can also decide as to the angle of the portal through which the surgery will be performed.

Figure 2:
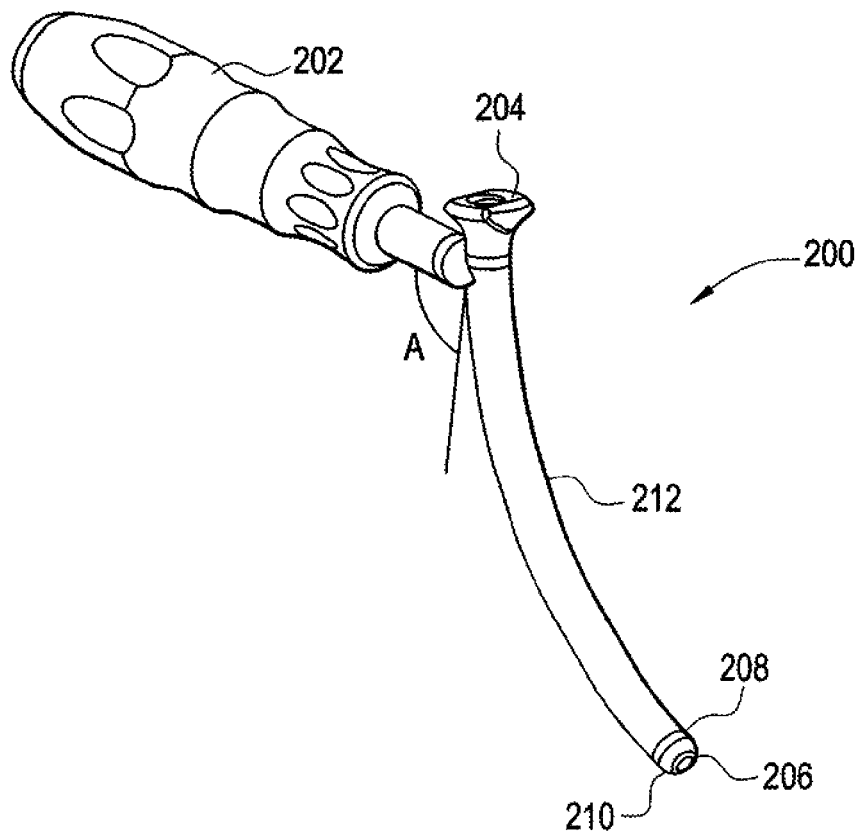
FIG. 2 illustrates an exemplary trocar guide, according to some embodiments of the present invention.
Figure 3:
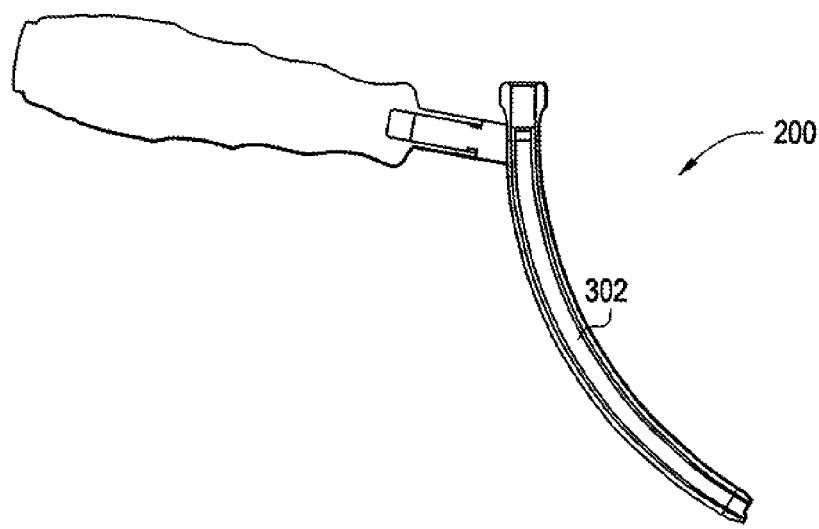
FIG. 3 is a cross-sectional view of the trocar guide shown in FIG. 2 that illustrates a curved channel for accepting a trocar or a neuro-monitoring stylette, according to some embodiments of the present invention.

FIG. 2 illustrates an exemplary trocar guide 200, according to some embodiments of the present invention. FIG. 3 is a cross-sectional view of the trocar guide 200 shown in FIG. 2 that illustrates a curved channel 302 for accepting a trocar or a neuro-monitoring stylette, according to some embodiments of the present invention. The trocar will be further discussed below with regard to FIG. 4.

During the procedure, the surgeon uses the trocar guide 200 and a dissecting finger to navigate through soft tissue, such as the fascia and psoas muscles of the patient, as shown in FIG. 28. The trocar guide 200 includes a handle 202 and a shaft 212. The shaft 212 includes a proximal end 204 and a distal end 206. The proximal end 204 includes a flat surface that the surgeon can use to hammer in the trocar guide 200. The distal end 206 further includes a tip 208 that can be configured to include a neuro-monitoring element. The distal end 206 also includes a rasping surface 210 to help anchor against lateral wall of the spine. In some embodiments, the angle A that is formed between the plane of the handle and the plane that is perpendicular to the flat surface at the proximal end 204 is approximately 100 degrees. As can be understood by one skilled in the art, angle A can have any other value. In some embodiments, the handle 202 can be manufactured from silicone and can be further configured to comfortably guide the proximal end of the instrument to the centerline of the vertebral body. As can be understood by one skilled in the art, other materials can be used for the handle 202.

The trocar guide 202 includes a channel 302 that is configured to accommodate placement of the trocar or a stylette. The channel 302 is disposed inside the shaft 202 and is configured to track the curvature of the trocar guide's shaft 202. Such curved channel 302 allows insertion of a curved trocar (as shown in FIGS. 4-5).

Figure 4:
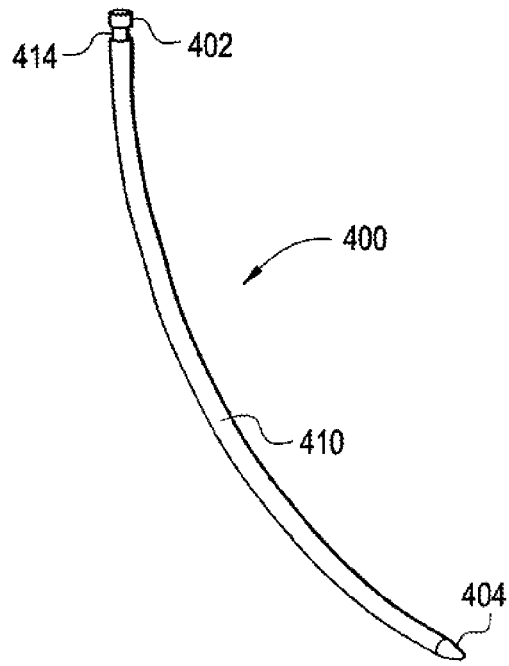
FIG. 4 illustrates an exemplary cutting trocar, according to some embodiments of the present invention.
Figure 5:
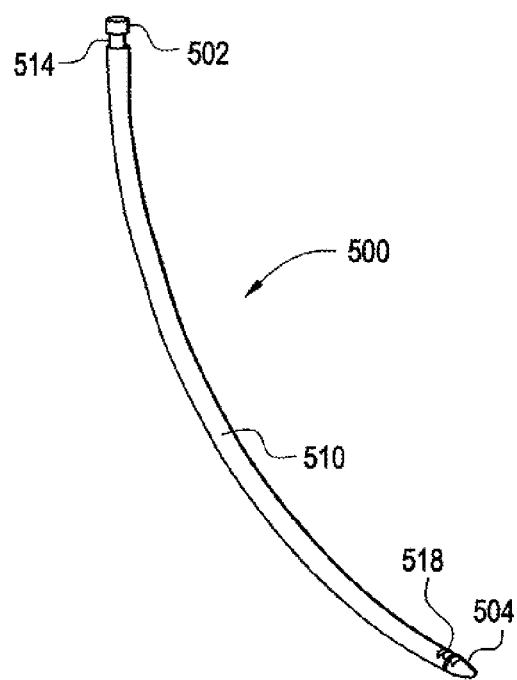
FIG. 5 illustrates an exemplary barbed/docking trocar, according to some embodiments of the present invention.

FIGS. 4-5 illustrate various exemplary trocars, according to some embodiments of the present invention.

Figure 29:
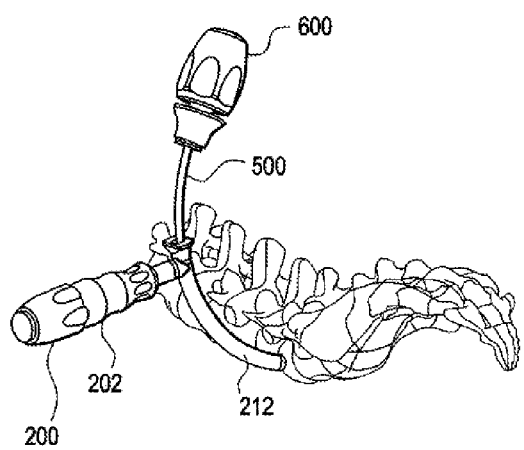
FIG. 29 illustrates the trocar with handle traveling through channel in the trocar guide, according to some embodiments of the present invention.

FIG. 4 illustrates an exemplary cutting trocar, according to some embodiments of the present invention. The cutting trocar 400 includes a distal end 402, a proximal end 404 and a shaft 410 disposed between the distal end 402 and the proximal end 404. The shaft 410 is configured to be curved in a similar fashion as the trocar guide 200. The proximal end 404 includes a pointed tip. The distal end 402 can be configured to include a grooved portion 414 that allows the handle 600 to be secured to the trocar 400. The cutting trocar 400 (shown in FIG. 4) is inserted down the trocar guide's channel 302 (shown in FIG. 3) in order to make an incision or initial punch into the vertebral wall of the patient. Then, the cutting trocar 400 is removed from the channel 302 and a barbed trocar 500 (shown in FIG. 5) is inserted, as shown in FIG. 29.

Figure 30:
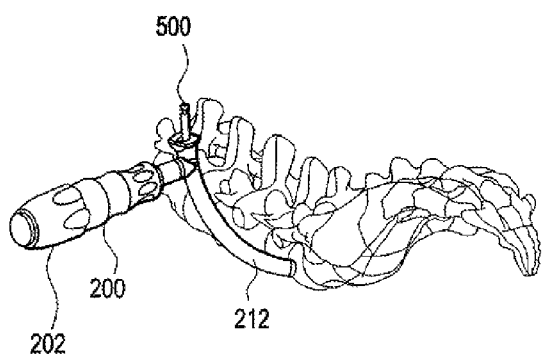
FIG. 30 illustrates the docked trocar with handle removed through trocar guide, according to some embodiments of the present invention.
Figure 31:
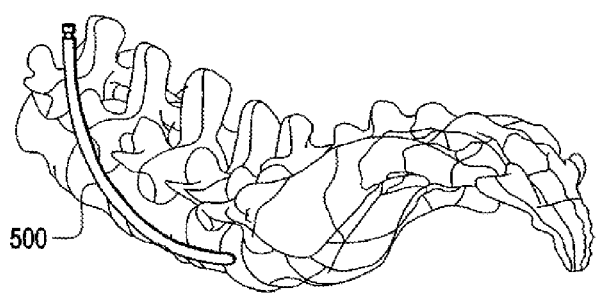
FIG. 31 illustrates the docked trocar with trocar guide removed, according to some embodiments of the present invention.

FIG. 5 illustrates an exemplary barbed/docking trocar, according to some embodiments of the present invention. The barbed trocar 500 includes a distal end 502, a proximal end 504, a shaft 510 disposed between the distal end 502 and the proximal end 504. The shaft 510 is configured to be curved in a similar fashion as the trocar guide 200. The proximal end 504 includes a pointed tip and barbs 518 that can be configured to secure the barbed trocar 500 to the spine. Similar to the trocar 400, the distal end 502 of the trocar 500 can be configured to include a grooved portion 514 that allows the handle 600 to be secured to the trocar 500. The barbed trocar is inserted down the trocar guide channel 302 (shown in FIG. 3) in order to mount to the lateral wall of the spine to provide a guide to the surgical site. Once the barbed trocar 500 is secured to the vertebral wall, a handle 600 (shown in FIGS. 6-8) is removed from the barbed trocar 500, thereby leaving the barbed trocar 500 secured to the spine, as shown in FIG. 30. The trocar guide 200 is then removed from the incision, as shown in FIG. 31.

Figure 6:
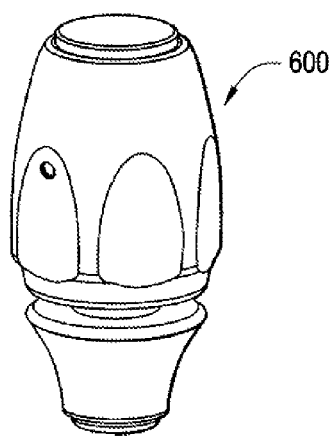
FIG. 6 illustrates an exemplary trocar handle, according to some embodiments of the present invention.
Figure 7:
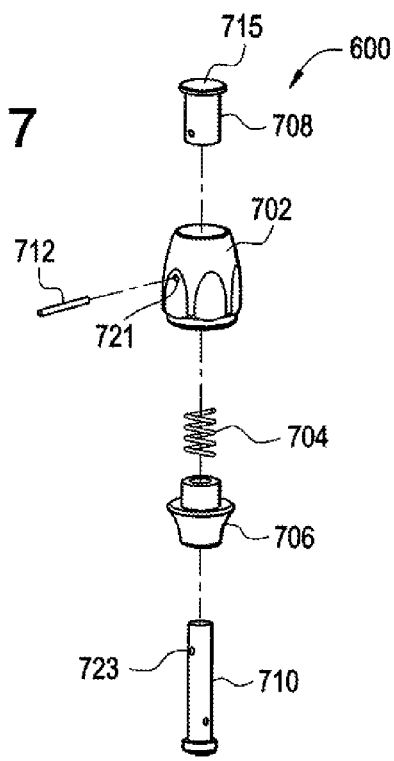
FIG. 7 is an exploded view of the trocar handle shown in FIG. 6.
Figure 8:
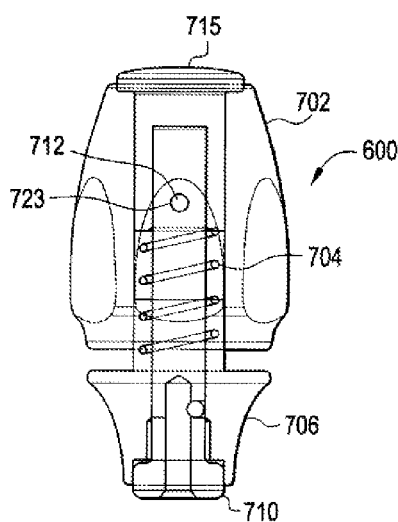
FIG. 8 is a sectional view of the trocar handle shown in FIG. 6.

FIGS. 6-8 illustrate an exemplary handle 600, according to some embodiments of the present invention. FIG. 6 illustrates the assembled trocar handle 600. FIG. 7 is an exploded view of the trocar handle shown in FIG. 6. FIG. 8 is a sectional view of the trocar handle shown in FIG. 6.

Referring to FIG. 7, the trocar handle 600 includes a handle portion 702, spring 704, bottom portion 706, a top portion 708, a shaft 710, and a locking pin 712. The handle portion 702 can be configured to be manufactured from silicon or any other suitable material(s). The top portion 708 includes a hardened surface 715. The surgeon can use surface 715 to hammer in the trocars 400 and 500. In some embodiments, the surface 715 can be manufactured from any metal or any other suitable material(s). In some embodiments, the spring 704 can be configured to control locking of the components within handle portion 702.

The handle portion 702 includes an opening 721. The shaft 710 includes an opening 723. The openings 721 and 723 are configured to be sized to accommodate insertion of the locking pin 712. The shaft 710 is configured to be inserted through the bottom portion 706, the spring 704, the handle portion 702, and the top portion 708. Once all the portions are assembled together, the locking pin 712 is inserted to secure the handle 600 together, as illustrated in FIGS. 6 and 8.

Referring to FIGS. 7 and 10, the shaft 710 of the handle 600 includes a hollow interior configured to accommodate placement of the trocar. The shaft 710 further includes a locking pin 1010 that is configured to interact with the grooves 514 of the trocar 500 and lock the trocar 500 inside the shaft 710. By squeezing the bottom portion 706, the locking pin 1010 is shifted and the trocar 500 is released from the shaft 710. As can be understood by one skilled in the art, other ways of securing the trocar 500 inside the handle 600 are possible.

Figure 9:
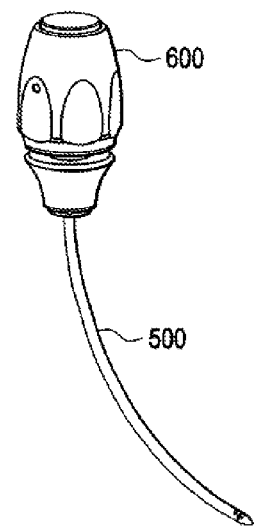
FIG. 9 illustrates the trocar handle loaded with the trocar, according to some embodiments of the present invention.

FIG. 9 illustrates the trocar handle loaded with the barbed trocar 500. FIG. 10 is detailed sectional view of the trocar 500 and trocar handle 600 interaction, according to some embodiments of the present invention. As can be understood by one skilled in the art, trocar 400 can also be loaded into the handle 600 in the same fashion as the trocar 500.

Figure 32:
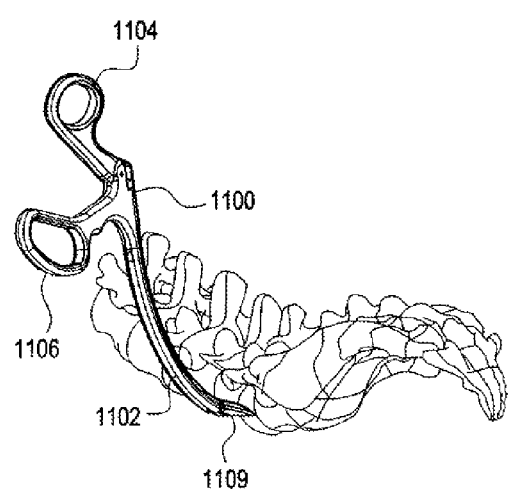
FIG. 32 illustrates the tissue separator traveling the length of the trocar to an operating site, where the tear drop end will sweep approximately 12 mm above and below trocar, according to some embodiments of the present invention.

FIGS. 11-14 illustrate an exemplary tissue separator 1100, according to some embodiments of the present invention. FIG. 11 is a general view of the tissue separator 1100. FIG. 12 illustrates exemplary working aspects of the tissue separator 1100, according to some embodiments of the present invention. FIG. 13 illustrates the tear-drop working end geometry of the tissue separator 1100. FIG. 14 illustrates an exemplary trocar channel cutout 1402 on the underside of the tissue separator 1100. The tissue separator 1100 is guided down the barbed trocar 500 (shown in FIG. 5) to the vertebral wall and is actuated to separate tissue from the vertebral wall, as illustrated in FIG. 32. The trocar channel cutout on the underside of the tissue separator can be used to aid in guiding the tissue separator down the barbed trocar. In some embodiments, the tissue can be separated above the trocar and then separated below the trocar.

The tissue separator 1100 includes a shaft 1102, handles 1104, 1106, distal portion 1108 have separators 1109a and 1109b. The handles 1104, 1106 are hingedly coupled to the shaft 1102 at the pivotal connection 1120. The handles 1104, 1106 are configured to control movement of the separators 1109a, 1109b. The shaft 1102 is configured to have a similar curved geometry as the trocar guide 200, as shown in FIG. 2. The separators 1109 (a, b) are configured to remove or peel tissue at the location of the docked barbed trocar 500 (shown in FIG. 5). Such removal is possible through up and down pivotal movement B as illustrated in FIG. 12. In some embodiments, the movement B is possible through rotational motion of the handles 1104, 1106 in a scissor like fashion. In some embodiments, one of the handles 1104, 1106 (e.g., 1106) can be fixedly secured to the shaft 1102, whereas the other handle (e.g., 1104) can be configured to rotate. Those skilled in the art will recognize that other actuation methods for this device can be used.

In some embodiments, the distance between separators 1109a and 1109b can be configured to accommodate the diameter of the trocar 500. The tissue separator 1100 can be configured to be slid down the trocar 500 using channel 1402 (illustrated in FIG. 14). The channel 1402 is configured to be disposed on the back side of the tissue separator 1100 and allows the surgeon to guide the tissue separator 1100 to remove tissue(s) surrounding the trocar 500. The removal is accomplished through pivotal movement of the separators 1109(a, b). In exemplary embodiments of spinal surgery procedures, the tissue separator 1100 can be used to separate psoas muscle tissue. As can be understood by one skilled in the art, the separator 1100 can be used for any other tissue separation and/or removal.

FIG. 15 illustrates an exemplary anterior tissue distracter 1502 and dorsal tissue distracter 1504, according to some embodiments of the present invention. FIG. 16 illustrates an exemplary assembly of a neuro monitoring ribbon 1602 installed on the dorsal tissue distracter 1504, according to some embodiments of the present invention. The distracters can be also referred to as distraction ramps. In some embodiments, the distracters can be delivered as a single unit along the inserted barbed trocar 500 (shown in FIG. 5), where the trocar 500 is placed between the distracters, to the vertebral wall. In some embodiments, the distraction ramps 1502, 1504 are delivered together as a single unit in a balloon, which keeps the ramps joined and prevents encroachment of soft tissue between the ramps.

Referring to FIG. 15, the ramp 1504 will be discussed. The structure of the ramp 1502 is similar to the ramp 1504. The ramp 1504 includes a proximal end 1511 and a distal end 1513. The ramp 1504 further includes a rail/slot (shown as rail/slot 1506 on ramp 1502). The rail/slot 1506 is configured to be disposed on the interior side of the ramps 1502 and 1504 and further configured to accommodate guiding of instruments (such as trocars or dilators) down to the procedure working area at the surgical site. The rail/slot on each ramp is disposed between the proximal and distal ends and is further configured to create openings 1530 at the proximal end 1511 (formed by two rail/slot portions 1530a and 1530b) and 1531 (formed by two portions 1531a and 1531b) at the distal end 1508 of the ramps, when the ramps' interior sides are joined together. As stated above, such openings are configured to accommodate placement of instruments between the ramps.

At the distal end 1508, the ramp 1504 further includes a lip 1513 (the ramp 1502 includes a lip 1510) that is configured to help navigate through the soft tissue and "grab" the tissue. As the ramps are guided down the barbed trocar 500, the lip 1513 (and/or lip 1510) on the ramp are configured to push away the tissue allowing the ramps to approach the wall of the vertebral disc. In some embodiments, the ramps include a monitoring element 1602 disposed on the ramp 1504 (also referred to as a dorsal ramp), as illustrated in FIG. 16. In some embodiments, the monitoring element 1602 can be configured to be any conventional neural monitoring element that allows detection of approaching neural tissue via application of current. In some embodiments, the element 1602 can be configured to be coupled to an electrical supply (not shown) that delivers current to the tissue via element 1602 and upon detection of a response, the element 1602 can determine whether neural tissue is proximate to the element 1602 and/or the ramp 1504 (and/or 1502). Further, the neuron-monitoring element 1602 can be used to preserve the integrity of neural structures and provide an early detection to prevent or minimize damage to those structures during surgical procedures. As can be understood by one skilled in the art, both ramps 1502 and 1504 can be configured to include element 1602.

Figure 17:
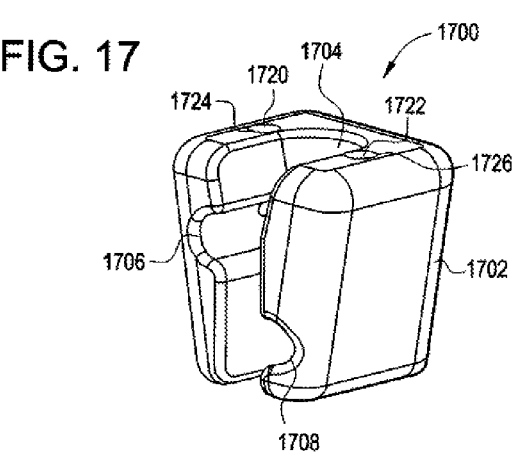
FIG. 17 illustrates an exemplary tissue distracter alignment block, according to some embodiments of the present invention.
Figure 18:
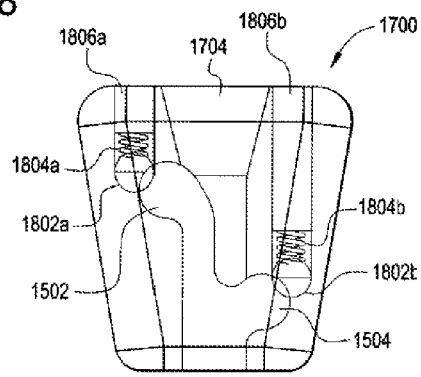
FIG. 18 illustrates an exemplary cutout for receiving tissue distracters and exemplary internal components of a spring ball detents that lock the tissue distracters, according to some embodiments of the present invention.
Figure 19:
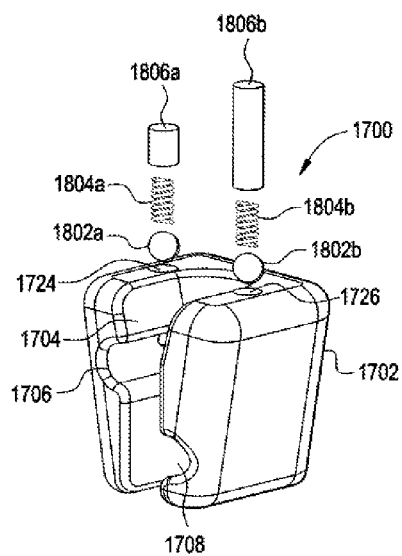
FIG. 19 is an exploded view of the tissue distracter alignment block, according to some embodiments of the present invention.
Figure 20:
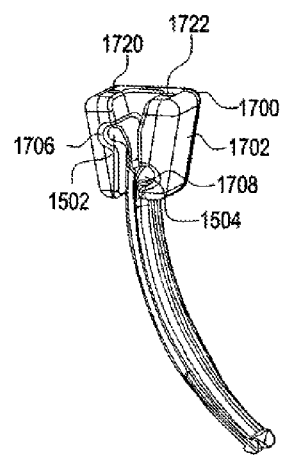
FIG. 20 illustrates an exemplary way of fitting the tissue distracters inside the alignment block, according to some embodiments of the present invention.
Figure 33:
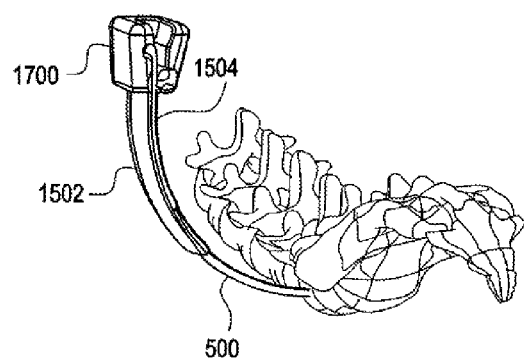
FIG. 33 illustrates tissue distracters with alignment block traveling the length of the trocar to the operating site, according to some embodiments of the present invention.

In some embodiments, the distraction ramps 1502 and 1504 can have variable lengths and a distracter alignment block 1700, illustrated in FIG. 17, can be used to align the ramps 1502 and 1504 for proper insertion and approach to the surgical site (as shown in FIG. 33). FIGS. 18-20 are various views of the distracter alignment block 1700. FIG. 18 is a cross-sectional view of the block 1700 showing tissue distracters and internal components of block 1700 that include a spring ball detents that lock the tissue distracters, according to some embodiments of the present invention. FIG. 19 is an exploded view of the tissue distracter alignment block 1700. FIG. 20 illustrates an exemplary way of fitting the tissue distracters inside the alignment block 1700.

Referring to FIG. 17, block 1700 includes a housing 1702 having an open channel 1704 disposed inside the housing 1702. The open channel 1704 is further configured to be disposed between the top and the bottom of the housing 1702. The channel 1704 includes grooves 1706 and 1708 disposed on each side of the open channel 1704, as shown in FIG. 17. The grooves 1706 and 1708 are configured to accommodate placement of the proximal ends of the distraction ramps 1502 and 1504, respectively. Referring to FIGS. 15 and 17, the proximal ends of the ramps 1502, 1504 include protruding portions that are configured to be curved away from their interior portions and are sized to fit inside the open channel 1704 and the grooves 1706 and 1708, respectively. In some embodiments, the ramps 1502, 1504 can be configured to be inserted into the channel 1704 simultaneously or one after the other. Since, the channel 1704 is open on one side of the housing 1702 and closed on the other side of the housing 1702, the ramps 1502, 1504 are prevented from sliding out after being inserted into the grooves 1706, 1708. To further prevent the ramps 1502, 1504 from sliding out the open side of the channel 1704, locking mechanisms 1720, 1722, respectively. The locking mechanisms 1720, 1722 are configured to be disposed within the openings/holes 1724, 1726, respectively, which are further accessible through the top of the housing 1702 of the block 1700, as illustrated in FIG. 17.

Figure 34:
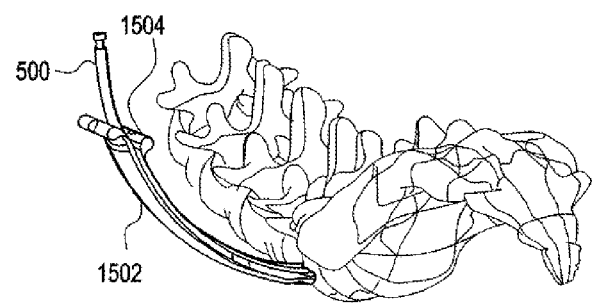
FIG. 34 illustrates tissue distracters being fully inserted, according to some embodiments of the present invention.

Referring to FIGS. 18 and 19, the locking mechanisms 1720, 1722 are illustrated in further detail. Each one of the locking mechanisms 1720, 1722 includes a ball 1802 (*a, b*), a spring 1804 (*a, b*), and a locking pin 1806 (*a, b*). The balls 1802 are configured to be inserted first into the openings 1724, 1726, followed by the spring 1804, and then pins 1806. In some embodiments, the pin 1806*a* is configured to be shorter than the pin 1806*b* since the groove 1708 is disposed lower than the groove 1706 along the open channel 1704. The pins 1806 can further include a locking device that prevents the pins from accidentally falling out of the openings 1724, 1726. Upon insertion of the balls 1802, springs 1804, and pins 1806 into the openings 1724, 1726, respectively, and insertion of the ramps 1502, 1504 into the grooves 1706, 1708, respectively, the balls 1802 upon being pushed by the pins 1806 via springs 1804, push on the protrusions of the ramps 1502, 1504, which secures the ramps 1502, 1504 inside the grooves 1706, 1708. This locking arrangement prevents accidental slippage of the ramps 1502, 1504 and allows proper insertion and advancement of the ramps toward the vertebral wall of the disc. FIG. 20 illustrates the ramps 1502, 1504 being secured inside the alignment block 1700. In some embodiments, the channel 1704, disposed on the interior portion of the housing 1702, is configured to be wider near the top of the housing 1702 and narrower near the bottom of the housing 1702, as illustrated in FIG. 20. This allows to further secure the ramps 1502, 1504 inside the housing 1702. Once the ramps are advanced toward the surgical site, the alignment block can be removed to allow tissue distraction, which can be accomplished using distraction ramps 1502, 1504, and insertion of dilators (discussed below with regard to FIGS. 21-22), as shown in FIG. 34.

Figure 21:
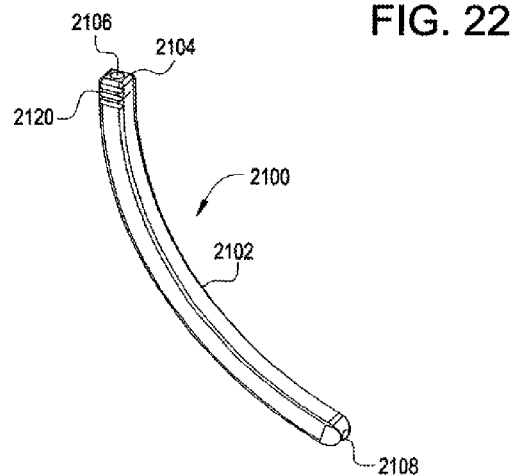
FIG. 21 illustrates an exemplary small dilator, according to some embodiments of the present invention.
Figure 22:
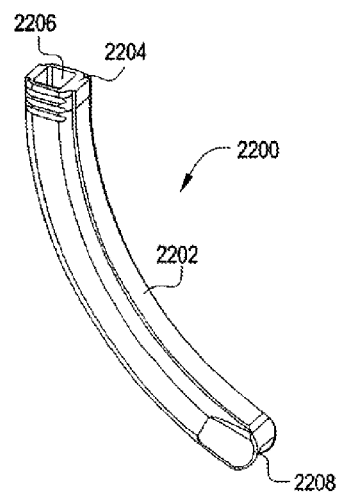
FIG. 22 an exemplary large dilator, according to some embodiments of the present invention.

FIGS. 21-22 illustrate exemplary dilators that are configured to be guided down the barbed trocar 500 (shown in FIG. 5) and between distraction ramps 1502, 1504 using rail/slot 1506. FIG. 21 illustrates an exemplary small dilator 2100, according to some embodiments of the present invention. FIG. 22 an exemplary large dilator 2200, according to some embodiments of the present invention. In some embodiments, the small dilator 2100 is initially guided down over the barbed trocar 500 (shown in FIG. 5) and between the distraction ramps 1502, 1504. Then, the large dilator 2200 is guided down over the small dilator 2100 and also between the distraction ramps 1502, 1504.

Both dilators 2100 and 2200 are further configured to be curved in a similar fashion as the trocar 500 (shown in FIG. 5). The curvature radius of the trocar 500, dilators 2100, 2200, and other instruments discussed in the present application are configured to substantially match in order to prevent wobbling of these instruments when they are being advanced toward the surgical site. In some embodiments, the dilator 2200 can be shorter than the dilator 2100, which can further accommodate placement and removal of the dilators. The dilators can be manufactured from any biocompatible material such as, but not limited to stainless steel, titanium, aluminum, and/or polyetheretherketone ("PEEK"). In some embodiments, the material can be also non-conductive radiolucent material, and can be hammered with a mallet to advance it to the surgical site.

Figure 35:
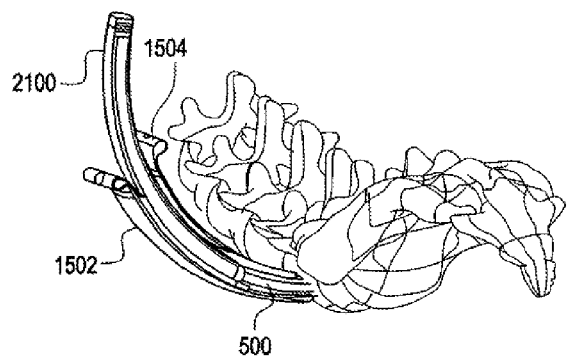
FIG. 35 illustrates the small dilator spreading the tissue distracters, according to some embodiments of the present invention.

Referring to FIG. 21, small dilator 2100 includes a housing 2102 having an open channel 2104. The channel 2104 is sized to accommodate insertion of the trocar 500. The channel 2104 is disposed throughout the interior of the housing 2102 and begins with an opening 2106 at the top (or near the proximal end) of the dilator 2100 and ends with an opening 2108 at the bottom (or near the distal end) of the dilator 2100. The dilator 2100 is configured to be placed over the trocar 500 (shown in FIG. 5) with the opening 2108 and then slid down the trocar 500 until the dilator 2100 reaches the surgical site, as shown in FIG. 35. The housing 2102 of the dilator 2100 further includes a plurality of grasping ribs 2120 disposed near the proximal end of the dilator. The grasping ribs 2120 are further configured to allow holding the dilator 2100 when the dilator is being slid down the trocar 500. As illustrated in FIG. 21, the channel 2104 has a round cross-section in order to accommodate placement of the trocar 500. Further, the dilator 2100 has a square cross-section. As can be understood by one skilled in the art, the cross-sections of the channel 2104 and the dilator 2100 can vary as desired.

Figure 36:
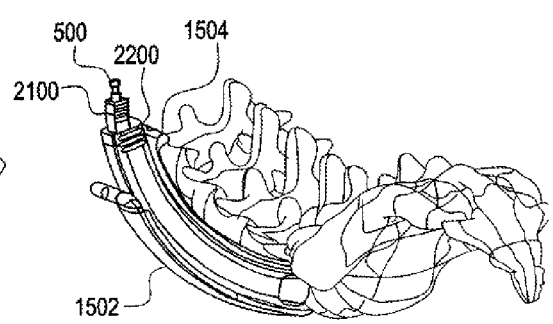
FIG. 36 illustrates the large dilator spreading the tissue distracters over the small dilator, according to some embodiments of the present invention.
Figure 40:
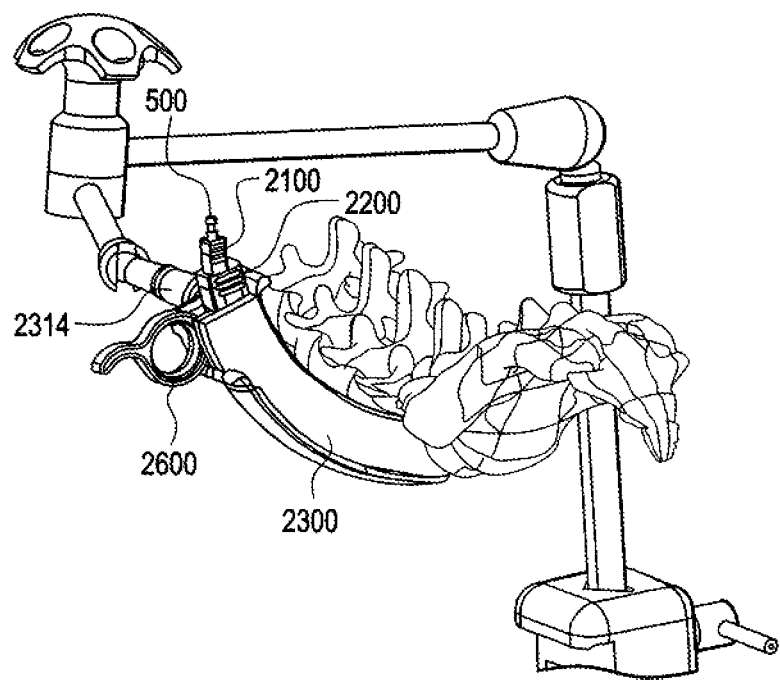
FIG. 40 illustrates an exemplary stabilization arm being mounted to the portal, according to some embodiments of the present invention.

Referring to FIG. 22, large dilator 2200 includes a housing 2202 having an open rail/slot 2204. The rail/slot 2204 is sized to accommodate insertion of the small dilator 2100. The rail/slot 2204 is disposed throughout the exterior of the housing 2202 and begins with an opening 2206 at the top (or near the proximal end) of the dilator 2200 and ends with an opening 2208 at the bottom (or near the distal end) of the dilator 2200. The dilator 2200 is configured to be placed over the dilator 2100 (shown in FIG. 21) with the opening 2208 and then slid down the dilator 2100 until the dilator 2200 reaches the surgical site, as shown in FIG. 36. The housing 2202 of the dilator 2200 further includes a plurality of grasping ribs 2220 disposed near the proximal end of the dilator. The grasping ribs 2220 are further configured to allow holding the dilator 2200 when the dilator is being slid down the small dilator 2100. As illustrated in FIG. 22, the rail/slot 2204 has a square rail/slot cross-section in order to accommodate placement of the small dilator 2100. Further, the dilator 2200 has a square cross-section. As can be understood by one skilled in the art, the cross-sections of the rail/slot 2204 and the dilator 2200 can vary as desired.

Figure 23:
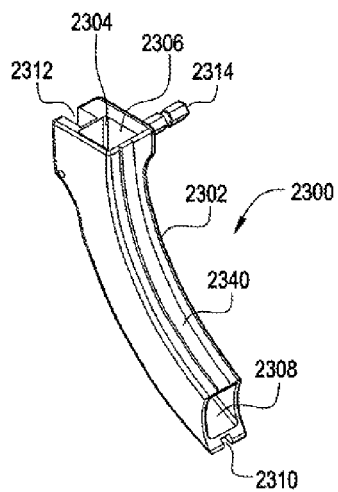
FIG. 23 an exemplary curved portal, according to some embodiments of the present invention.
Figure 24:
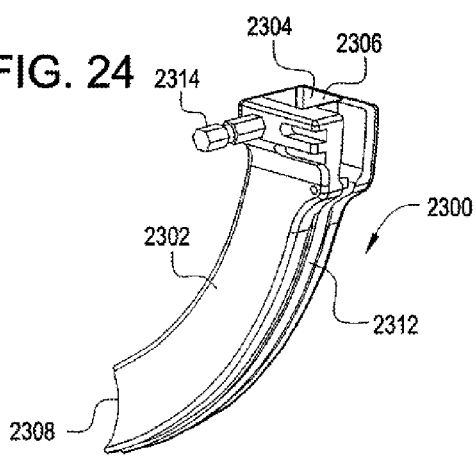
FIG. 24 is another view of the curved portal shown in FIG. 23.
Figure 25:
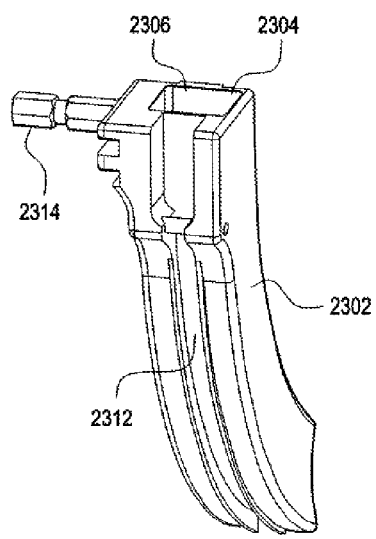
FIG. 25 is a rear view of the curved portal shown in FIG. 23.

FIGS. 23-25 illustrate an exemplary curved portal 2300, according to some embodiments of the present invention. FIG. 23 illustrates the curved portal 2300. FIG. 24 is another view of the curved portal 2300. FIG. 25 is a rear view of the curved portal 2300.

As illustrated in FIGS. 23-25, the portal 2300 includes a housing 2302 disposed between the proximal end 2306 and a distal end 2308. The housing 2302 also includes an interior channel 2304 that is disposed between an opening at the proximal end 2306 and an opening at the distal end 2308. The channel 2304 is sized to accommodate insertion over the large dilator 2200 (shown in FIG. 22) and subsequent instrumentation. Channel 2304 may contain additional rail/slots to aid in guiding instrumentation. The housing 2302 also includes an outside rail/slot 2312 disposed on the rear portion of the working portal 2300, as illustrated in FIGS. 23-25. The rail/slot 2312 is configured to extend through the whole housing 2302 and terminate at the distal end 2308 at an opening 2310. The opening 2310 is further configured to accommodate protrusion of an awl 2600 (shown in FIG. 26) upon its insertion through the rail/slot 2312. The outside rail/slot 2312 and 2340 are configured to accommodate insertion of the working portal 2300 between tissue distracters 1502 and 1504. The outside rail/slot 2312 is also disposed between the proximal end 2306 and the distal end 2308. The distal end 2308 has a curved open end structure that can be configured to accommodate mounting to the lateral wall of the spine.

In some embodiments, the width and/or height of the working portal 2300 can be in the range of 5 mm to 30 mm; alternately, between 10 mm and 25 mm; alternately, between 15 mm and 25 min; alternately, between 18 mm and 23 mm. In some embodiments, the width of the working portal 2300 can be 20.3 mm. In some embodiments, the height of the portal 2300 can be 24 mm. In some embodiments, the width and/or height of the channel 2304 can be in the range of 5 mm to 30 mm; alternately, between 10 mm and 25 mm; alternately, between 15 mm and 25 mm; alternately, between 18 mm and 23 mm. In some embodiments, the width of the channel 2304 can be 17 mm. In some embodiments, the height of the channel 2304 can be 19 mm. The curvature radius of the working portal 2300 can be in above 3 mm. In some embodiments, the curvature radius of the working portal 2300 can be very large, thereby the working portal 2300 having only a slightly curved shape. In some embodiments, the curvature radius of the working portal 2300 is 12 cm.

Figure 44A:
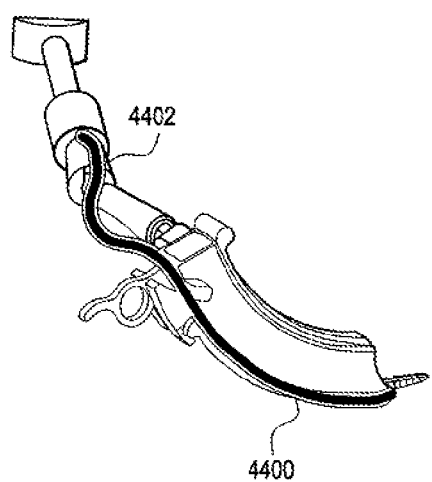
FIGS. 44*a*-*c* illustrate an exemplary working portal with an endoscope, displaying the endoscope's field of view, according to some embodiments of the present invention.
Figure 44B:
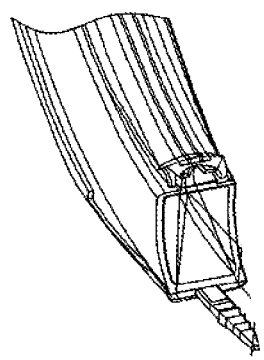
Figure 44C:
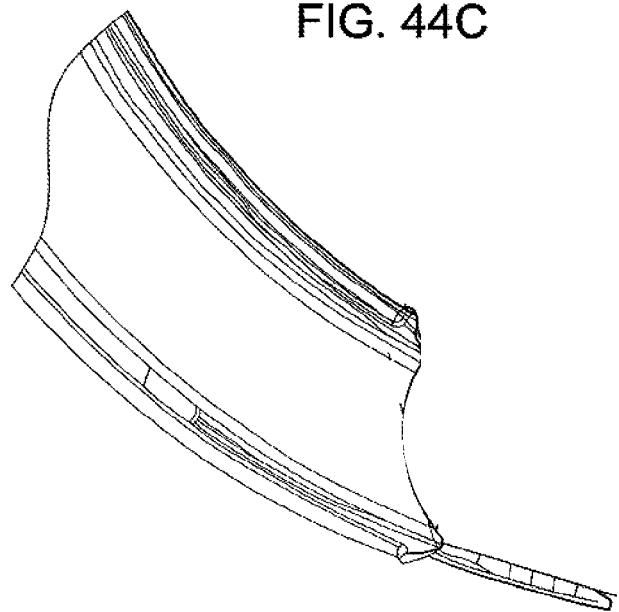

In some embodiments, the working portal 2300 can also accommodate placement of an endoscope 4400 that allows viewing of the surgical area, as illustrated in FIG. 44a-c. Direct visualization is via a flexible or fixed radius endoscope. Intra-operative electrophysiological monitoring and fluoroscopy are utilized. The endoscope 4400 can be disposed along one of the walls of the working portal 2300, as shown in FIG. 44a, and can be mounted on the holding arm 4402 that secures the working portal 2300. As illustrated in FIGS. 44b-c, the endoscope viewing area can be on the order of about 50.8 mm by 15.875 mm by 28.575 mm. FIG. 44c illustrates the field of view of the endoscope.

Referring back to FIGS. 23-25, the working portal 2300 can be configured to have a substantially square or rectangular cross-section. As can be understood by one skilled in the art, the cross-section of the working portal 2300 can have any other shape, e.g., elliptical, round, polygonal, or any other desired shape. Because of the curvature of the working portal 2300, it can accommodate insertion of an implant at a direction that is substantially perpendicular to the surface of the body of the patient. Once the implant is inserted at the proximal end of the working portal 2300, it is advanced toward the surgical site down the interior channel of the working portal 2300. Upon approaching the surgical site, the direction of movement of the implant changes from substantially perpendicular or angular with regard to the body of the patient to substantially lateral or transverse. This allows the surgeon easily manipulate insertion and placement of the implant without having to create a large incision in the patient. The working portal 2300 can be configured to accommodate insertion of an implant having the following dimensions: height in the range of 8 mm to 18 mm, an anterior-posterior depth of in the range of 8 mm to 30 mm (alternately, between 10 mm to 25 mm; alternately, between 15 mm to 25 mm; alternately, between 18 mm to 23 mm; in some embodiments, the depth can be approximately 22 mm), and a lateral width in the range of 20 mm to 70 mm (alternately, between 30 mm to 65 mm; alternately, between 40 mm to 50 mm; alternately, between 45 mm to 55 mm).

In some embodiments, the working portal 2300 can be manufactured from any biocompatible material such as, but not limited to stainless steel, titanium, aluminum, and/or PEEK. As can be understood by one skilled in the art, the portal 2300 can be manufactured from any other suitable material(s).

Once the portal 2300 is satisfactorily located and its location is verified via x-ray (or any other means), an anterior awl 2600 can be inserted within outer slot/rail 2312 to secure the working portal 2300 to the spine. FIG. 37 illustrates the portal 2300 prior to insertion of anterior awl 2600. As shown in FIG. 37, along with the portal 2300, the trocar 500, the dilators 2100 and 2200, and the ramps 1502 and 1504 are also inserted. The awl 2600 contains a handle configured to protrude away from the distal end 2308 of the portal 2300 (as shown in FIGS. 38-39).

Figure 26:
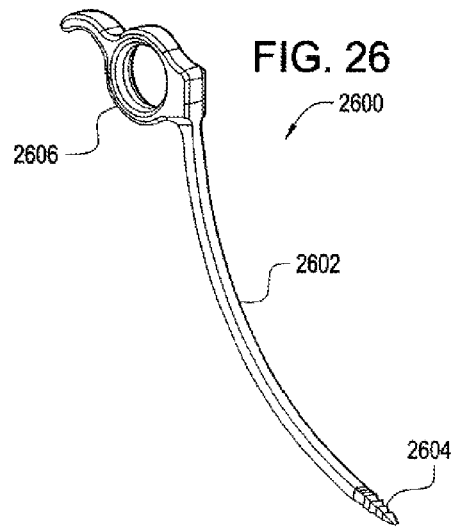
FIG. 26 illustrates an exemplary anterior awl, according to some embodiments of the present invention.

Referring to FIG. 26, the awl 2600 includes a curved shaft 2602 disposed between a handle 2606 at the proximal end of the awl 2600 and a barbed tip 2604 at the distal end of the awl 2600. The barbed tip 2604 is configured to make an incision in the vertebral wall. The shaft 2602 is configured to be curved in a similar fashion as other instruments (e.g., the trocars, dilators, etc.) in order to allow adequate advancement of the awl 2600 towards the surgical site. In some embodiments, the awl 2600 is manufactured from any biocompatible material such as, but not limited to stainless steel, titanium, aluminum, and/or PEEK. In some embodiments, the material can be also a radio-opaque material. As can be understood by one skilled in the art, the awl 2600 can be manufactured from any other suitable materials.

Figure 41:
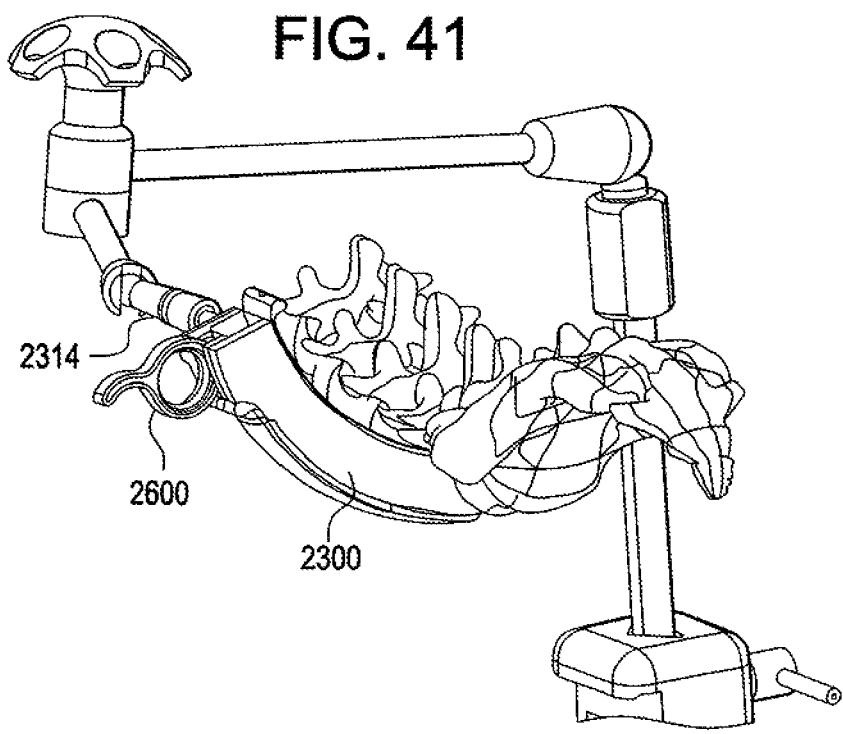
FIG. 41 illustrates an exemplary portal assembly with dilators and trocar being removed, according to some embodiments of the present invention.
Figure 42:
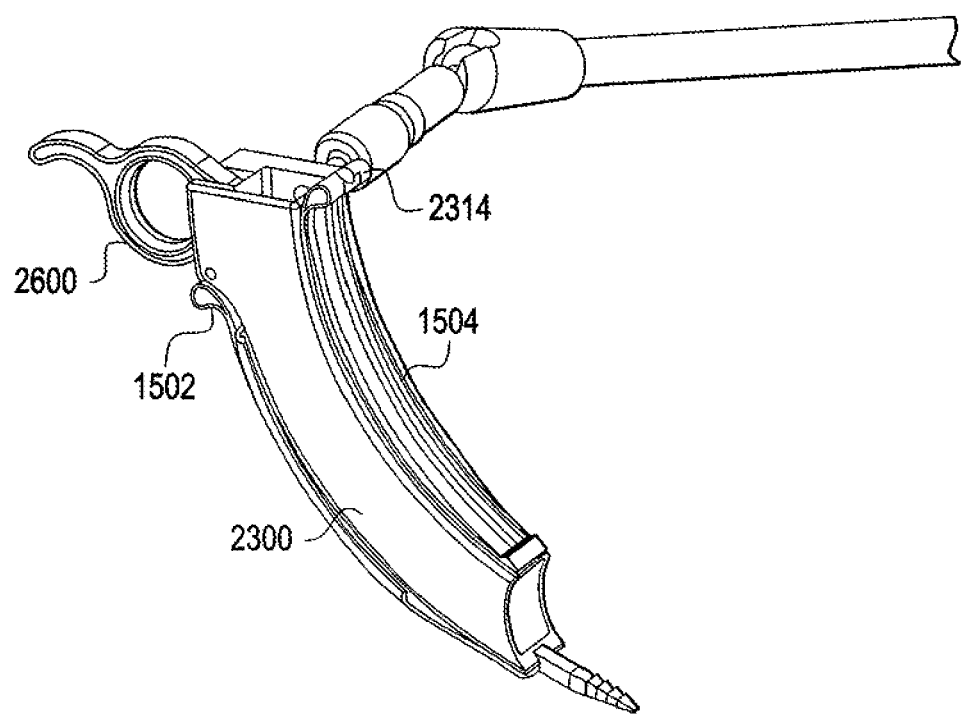
FIG. 42 illustrates an exemplary final portal assembly and a protrusion of the anterior awl, according to some embodiments of the present invention.

The working portal construct can be further stabilized using a stabilization arm 2314 (e.g., StrongArm, manufactured by Mediflex). The arm 2314 is coupled to stationary equipment in the operating room, such as the operating table. As can be understood by one skilled in the art, any other holding arms can be used. Once the portal is docked using the anterior awl and stabilization arm, the dilators 2100, 2200 and the trocar 500 are removed, thereby leaving the working portal 2300 and the barbed awl 2600 allowing the surgeon to perform desired procedures (e.g., delivery of an implant), as shown in FIGS. 41-42.

Embodiments Shown in FIGS. 45-98

FIGS. 45-50b illustrate an exemplary system 4500 for curvilinear access to lateral spine 4502 of a patient, according to some embodiments of the present invention. The system 4500 includes a curvilinear access device or portal 4510 through which various surgical instruments can be delivered to the lateral spine 4502. In some embodiments, the portal 4510 can be supported using a holding arm assembly 4515. The holding arm assembly 4515 can have various stationary and movable portions that allow the surgeon (or other medical professional) to properly secure the portal 4510. As described above with regard to FIGS. 1-44c, the patient is typically placed in a prone position (such as shown in FIG. 43) and the portal 4510 is secured to patient's lateral spine using the assembly 4515. One embodiment of the portal 4510 is illustrated in FIGS. 46a-50b.

One embodiment of the presented invention, as shown in FIGS. 45-50b, is a curvilinear portal 4510 for accessing the lateral spine. Portal includes a movable top 4612 to allow direct visualization of the surgical site through the expandable working port and works in conjunction with delivery instrumentation to help safely guide the portal to a surgical site and to minimize tissue disruption when fully installed. Additional features include distal fixation via an anterior awl and a proximal fixation via an attachment, such as a hex attachment, which interfaces with a surgical table stabilization arm.

The present invention allows curved access to the spine while the patient is in the prone position having the following advantages over traditional lumbar interbody fusion: adding posterior fixation without rotating patient, minimizing nerve compression against TP compared to a straight oblique approach, delivering an implant with better anatomic physiology without requiring drastic repositioning (like TLIF req.), protecting anterior aspect, preserving posterior elements and protecting the bowels from injury. The movable top further allows direct visualization through the working port, allowing the surgeons to confirm anatomy and ensure soft tissue is protected.

FIG. 46a illustrates the portal 4510 in further detail. The portal 4510 includes a portal slide 4610, a movable top 4612 having two movable portions 4611 and 4613, a nerve root retracting tongue 4614, a push button 4616 for movable top 4612, an anterior awl 4618, and a pull handle 4620. In some embodiments, the portal slide comprises a working portal housing having a channel with an open top. The moveable top and portal slide may be made from metal, plastic, polymer, polyetheretherketone ("PEEK") or other suitable material.

The movable top 4612 can be any variety of movable tops, including a movable top (an exemplary embodiment of such movable top will be discussed below for illustrative purposes only), rollable top (whereby the top or any portion of it is configured to roll up to one of the ends of the portal slide), or any other cover mechanism that can be configured to be moved to provide an enlarged working portal between the portal slide 4612 and the movable top 4612 and provide a clear line of sight for the surgeons (or other medical professionals). In some embodiments, the movable top is configured to be convertible and can be made from an elastic material having cables threaded from the proximal end to the distal end (or vice versa), and is configured to retract in fashion similar to a mini-blind. Other embodiments may include tension with a pliable material or cable-like element that may be used to open the top, or a static slide may be placed post-insertion The movable top 4612 is pivotally secured to the portal slide 4610 in at least two locations: one near the distal end of the slide 4610 (i.e., away from the lateral spine (not shown)) and the other near the proximal end of the slide 4610 (i.e., substantially near the lateral spine (not shown)). As stated above, the movable top 4612 includes two portions: a distal portion 4611 and a proximal portion 4613. The distal portion 4611 and a proximal portion 4613 are pivotally secured to one another and to the slide 4610 near its distal end and proximal end, respectively. The distal portion 4611 and a proximal portion 4613 are configured to move or pivot into and out of the open top of the slide's channel, i.e., between closed and open positions. FIG. 46b illustrates the portal 4510 being in a closed position, where the movable top 4612 is configured to be pushed into the channel of the portal slide 4610. In this position or closed configuration, the top blocks direct visualization between the proximal end and the distal end of the slide 4610. FIG. 46c illustrates the portal 4510 being in an open position or open configuration, whereby the movable top 4612 is configured to be pulled out or moved away from the channel of the slide 4610. As illustrated in the FIGS. 45-50b, the movable top 4612 is configured to provide a clear line of sight to the surgical site in an open position, whereas, in a closed position, the movable top 4612 is configured to create a curved or a substantially convex shaped structure, blocking the clear line of sight. As can be understood by one skilled in the art, the movable top 4612 along with its portions 4611, 4613 (or any number of such portions) can be coupled to each other and/or portal slide 4610 via any means including but not limited to hinges, pivots, bolts, screws, wires, strings, extension arms, or others. As can be further understood by one skilled in the art, the movable top 4612 and/or any of its portions can be manufactured from any number of materials, including but not limited to, metal, plastic, polymers, or others.

The push buttons 4616 (as shown in FIG. 46d, there can be more than one button 4616) can be configured to open and close the movable top 4612. Upon pressing the buttons 4616, the movable top can be opened (as shown in FIG. 46c) or closed (as shown in FIG. 46b).

In some embodiments, the pull handle 4620 can be configured to assist the surgeon (or any other medical professional) with opening and closing the movable top 4612. To open the movable top 4612, the surgeon can pull the pull handle 4620 while pressing the buttons 4616. To close the top, the surgeon can push the pull handle 4620 and simultaneously press the push buttons 4616. The movable top 4612 is configured to automatically extend away from the interior portion of the slide 4610 to open up the slide or retract back into the interior portion of the slide 4610 to close the slide.

The anterior awl 4618 is further described with regard to FIGS. 47a-47d and is configured to provide a locking mechanism to the portal 4510.

Figures 47A, 47B:
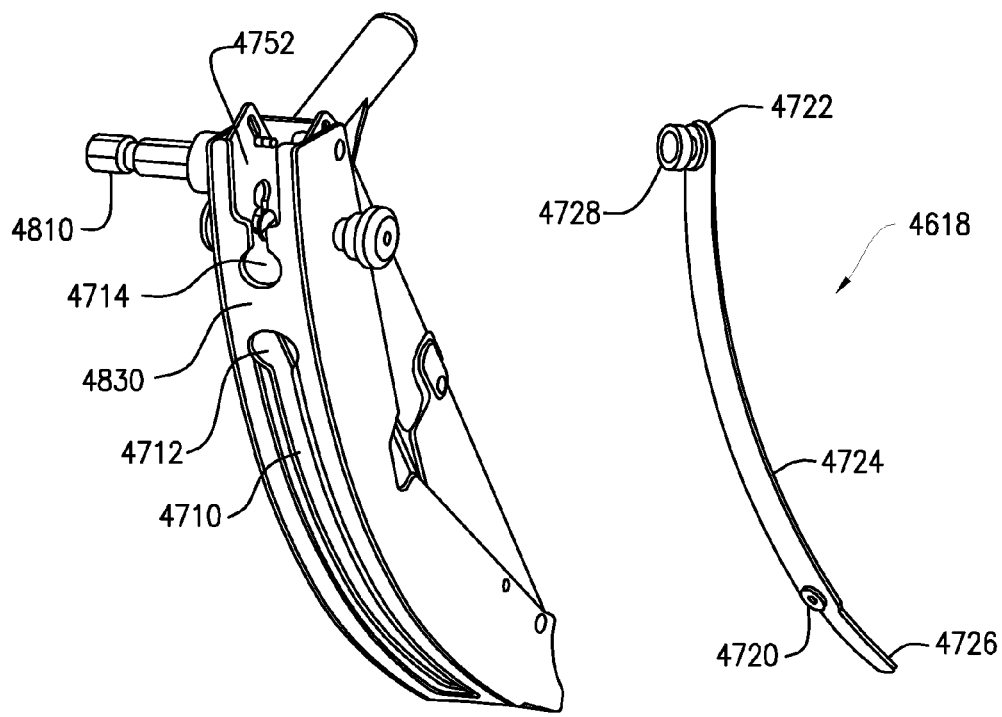

FIGS. 47a-47d illustrate use of the anterior awl 4618 in connection with the portal 4510. FIG. 47a is a rear view of the portal 4510. The back portion 4830 of the portal slide 4610 includes a grooved anterior awl channel/slot 4710, a guide pin hole 4712, and a locking hole 4714. The channel 4710 and the guide pin hole 4712 form a unitary opening, as shown in FIG. 47b. The guide pin hole 4712 can be configured to have a diameter that is larger than the width of the channel 4710 in order to allow insertion of a guide pin (shown in FIG. 47b) disposed on the anterior awl 4618. The locking hole 4714 is disposed substantially adjacent to the guide pin hole 472 and closer to the distal end of the portal slide 4610. The locking pin hole is configured to accommodate insertion of a locking mechanism disposed on the anterior awl 4618 (as shown in FIG. 47b). In some embodiments, the back portion 4830 of the portal slide 4610 includes grooved channels disposed on the interior portion of the slide 4610 that are configured to allow sliding of the anterior awl 4618. The channels can additionally secure the anterior awl 4618 once it is inserted into the portal slide 4610. Further, the back portion 4830 also includes an open top end 4752 that is connected to the locking hole 4714 via a narrowing neck portion 4754.

FIG. 47b illustrates further details of the anterior awl 4618. The awl includes a distal end 4722, a proximal end 4726 and a shaft portion 4724 disposed between the distal end 4722 and the proximal end 4726. In some embodiments, the proximal end 4726 can be configured to be narrower than the shaft portion 4724 (or have a narrowing section) that allows securing the awl to vertebrae. The distal end 4722 includes a locking mechanism 4728, which can be configured to be a nut-and-bolt combination, wherein the bolt is coupled to the shaft 4724 and the nut is configured to secure the anterior awl 4618 to the back portion 4830 of the slide portal 4610 (as shown in FIG. 47a). The nut 4728 is configured to have a diameter that is larger than the diameter of the locking hole 4714. The diameter of the bolt is configured to be slightly smaller than the width of the narrowing neck 4754 (whose width is smaller than then the diameter of the locking hole 4714). Once the awl 4618 is inserted into the portal slide 4610, the locking mechanism 4728 is aligned with the locking hole 4714 and the nut of the locking mechanism 4728 is configured to be tightened to secure the awl 4618 to the back portion 4830 of the portal 4610.

To guide the awl 4618 down the portal slide 4610, the guide pin 4720 is inserted into the guide pin hole 4712 and then slid down the slide's back portion 4830 along channel 4710. The pin 4720 is configured to be disposed on the shaft 4724 of the awl 4618 near the proximal end 4726 (as shown in FIG. 47b, the pin 4720 is disposed on the border between the shaft 4724 and the narrowing portion 4726). The pin 4720 can be configured as a bolt-and-washer combination, wherein one end of the bolt is coupled to the shaft 4724 and a washer is secured to the other end of the bolt. The diameter of the washer is configured to be smaller than the diameter of the guide pin hole 4712, but larger than the width of the channel 4710 of the back portion 4830. This configuration prevents the anterior awl 4618 from falling out/wobbling when the awl is guided down the slide 4610.

Figures 47C, 47D:
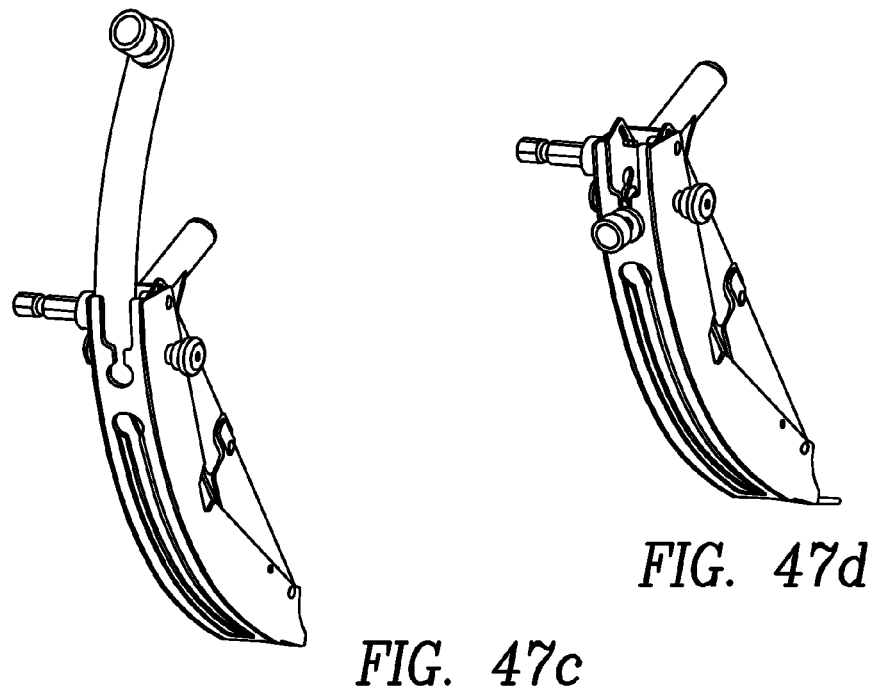

Referring to FIGS. 47c-47d, a guiding of the anterior awl 4618 is further illustrated. The guide pin 4720 of the anterior awl 4618 is inserted from the interior of the portal through the guide pin hole 4712 and slid down the length of the slide 4610 until the locking device reaches the locking hole 4714 in the portal. The guide pin is constrained by the anterior awl channel 4710 as the instrument is being delivered. The locking device is actuated by pulling and releasing the locking mechanism button into the locking hole.

The length of the anterior awls is configured such that direct visualization is possible when the anterior awl is piercing the annulus (advancing beyond the distal edge of the portal).

FIGS. 48a-48c illustrate various views of the construction of the portal 4510 including its exploded views (FIGS. 48b-48c). FIG. 48b is an exploded perspective view of the portal 4510. The portal includes the slide 4610, the push buttons 4616 coupled to the slide 4610, distal portion 4611, proximal portion 4613, and a handle 4620. The portal also includes a connector 4810 for connecting to the holding arm assembly (not shown in FIGS. 48a-c). As shown in FIG. 48b, the slide 4610 and the distal portion 4611 and a proximal portion 4613 are coupled to each other using pins 4820. The handle 4620 is coupled to the distal portion 4611 using screws (or bolts, or any other means) 4822.

FIG. 48c is an exploded view of the slide 4610. The slide 4610 includes side portions 4832, 4834 that are coupled together using a back portion 4830. The back portion is configured to allow insertion of the anterior awl 4618 (not shown in FIG. 48c) for locking the portal 4510. In other embodiments, the slide may be a unitary structure.

The portal 4510 is curved in a similar fashion as the portal shown in and discussed with regard to FIGS. 1-44c above in order to allow insertion of surgical instruments at an angle. The curvature radius of the portal 4510 can be also similar to the curvature radius of the portal shown in FIGS. 1-44c. In some embodiments, the construction of the portal cab include a mixture of machined components and sheet metal parts such as aluminum, stainless steel, plastic, or any other suitable materials.

In some embodiments, the portal 4510 can be delivered to the patient's lateral spine in the closed configuration (FIG. 46b) over serial dilators (shown and discussed with regard to FIGS. 1-44c above) and then can be opened (FIG. 46c) in-situ after the dilators are removed to provide direct visualization to the surgical site by opening the top. As stated above, opening the portal 4510 is accomplished by actuating the push buttons 4616 on either side of the portal while pulling on the pull handle 4620. When the movable top 4612 is in the open configuration, the push buttons 4616 can then be released to lock the movable top 4612 in the open configuration. Closing the movable top 4612 is accomplished by pressing the push buttons 4616 and pushing the pull handle 4620 until top is in closed configuration.

FIGS. 49a-49c illustrate further details the nerve root retracting tongue 4614. A final dilator 4910 (which is similar to the dilators shown in FIGS. 1-44c above), which directly precedes insertion of the portal 4510, includes nerve ramps 4912 disposed near the proximal end of the dilator 4910 and thus proximate to the vertebrae of the patient. The ramps 4912 are configured to interact with the nerve root retracting tongue 4614 built into the movable top. The nerve root retracting tongue 4614 slides between the two nerve ramps 4912 on the dilator 4910 to get under the exiting nerve root and retract the nerve beyond the safe surgical zone created by the portal. FIG. 49a illustrates the dilator 4910, which is similar to the dilators shown and discussed in connection with FIGS. 1-44c. FIG. 49b illustrates the portal 4510 being slid over the dilator 4910 and the dilator 4910 is about to interact with the ramps 4912. FIG. 49c illustrates the dilator 4910 having its ramps 4912 interact with the tongue 4614 of the portal 4510.

Figure 50A:
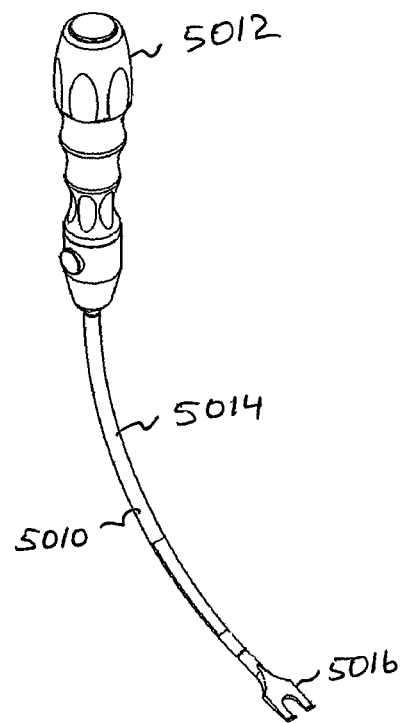
Figure 50B:
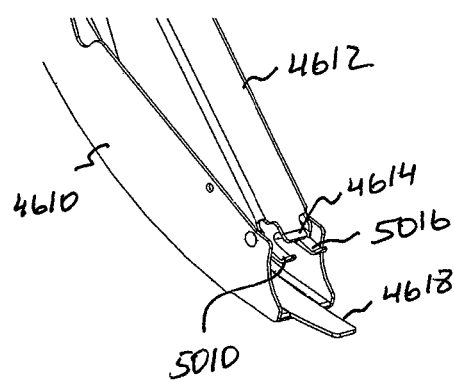

FIGS. 50a-b illustrate use of a bifurcated nerve retractor tool 5010 to move the existing nerve outside the portal confines. The tool 5010 includes a handle 5012 disposed distally from the vertebral body, a proximal end 5016 having a bifurcated end, and a curved shaft 5014 disposed between the handle 5012 and the proximal end 5016. Referring to FIG. 50b, once the movable top 4612 is opened and direct visualization is achieved, the bifurcated nerve retractor tool 5010 is configured to move the exiting nerve root outside the portal confines. Should the nerve root retracting tongue 4614 fail to completely remove the exiting nerve root from inside the portal, the tool 5010 can be used to move the nerve. Bifurcated end allows two nerve root retractor tips to move around the tongue built into the portal.

The portal discussed in connection with FIGS. 45-50b is configured to be curved in a similar manner as the portal and/or instruments shown and discussed in connection with FIGS. 1-44c. The angle of curvature can be selected according to system's specifications and/or as desired.

FIGS. 51-53d illustrate an exemplary guide wire delivery system 5100 that can be used in connection with the guided lumbar interbody fusion procedures disclosed above, according to some embodiments of the present invention.

Figure 51:
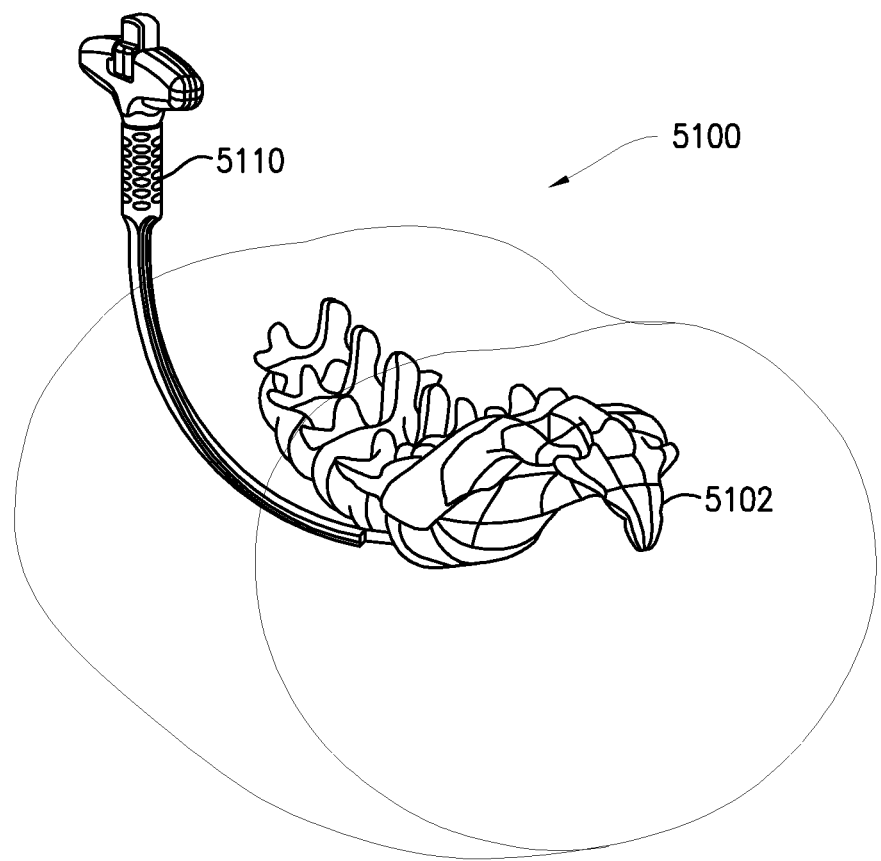
FIGS. 51, 52*a*-*b*, 53*a*-*d* illustrate an exemplary guide wire delivery instrument that can be used with a guided lumber interbody fusion technique, according to some embodiments of the present invention.

In some embodiments, the presented invention is configured as a curved instrument used to deliver a guide wire to a specific location. The instrument includes a cannulated curved shaft having a ⅓ circle profile with a proximal end and a distal end. The proximal end is configured as a T-Handle with an elongated shaft to facilitate full six-degree-of-freedom control and the proximal end tapers to a point the size of the inner cannulation of the shaft. In some embodiments, the instrument includes a blunt probe configured to slightly extend past the distal end to make the tapered "point" into a blunt surface. The blunt probe can be locked to the curved base by using a simple quarter turn lock. This instrument is delivered with the blunt probe along the inside surface of a surgeon's (or other medical professional's) finger to a surgical site. After verifying the location using fluoroscopy, the blunt probe can then be removed and a guide wire can be delivered to the surgical site. The present invention is configured to delivering a guide wire from a curved/oblique angle while leveraging the surgeon's tactile finger dilation by sliding an instrument along the inside of the finger and then delivering a guide wire through the instrument. Instrument can be used in the GLIF technique to deliver a curved guide wire in the spine and also to deliver a guide wire for locating trochanteric nails in hip surgeries. FIG. 51 illustrates the above described instrument 5110 being delivered to the vertebrae 5102. FIGS. 52a-53d illustrate additional details of the instrument 5110.

Figures 52A, 52B:
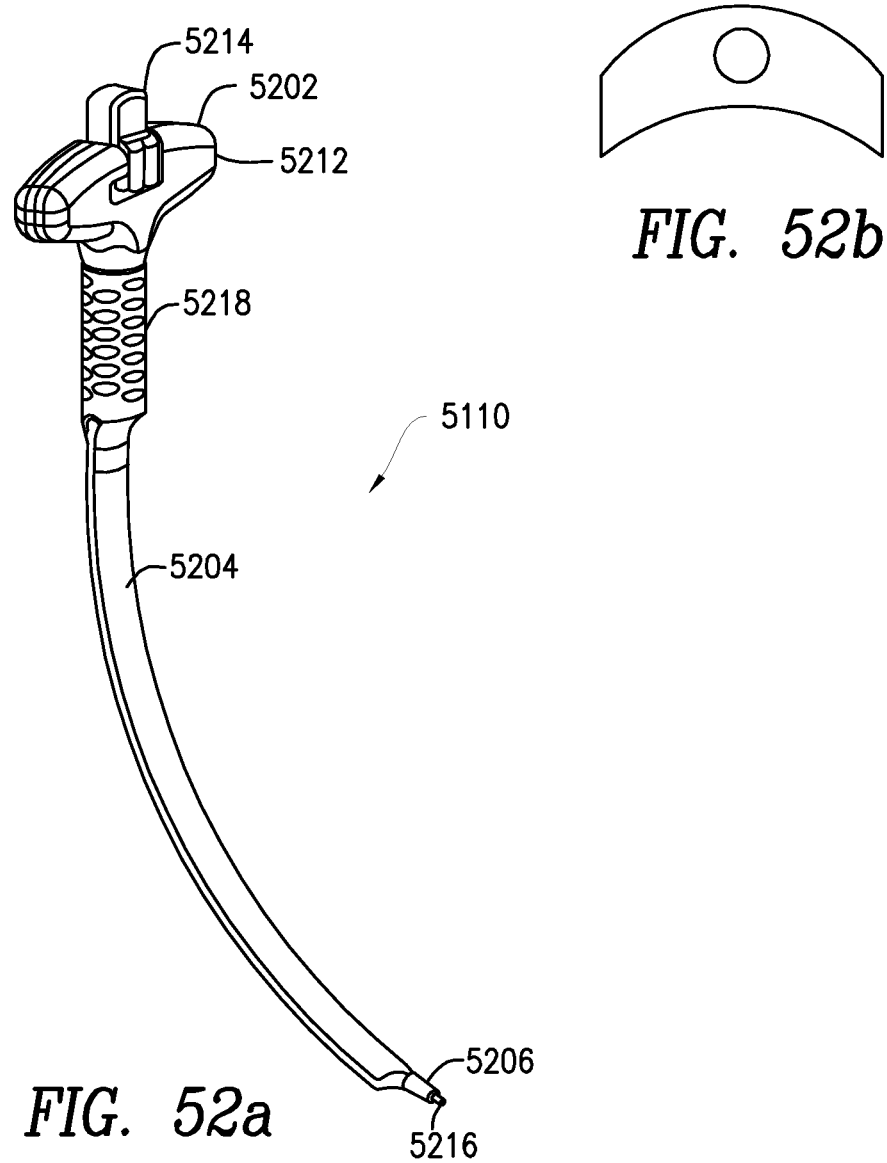

Referring to FIGS. 52a-b, the instrument 5110 includes a proximal end 5206, a distal end 5202, a shaft disposed between the proximal end 5206 and the distal end 5202. The distal end 5202 further includes a T-handle 5212 with an elongated shaft 5218. The proximal end 5206 includes a sharp tapered end 5216 configured to pierce annulus/bone. The shaft 5204 is configured to have a circular profile (e.g., a ⅓ circle profile). The distal end further includes a blunt probe knob 5214. The instrument 5110 also includes a blunt inner probe that has the knob 5214 and a flexible shaft with a blunt end. The knob 5214 of the inner probe is configured to lock into the T-handle 5212 for full assembly. The circular profile of the shaft 5204 is configured to help guiding the instrument 5110 with surgeon's finger (i.e., the geometry of the shaft "hugs" the inside of the surgeon's finger).

Figure 53A:
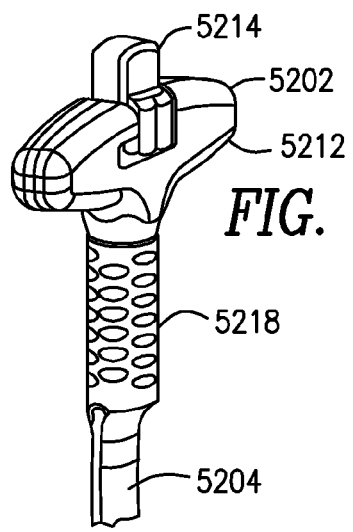

FIGS. 53a-d illustrate further detail on the inner probe 5320. Referring to FIG. 53a, the T-handle 5212 has an elongated shaft 5218 to fully control six degrees of freedom of the instrument. Once the instrument is delivered along the inside of the surgeon's finger, the handle 5212 can be used to fine tune location of the instrument 5110. The T-handle 5212 also allows the surgeon to keep his hand out of the radiation zone of the fluoroscope. In some embodiments, the handle 5212 can include a connection point for an external stabilization arm that can be attached to a surgical table. (which is similar to the stabilization arm shown in FIGS. 1-45).

Figure 53B:
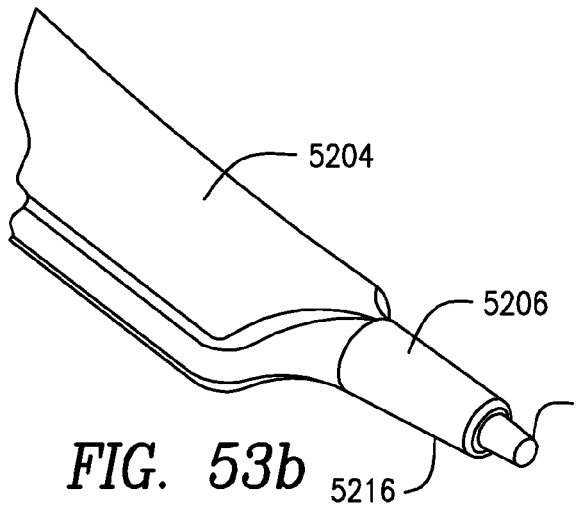
Figure 54A:
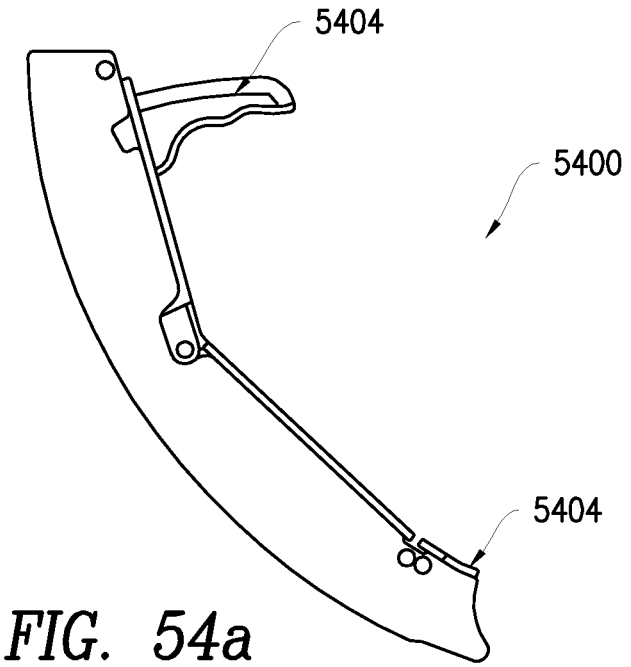
FIGS. 54*a*-*b* illustrate another exemplary curved access portal having a movable top for accessing vertebrae, according to some embodiments of the present invention.
Figure 54B:
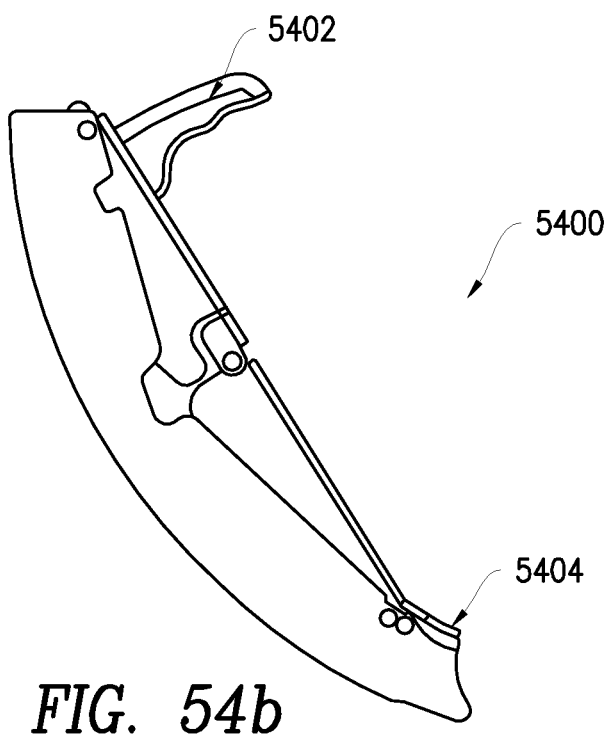

Referring to FIG. 53b, when assembled, the end 5324 of the blunt inner probe 5320 is configured to extend past the tapered proximal end 5206. This acts to smooth the end geometry of the instrument 5110 to avoid cutting the surgeon's glove when delivered along surgeon's finger.

Figure 53C:
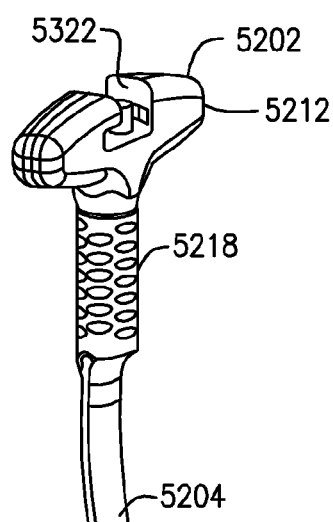
Figure 53D:
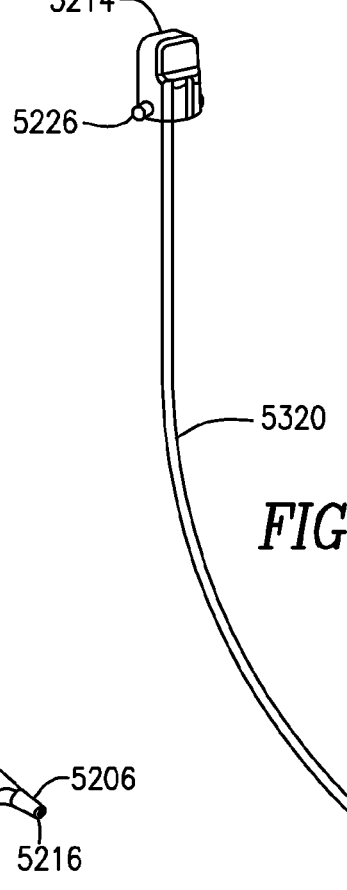

Referring to FIGS. 53c-d, the instrument 5110 includes a slot 5322 that is configured to extend into a channel disposed within the shaft 5204 (the channel is disposed between the distal end 5202 and the proximal end 5206 of the instrument 5110). The slot 5322 and the inner channel allow insertion of the probe's flexible shaft at the distal end and then guiding it down toward the proximal end. The probe further includes locking tabs 5326, which are configured to interact with the slot 5322 features on the T-handle 5312 to fully secure the blunt inner probe. In some embodiments, the locking tabs 5326 are configured to quarter-turn into the slot 5322 features.

FIGS. 54a-b illustrate another exemplary curved access portal 5400, according to some embodiments of the present invention. In some embodiments, the portal 5400 can be delivered to the patient's lateral spine in a closed configuration (FIG. 54a) over one or more dilators and then can be opened (FIG. 54b) in-situ after the dilators are removed to provide direct visualization to the surgical site by opening the movable top. The portal 5400 is similar to the portal 4510 shown and discussed with regard to FIGS. 45-50b. The portal 5400 includes a handle 5402 that includes a grip portion allowing better grip of the handle during opening and closing of the movable top 5412 (or any portions of the movable top 5412). Additionally, the portal 5400 includes a nerve root retracting tongue 5404 disposed near the proximal end of the portal 5400. In some embodiments, the retracting tongue 5404 is configured to lift away from the portal slide as the portal 5400 is switched from the closed position (FIG. 54a) to the open position (FIG. 54b). Such lifting allows for better nerve retraction away from the surgical site.

FIGS. 55-72c illustrate additional exemplary embodiments of a guided lumbar interbody fusion systems and tools employed during a procedure performed by these systems. As can be understood by one skilled in the art, the illustrations in FIGS. 55-72c are provided here for exemplary, non-limiting purposes, and other variations of tools and system are possible. The concepts shown in FIGS. 55-72c may also incorporate, to the extent relevant, illustrations and discussions presented above with regard to FIGS. 1-54b.

Figure 55:
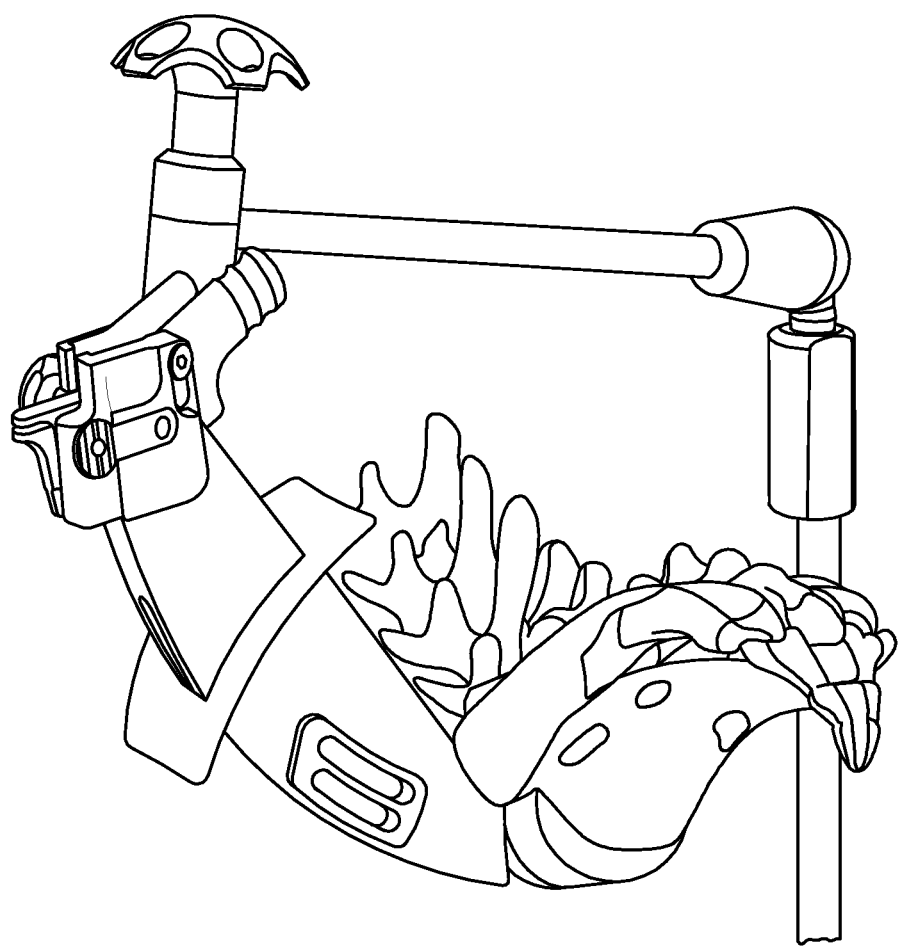
FIG. 55 illustrates yet another exemplary curved access system that can be used during a guided lumbar interbody fusion procedure, according to some embodiments of the present invention.
Figure 56A:
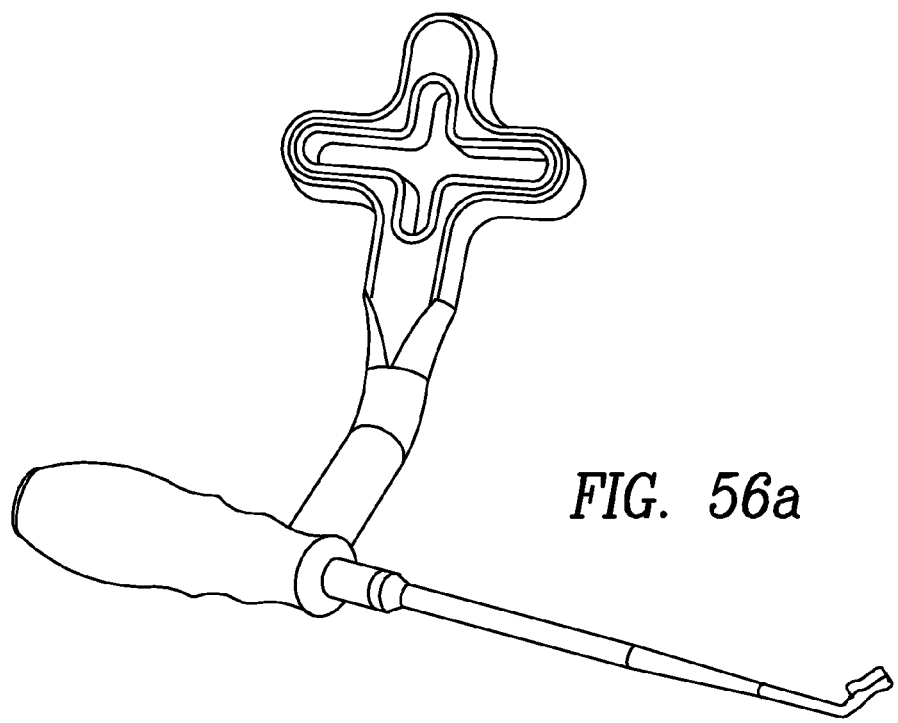
FIGS. 56*a*-56*h* illustrate an exemplary targeting device for locating an incision area, according to some embodiments of the present invention.
Figure 56B:
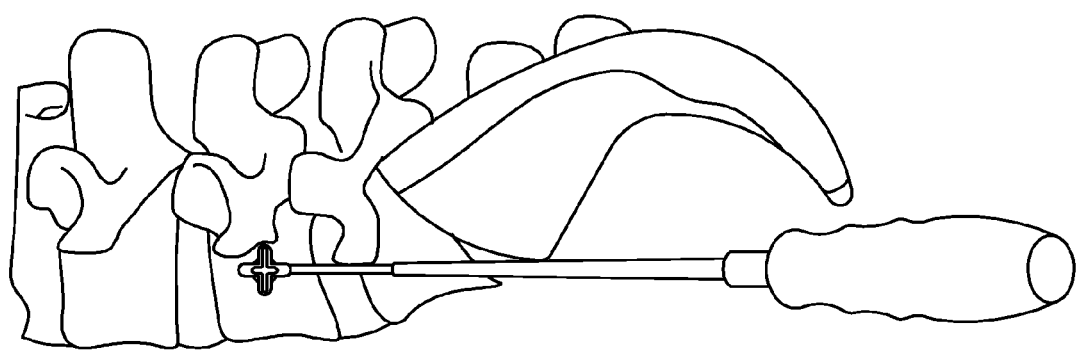
Figure 56C:
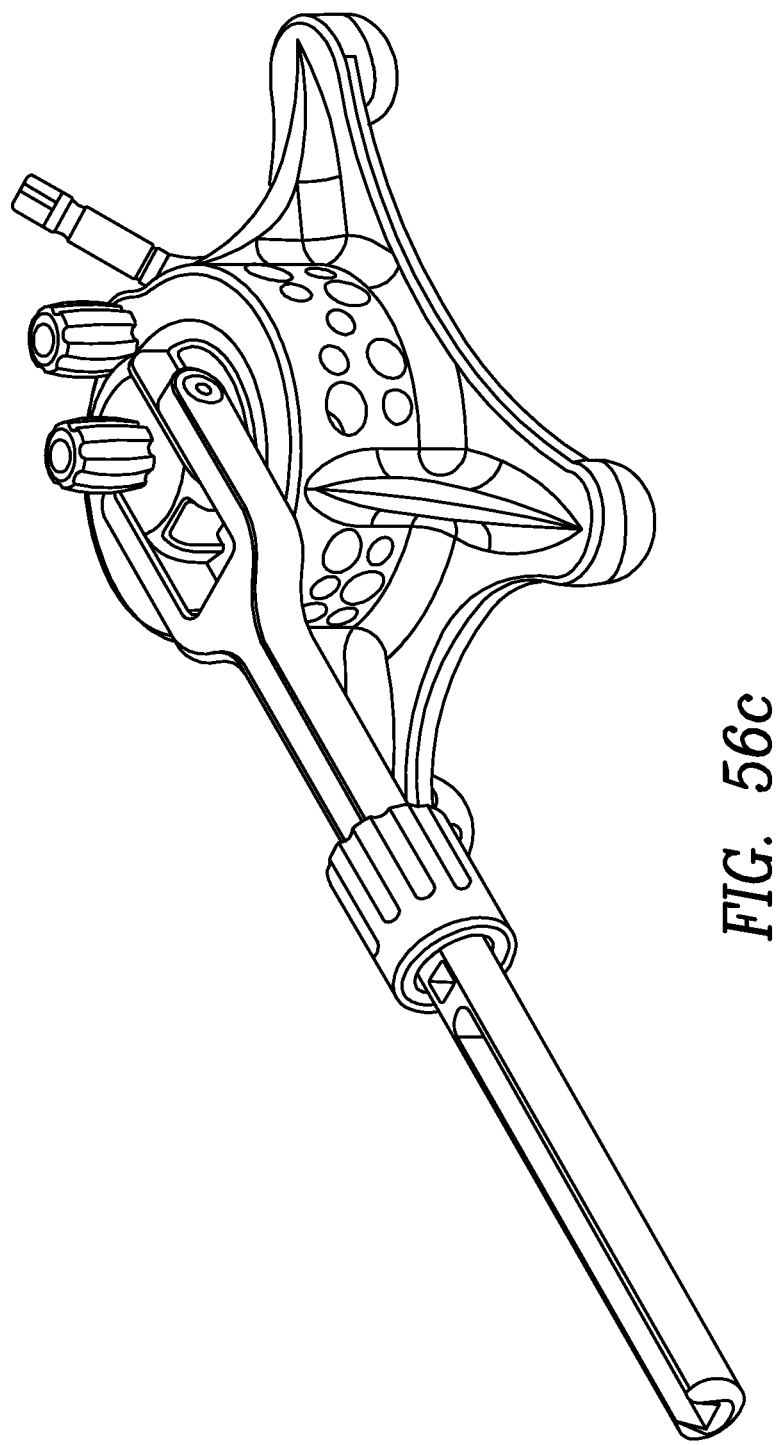
Figure 56D:
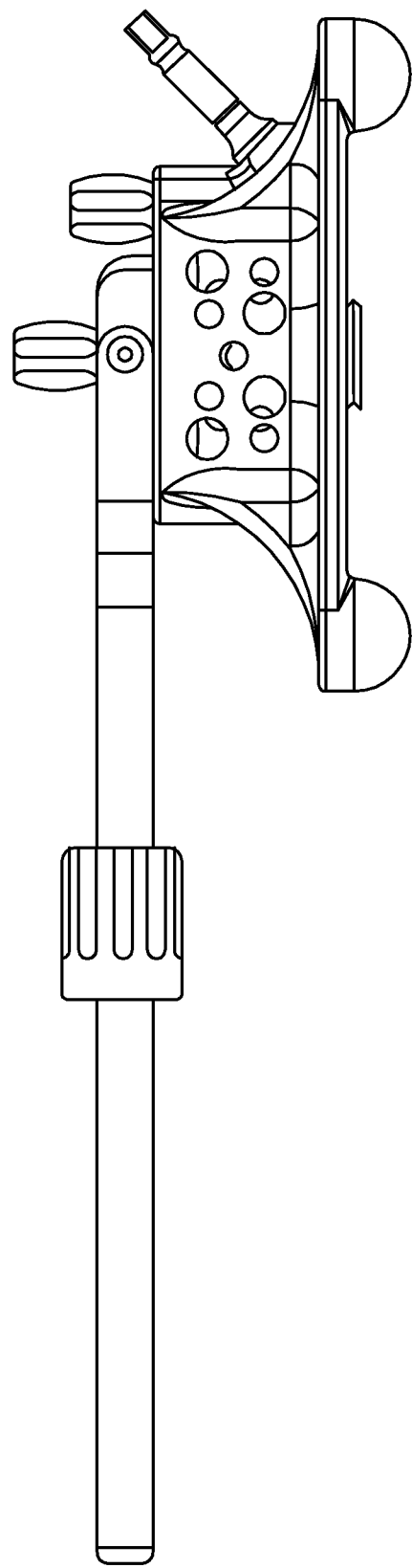
Figure 56E:
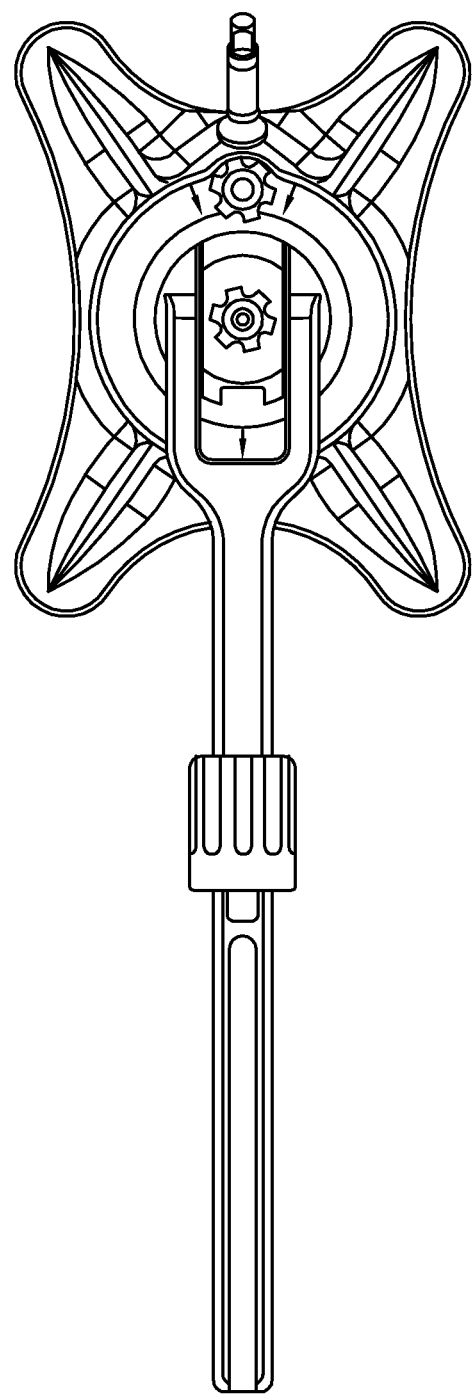
Figure 56F:
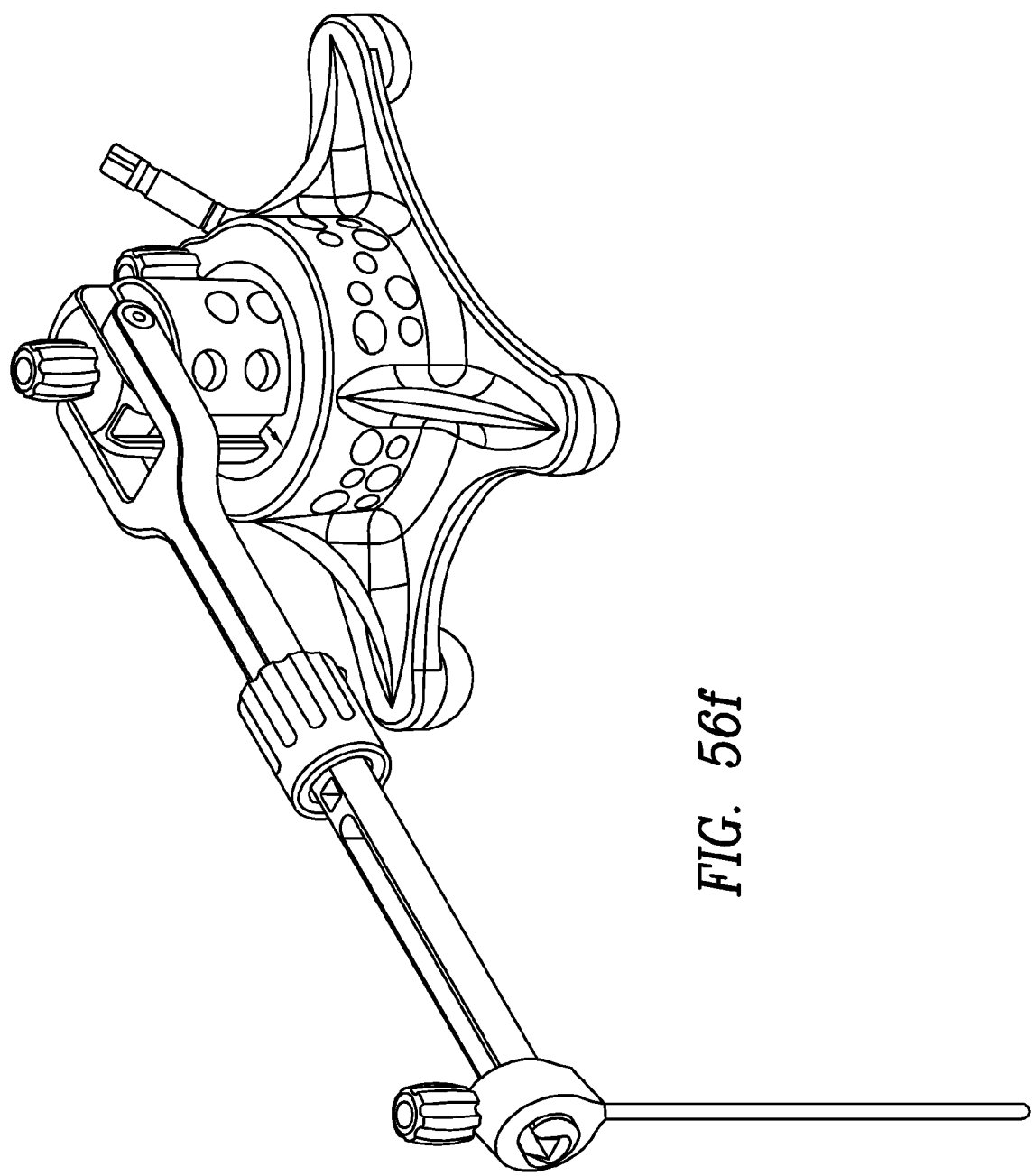
Figure 56G:
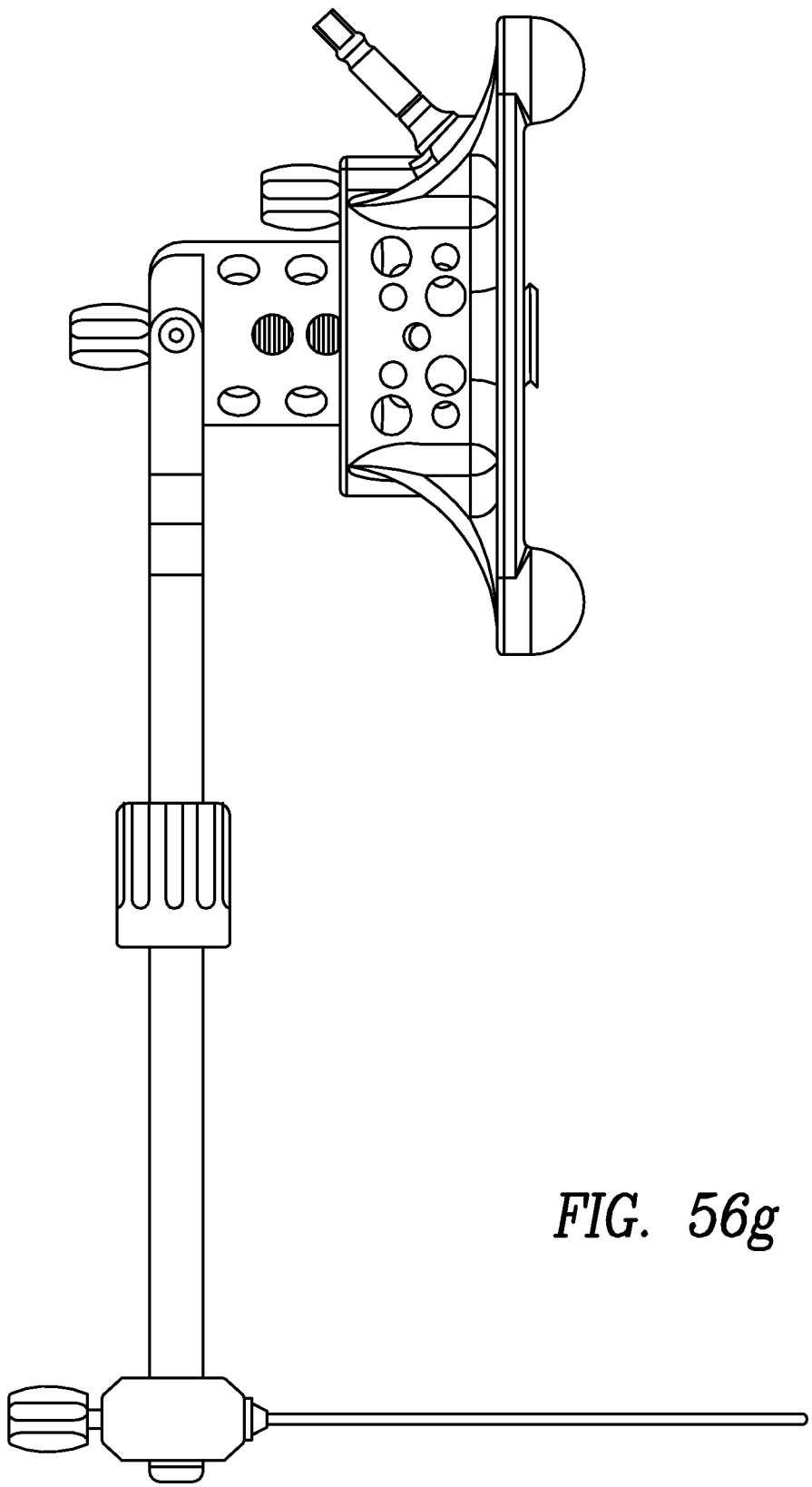
Figure 56H:
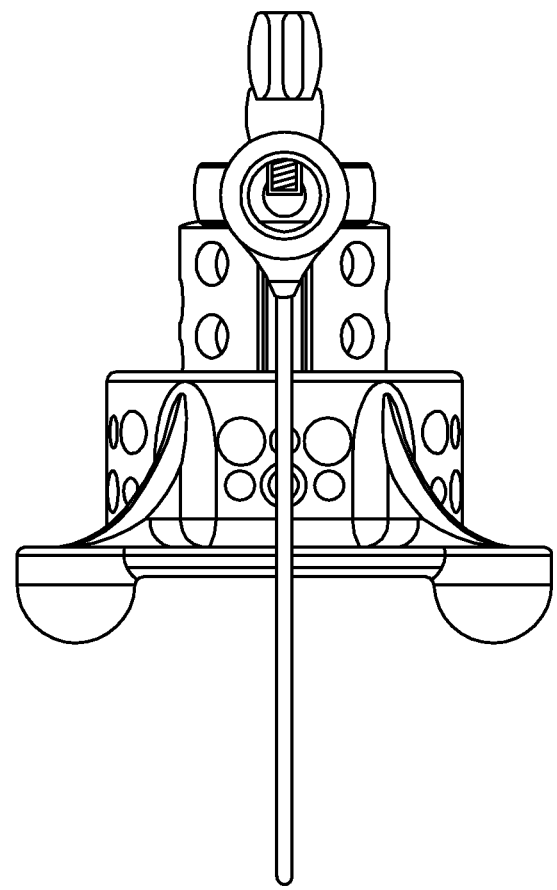

Referring to FIG. 55, another exemplary embodiment of a curved access system is illustrated. The system shown in FIG. 55 can be configured to be used during a guided lumbar interbody fusion procedure, according to some embodiments of the present invention. The system may have similar parts and employ similar concepts as the systems shown in FIGS. 1-54b and discussed above.

FIGS. 56a-56h illustrate an exemplary targeting device for locating an incision area, according to some embodiments of the present invention. The incision area is located using the targeting device by placing external references on the patient's skin and taking inter-operative x-rays. As can be understood by one skilled in the art, other ways of locating an incision area are possible and are not limited to the use of the targeting tool device shown in FIGS. 56a-h. See also FIGS. 74-77 below and Example Procedure B discussed above.

Figure 57A:
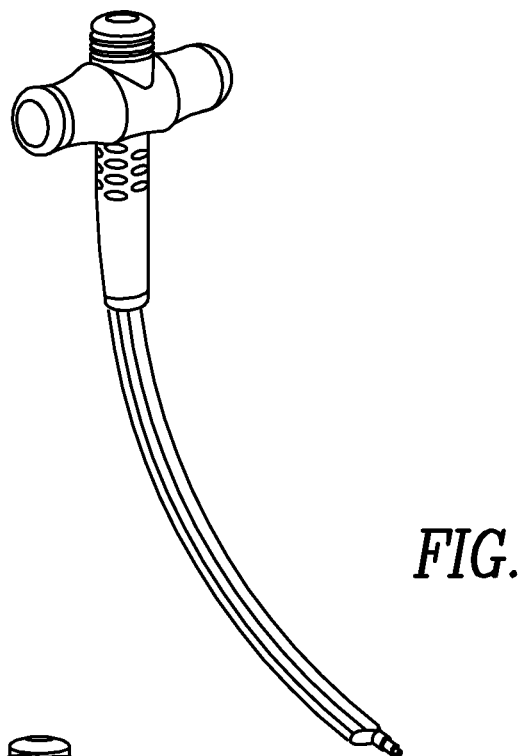
FIGS. 57*a*-57*c* illustrate an exemplary guide wire delivery trocar instrument, according to some embodiments of the present invention.
Figure 57B:
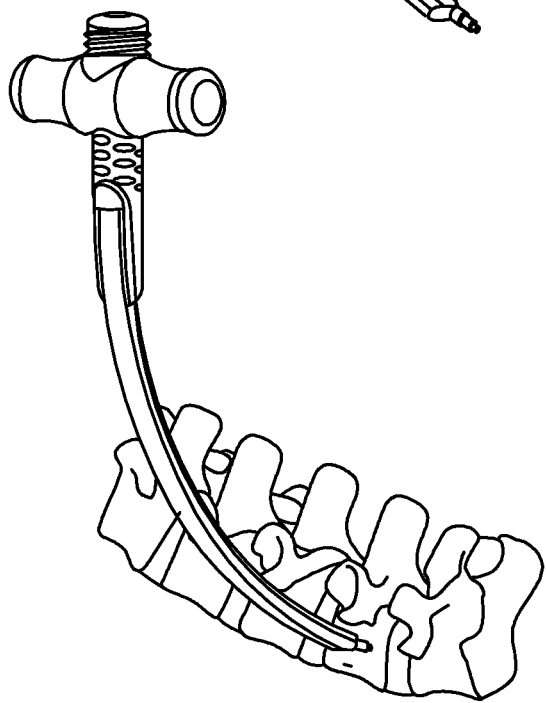
Figure 57C:
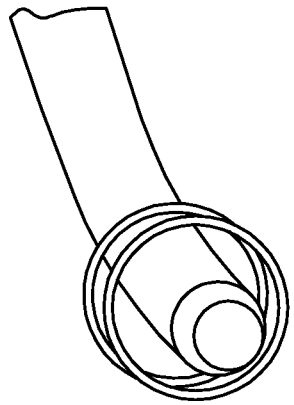

FIGS. 57a-57c illustrate an exemplary guide wire delivery trocar instrument, according to some embodiments of the present invention. As shown in FIGS. 57a-57c, a guide wire delivery instrument can be configured to safely deliver a guide wire by leveraging the surgeon's tactical finger dilation and then delivering the instrument over surgeon's finger placement. Once placed and verified with fluoroscopy, the instrument can be impacted into the annulus. The inner stylette (neuro monitoring device) can be removed and a guide wire can be safely delivered. Concentric rings (shown in FIG. 57c) can be configured to ensure that the guide wire is delivered normal to disc. The instrument is then carefully removed leaving the guide wire. In some embodiments, a T-handle (FIGS. 57a-b) integrates an elongated vertical section for increased control. In some embodiments, a curved ⅓ circle profile contours fingers. As can be understood by one skilled in the art, other ways of delivering a guide wire are possible.

FIGS. 58a-58c illustrate an exemplary psoas muscle separator, according to some embodiments of the present invention. As shown, a psoas sweeper separates the psoas muscle from the spinal column by sweeping a "foot" like shape (FIG. 58c) in the direction of the exiting nerve root to "push" the nerve root and separate the muscle. In some embodiments, the curved portion of the instrument allows end piece placement normal to vertebral bodies. In some embodiments, the psoas muscle separator includes a twisting knob that is configured to turn distal geometry of the "foot". Inner cannulation can be delivered over a k-wire. In some embodiments, the separator tool can be configured to include an offset handle that allows easy control of the instrument.

FIGS. 59a-59c illustrate exemplary sequential dilators, according to some embodiments of the present invention. In some embodiments, serial dilators (FIGS. 59a-59b) are configured to open soft tissue for delivery of a portal (shown in FIGS. 61a-61g). In some embodiments, a first dilator is inserted into the annulus for stabilization, as shown in FIG. 59c. An impacting wand can be used to aide in impacting initial dilator into annulus, as is also shown in FIG. 59c. In some embodiments, features on sequential dilators can be configured to interface with the impacting wand to drive the dilators to the surgical site.

Figure 60A:
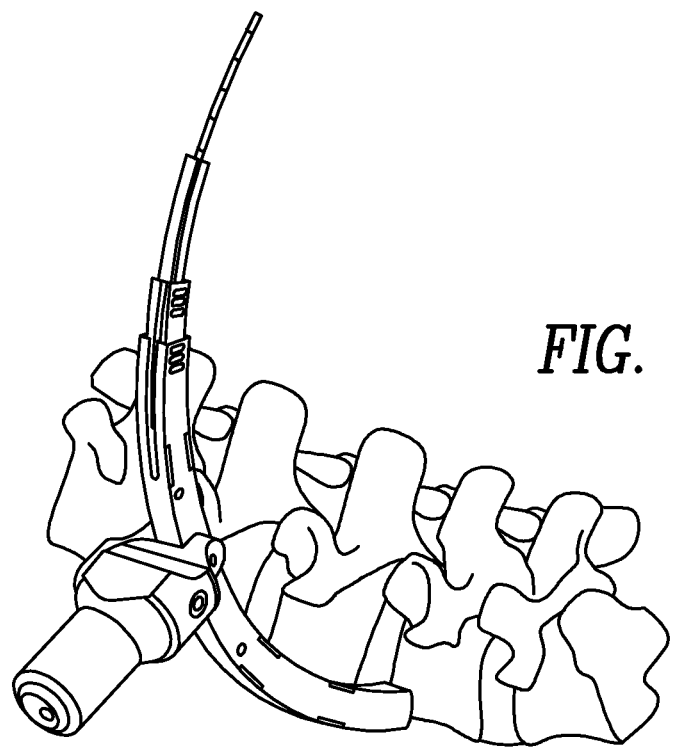
FIGS. 60a-60c illustrate an exemplary dilator impactor, according to some embodiments of the present invention.
Figure 60B:
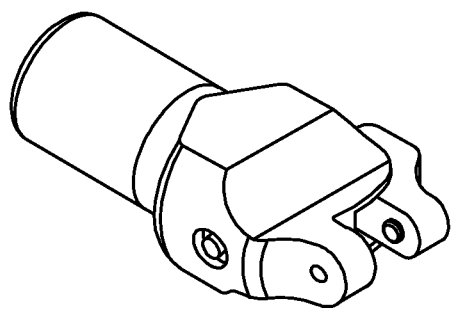
Figure 60C:
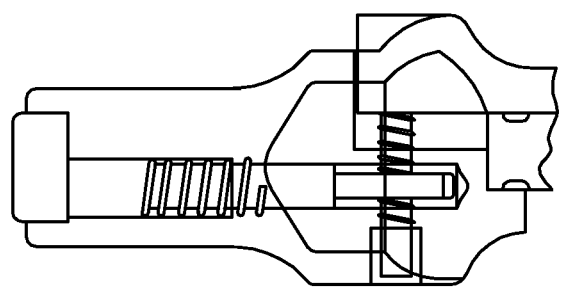
Figure 61A:
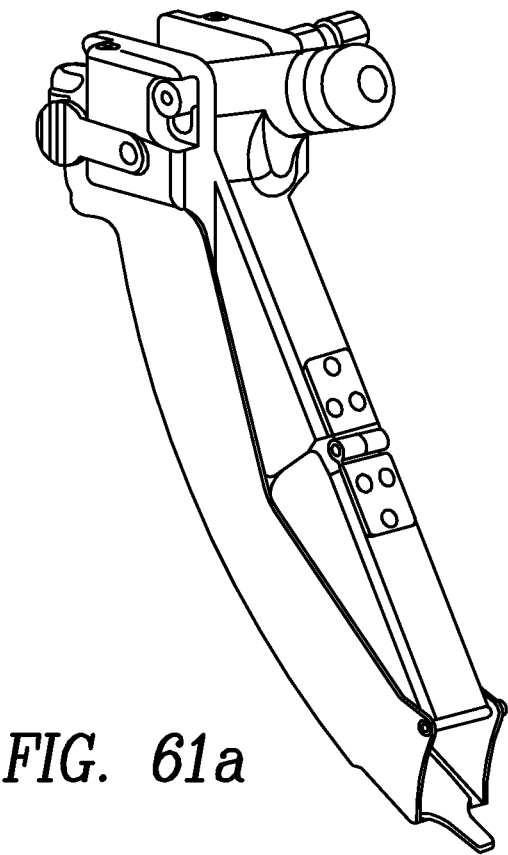
Figure 61C:
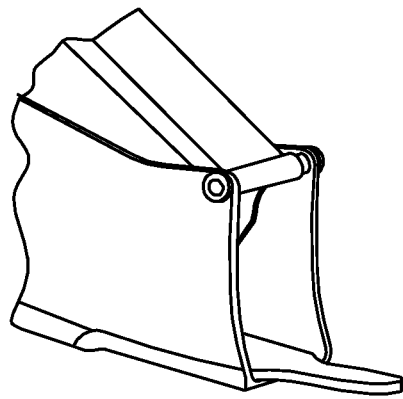
Figure 61B:
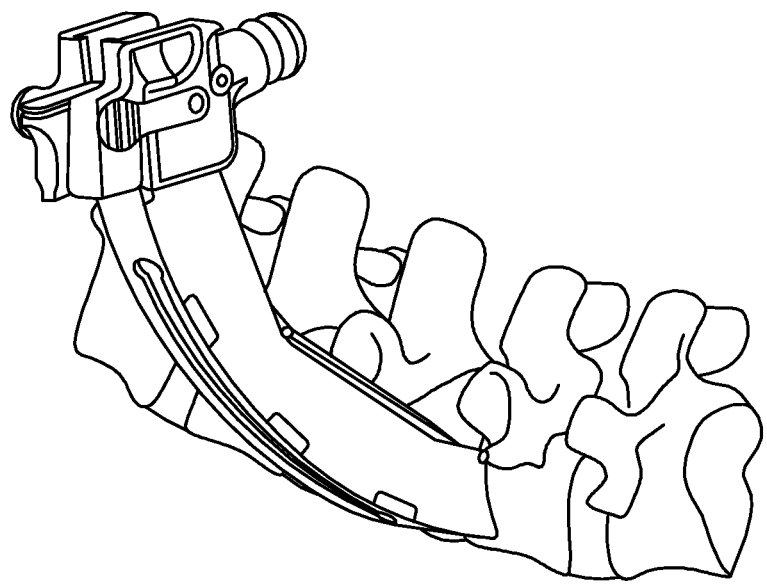

FIGS. 60a-60c illustrate an exemplary dilator impactor, according to some embodiments of the present invention. In some embodiments, the dilator impactor is configured to attach to dilators (FIG. 60a) in order to provide an impacting surface for advancing the dilators. In some embodiments, the dilators can be configured to include multiple connection points that allow the impactor to be attached close to the skin surface for optimal impaction.

FIGS. 61a-61g illustrate an exemplary portal, according to some embodiments of the present invention. As illustrated in FIGS. 45-54b, in some embodiments, the portal can be configured to have a movable top design. As stated above, the portal may include a pulling handle that is configured to open the movable top and further include levers on each side of portal to lock the portal in a specific position. In some exemplary embodiments, a local cross-sectional area is approximately 20 mm×16.5 mm. As can be understood by one skilled in the art, the portal can have any local cross-sectional area. In some embodiments, an integrated anterior awl can be configured in a way such that it can be directly visualized (FIG. 61d) while performing an implantation procedure into the annulus. A ratcheting device (FIG. 61e) can be configured to maintain positioning of the anterior awl.

Figure 62A:
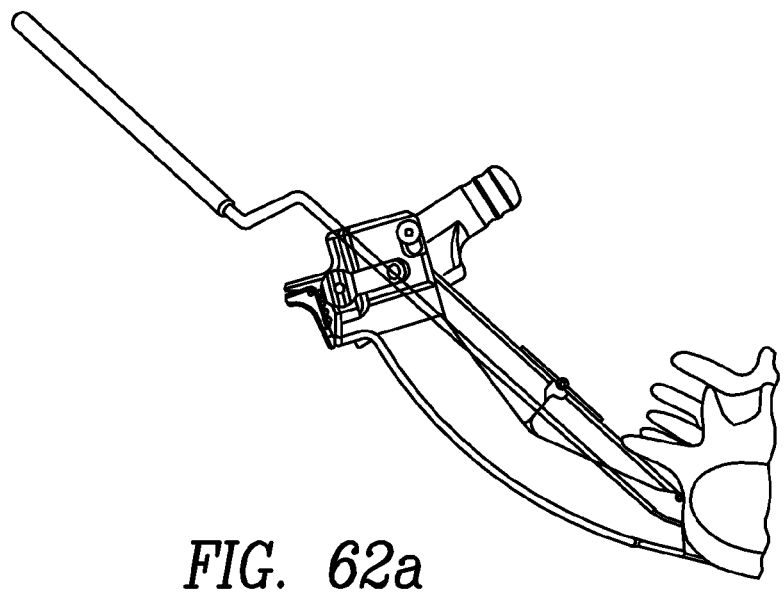
FIGS. 62a-62c illustrate an exemplary preparation of a working site during the guided lumbar interbody fusion procedure, according to some embodiments of the present invention.
Figure 62B:
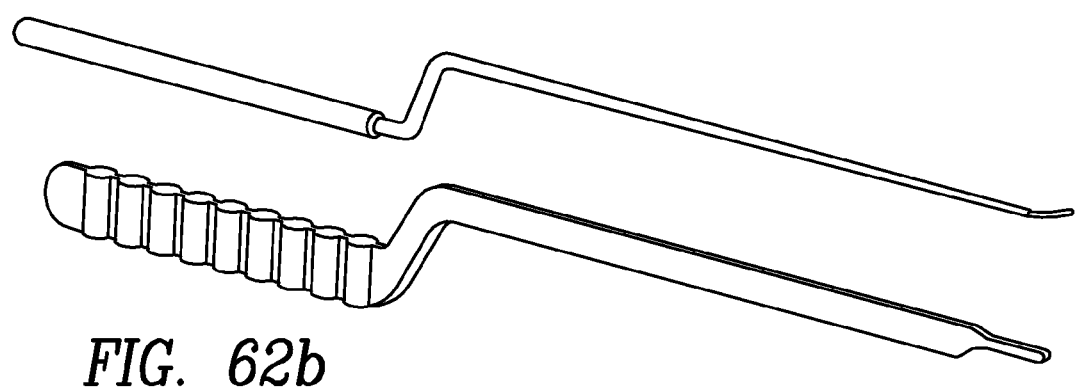
Figure 62C:
Figure 63A:
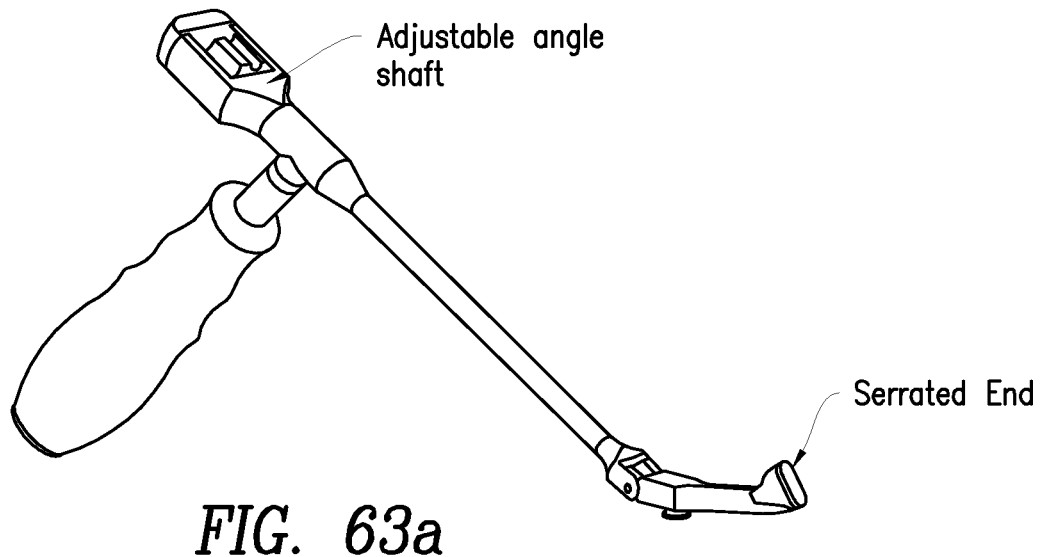
FIGS. 63a-63d illustrate an exemplary hinged box cutter instrument for removing annulus, according to some embodiments of the present invention.
Figure 63B:
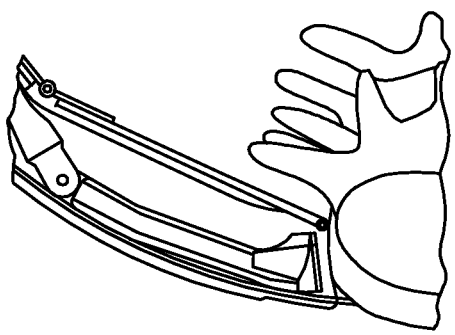
Figure 63C:
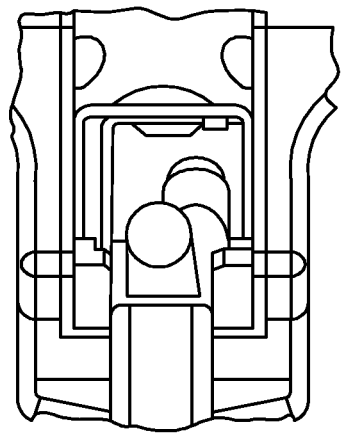
Figure 63D:
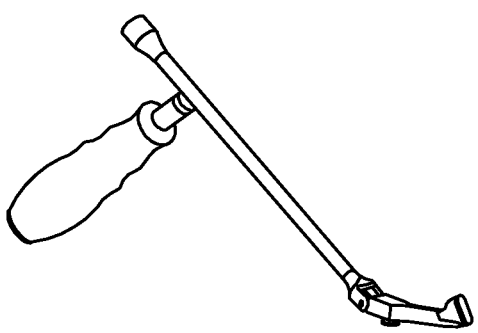

FIGS. 62a-62c illustrate an exemplary preparation of a working site during the guided lumbar interbody fusion procedure, according to some embodiments of the present invention. During preparation of the working site, a tissue retractor can be used, as shown in FIG. 62a. The tissue retractor can be configured to remove any unwanted nerve roots/plexus/soft tissue that may be in the path of the portal. In some exemplary embodiments, a Standard Penfield #4 tool can be configured to allow tissue retraction and blunt dissection. In some embodiments, the tissue retractor can be bayoneted to allow visualization over surgeon hand. As can be understood by one skilled in the art, other types of tissue retractors can be used.

FIGS. 63a-63d illustrate an exemplary hinged box cutter instrument for removing annulus, according to some embodiments of the present invention. In some embodiments, the hinged box cutter instrument is configured to include an adjustable angle shaft, an offset handle and a serrated end. The offset handle is configured to allow visualization over instrument. The hinged box cutter is configured to align with portal slot via a pin interaction. The hinged design of the cutter instrument is configured to enable the surgeon to move handle for better visualization. The hinged box cutter instrument can be configured to be used either when portal is open or closed.

Figure 64A:
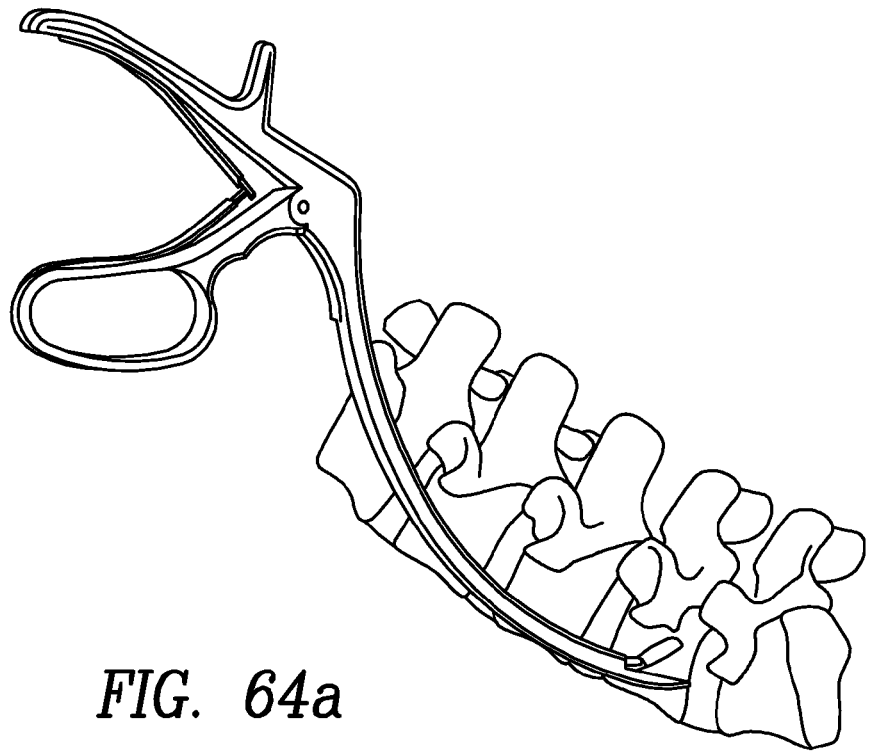
FIGS. 64a-64c illustrate an exemplary curved ronguer, according to some embodiments of the present invention.
Figure 64B:
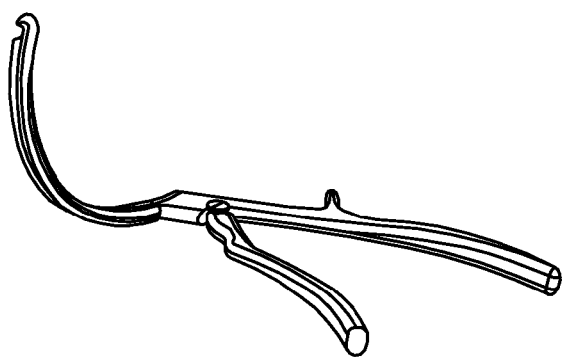
Figure 64C:
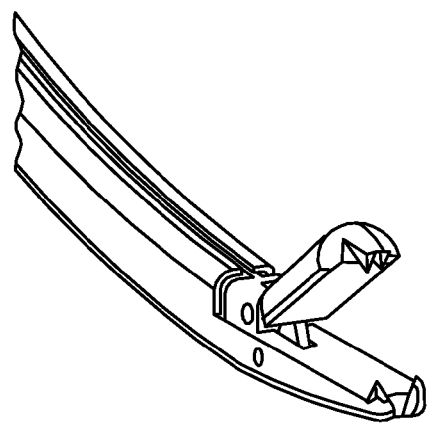

FIGS. 64a-64c illustrate an exemplary curved ronguer, according to some embodiments of the present invention. In some embodiments, the curved ronguer is configured to include a spring-loaded kerrison style handle that is configured to allow adequate comfort and control of instrument, which is similar to typical surgical instruments. The ronguer also includes biting "cobra" teeth (FIG. 64c) that are configured to cut, grab, and remove annular material.

Figure 65A:
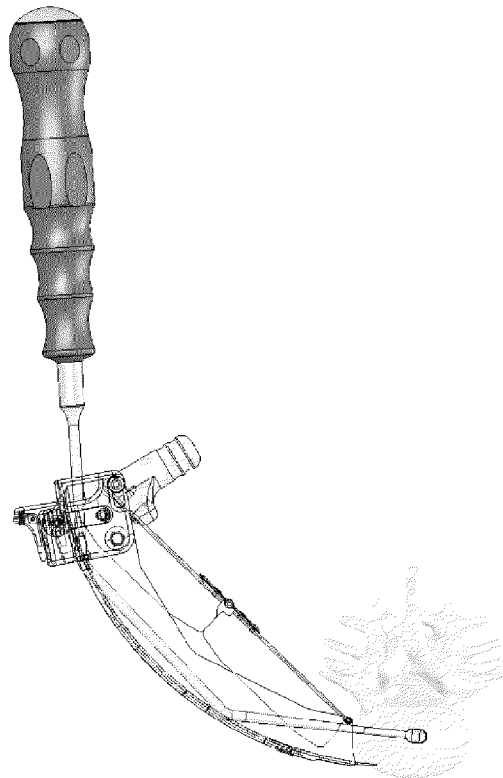
FIGS. 65a-65c illustrate exemplary curettes, according to some embodiments of the present invention.
Figure 65B:
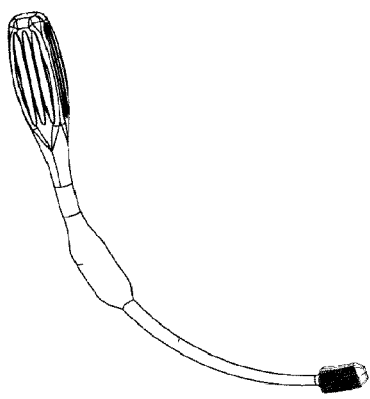
Figure 65C:
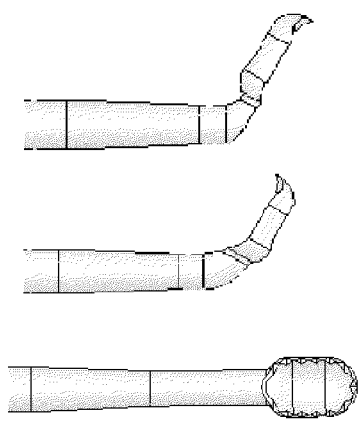
Figure 66A:
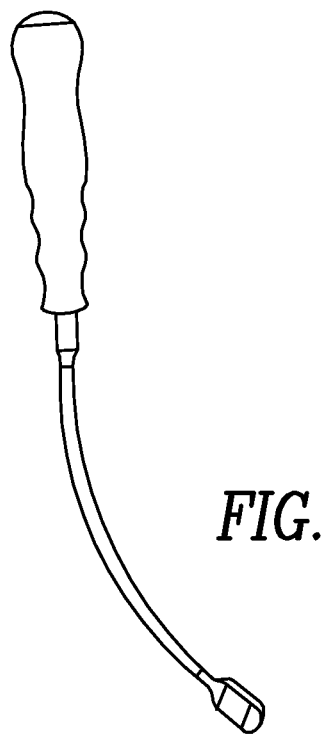
FIGS. 66a-66d illustrate an exemplary curved wedge rasp, according to some embodiments of the present invention.
Figure 66B:
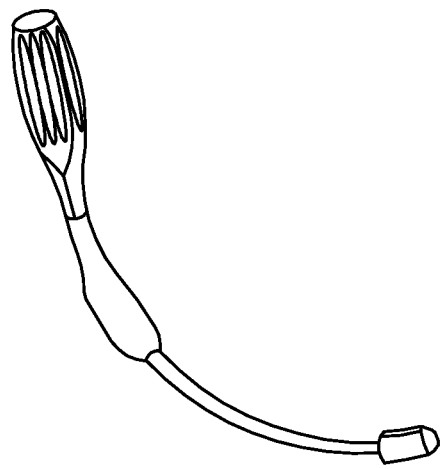
Figure 66C:
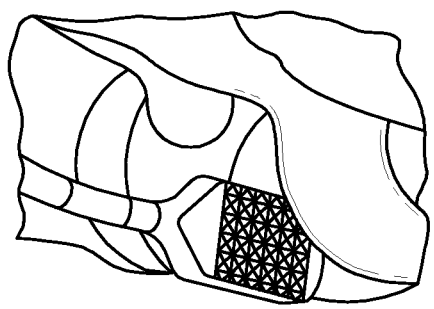
Figure 66D:
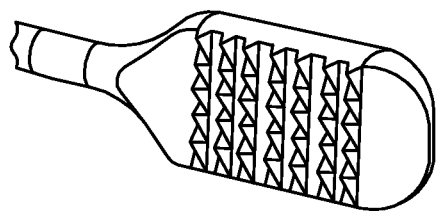

FIGS. 65a-65c illustrate exemplary curettes, according to some embodiments of the present invention. In some embodiments, the surgeon can use assorted curettes inside the portal, where the curettes can have the following configurations: having an upwardly directed tip, having a downwardly directed tip, having a leftward directed tip, and having a rightward directed tip (See, FIG. 65c). During procedure, the instrument will be partially constrained with portal via a supporting member to allow controlled movements within disc space.

FIGS. 66a-66d illustrate an exemplary curved wedge rasp, according to some embodiments of the present invention. In some embodiments, the rasp design is configured to scrape and remove material caught between the alternating tooth/flat section of the design. The rasp can be defined by a taper size, width of the rasp, and a length of rasp. Depending on the desired configuration and rasp's desired ability to scrape and remove material, these parameters may be accordingly adjusted and a different rasp can be used.

Figure 67A:
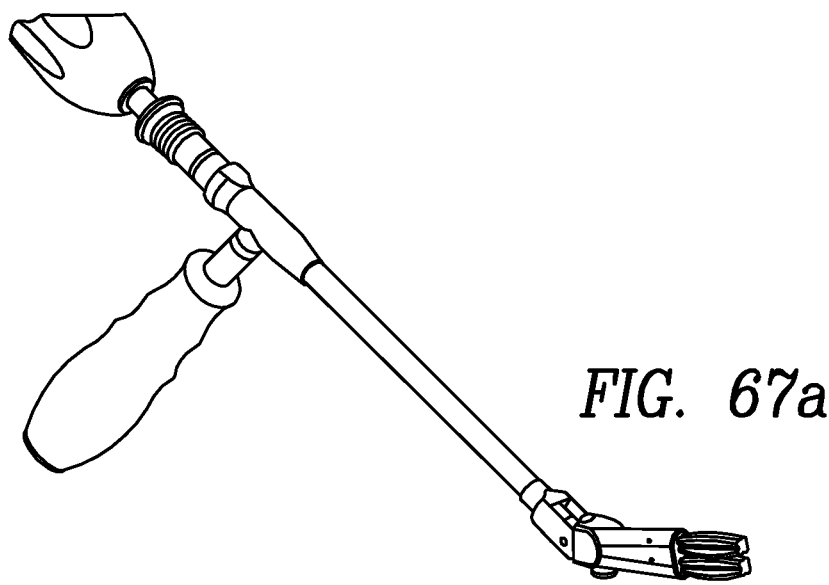
FIGS. 67a-67c illustrate an exemplary removal of the annulus, according to some embodiments of the present invention.
Figure 67B:
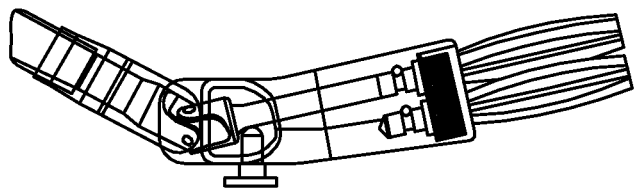
Figure 67C:
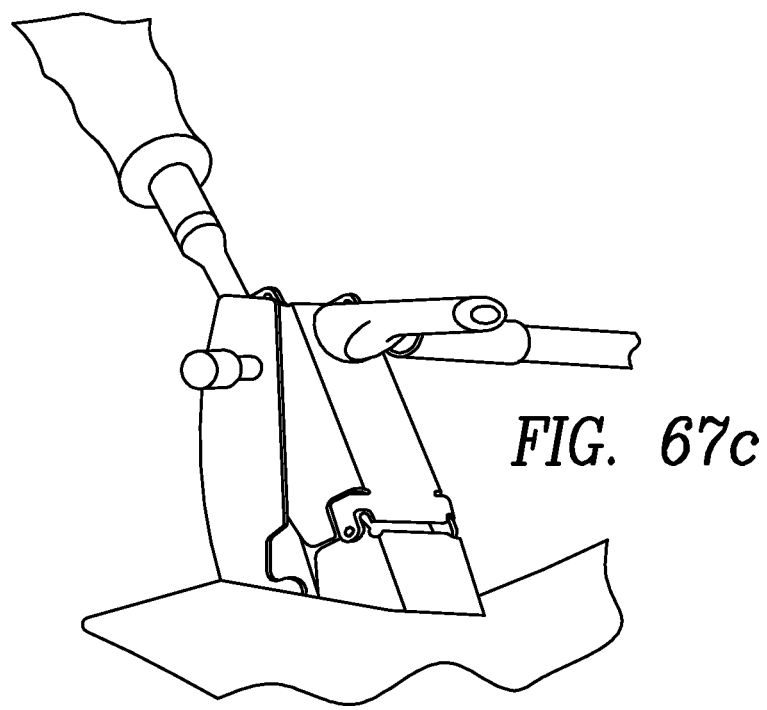

FIGS. 67a-67c illustrate an exemplary removal of the annulus, according to some embodiments of the present invention. In some embodiments, the disc whisk can be configured to be used to save time when clearing the disc space. In some embodiments, the disk whisk can be power driven to allow a more automated approach of clearing.

Figure 68:
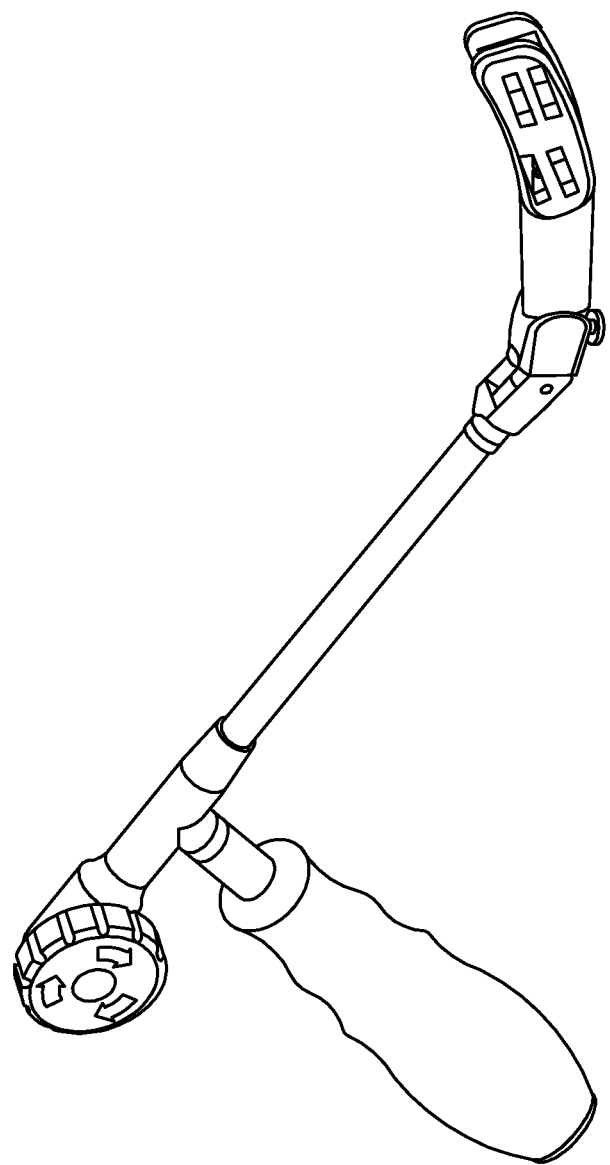
FIG. 68 illustrates an exemplary expandable trial implant inserter, according to some embodiments of the present invention.

FIG. 68 illustrates an exemplary expandable trial implant inserter, according to some embodiments of the present invention. In some embodiments, the surgeon can insert the expandable implant inserter into a cleared disc area and then expand its tip until the desired distraction of tissue is reached. Using fluoroscopy, the surgeon can then remove and insert an appropriate implant.

Figure 69A:
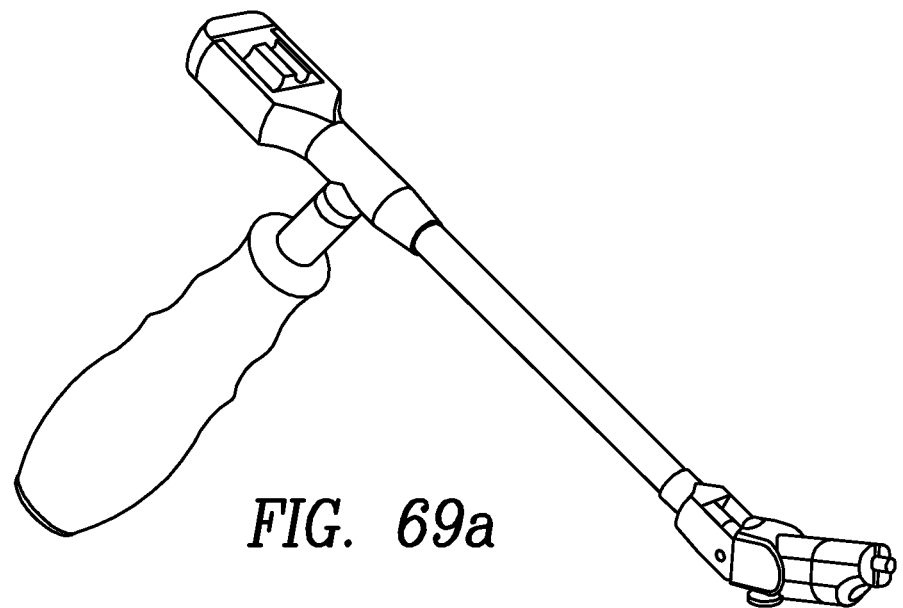
FIGS. 69a-69c illustrate an exemplary implant inserter, according to some embodiments of the present invention.
Figure 69B:
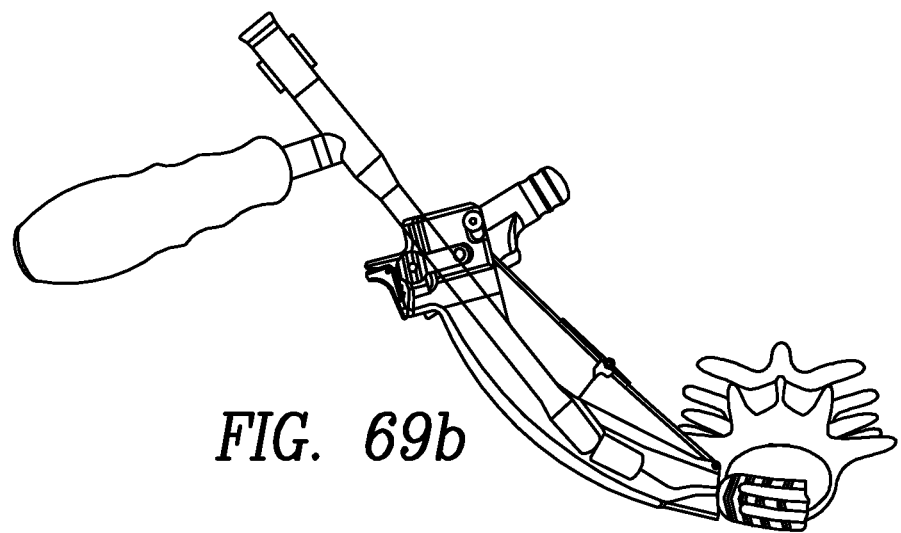
Figure 69C:
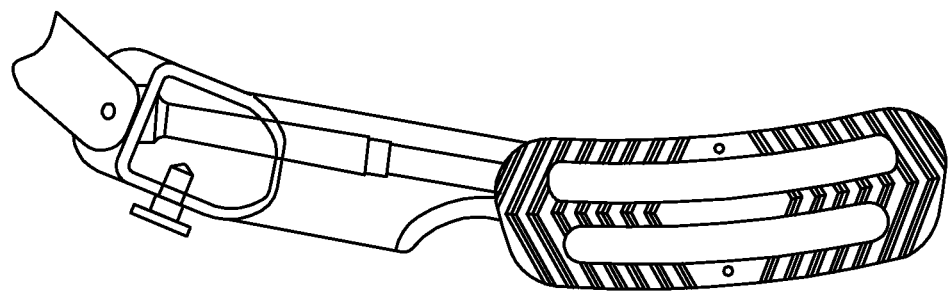

FIGS. 69a-69c illustrate an exemplary implant inserter, according to some embodiments of the present invention. The implant inserter shown in FIGS. 69a-69c is configured to run along inside the portal (shown in FIGS. 61a-g) to deliver an implant to a surgical site. By striking the plate at a proximal end, the implant inserter allows the surgeon to mallet the implant into place. (See, FIGS. 69b-69c).

Figure 70A:
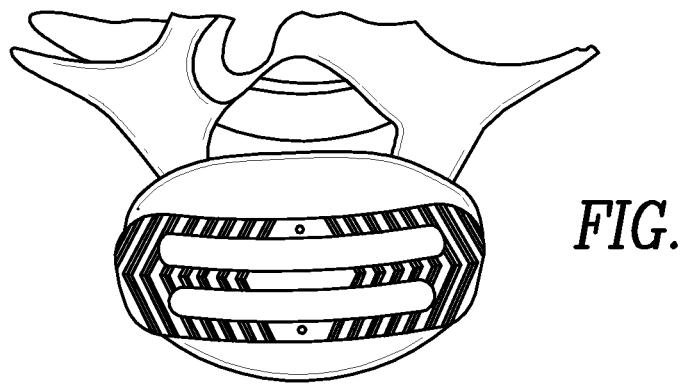
FIGS. 70a-70c illustrate an exemplary implant, according to some embodiments of the present invention.
Figure 70B:
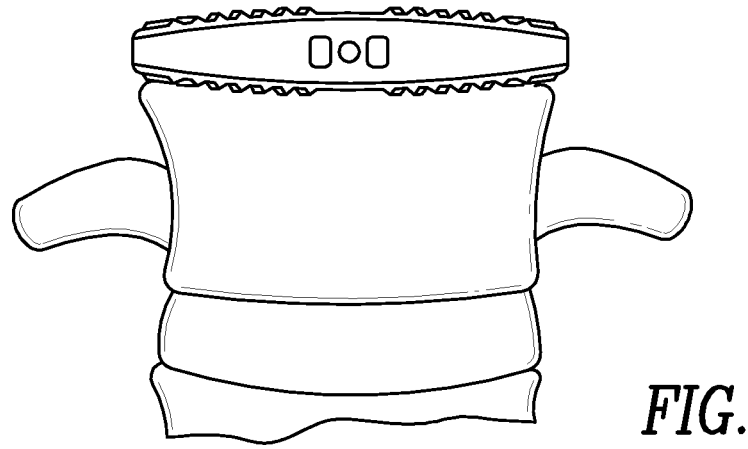
Figure 70C:
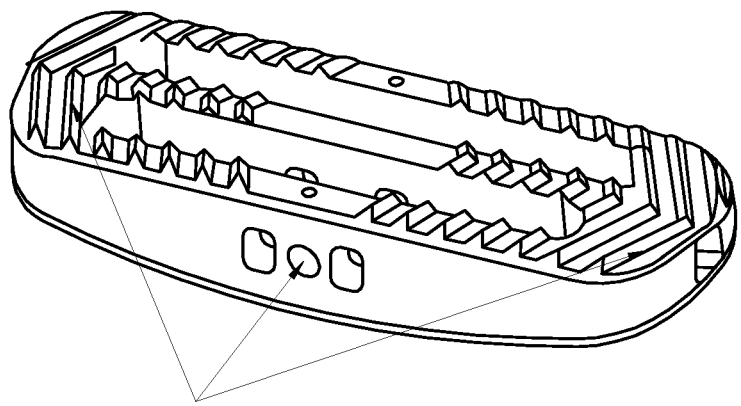

FIGS. 70a-70c illustrate an exemplary implant, according to some embodiments of the present invention. An exemplary design of an implant is illustrated in a U.S. provisional application No. 61/192,210 to Guyer et al., filed Sep. 16, 2008, entitled "Interbody Spacer", the disclosure of which is incorporate herein by reference in its entirety. In some embodiments, the implant includes a curvilinear design, as shown in FIGS. 70a and 70c. The implant can be configured to include a quad snow plow design that restricts movement in four directions. Additionally, the implant can include large openings for packing bone and a tapered leading edge for self-distract purposes. Further, in some embodiments, the implant includes holes in center divide for vascularization purposes. The implant can be slid posterior and include a wall to avoid a DBM leak.

FIGS. 71a-c illustrate an exemplary implant having a fluoroscopic marker, according to some embodiments of the present invention.

FIGS. 72a-c illustrate another exemplary implant having a fluoroscopic marker, according to some embodiments of the present invention.

FIGS. 73-98 illustrate an exemplary system for curvilinear access to lateral spine of a patient, according to some embodiments of the present invention. In some embodiments, the portal 7300 can be delivered to the patient's lateral spine 7301 in the closed configuration over one or more dilators and then can be opened in-situ after the dilators are removed to provide direct visualization to the surgical site by opening a movable top. As shown in FIG. 73, the system 7300 includes a portal 7302 through which various surgical instruments can be delivered to the lateral spine 7301 and optionally an implant 7303. In some embodiments, the portal 7302 can be supported using a holding arm assembly.

Figure 75:
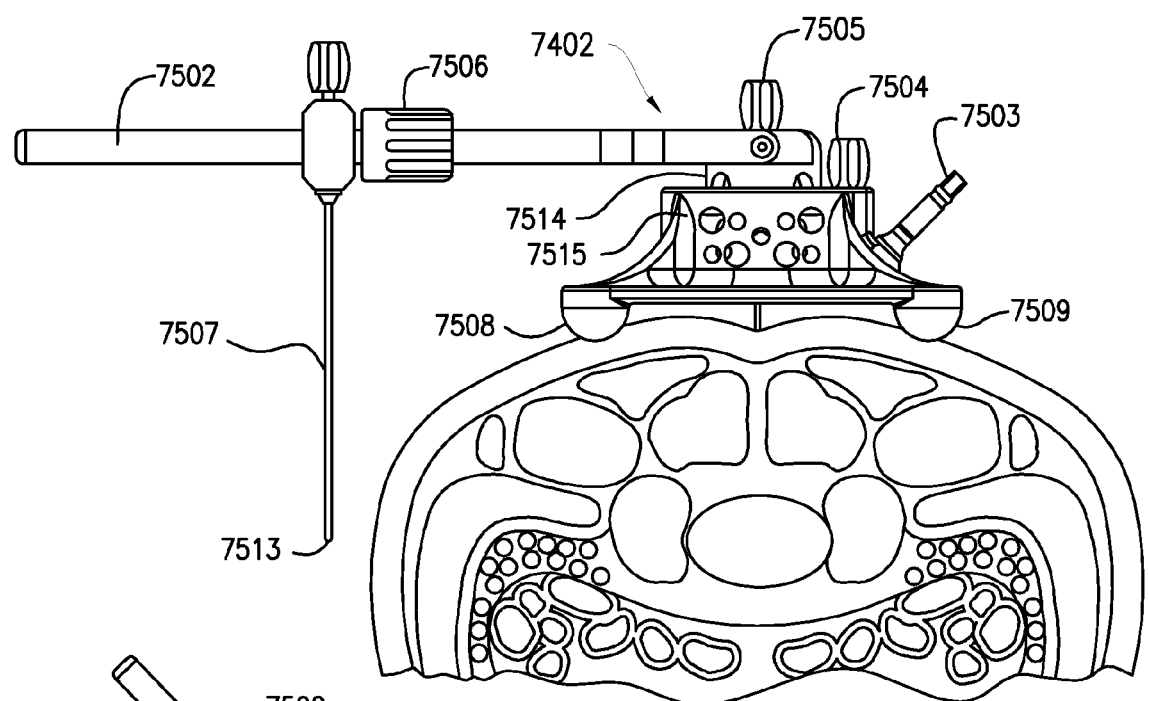
FIG. 75 illustrates the calibrated introducer and a cross-sectional view of the operative space, according to some embodiments of the present invention.
Figure 76:
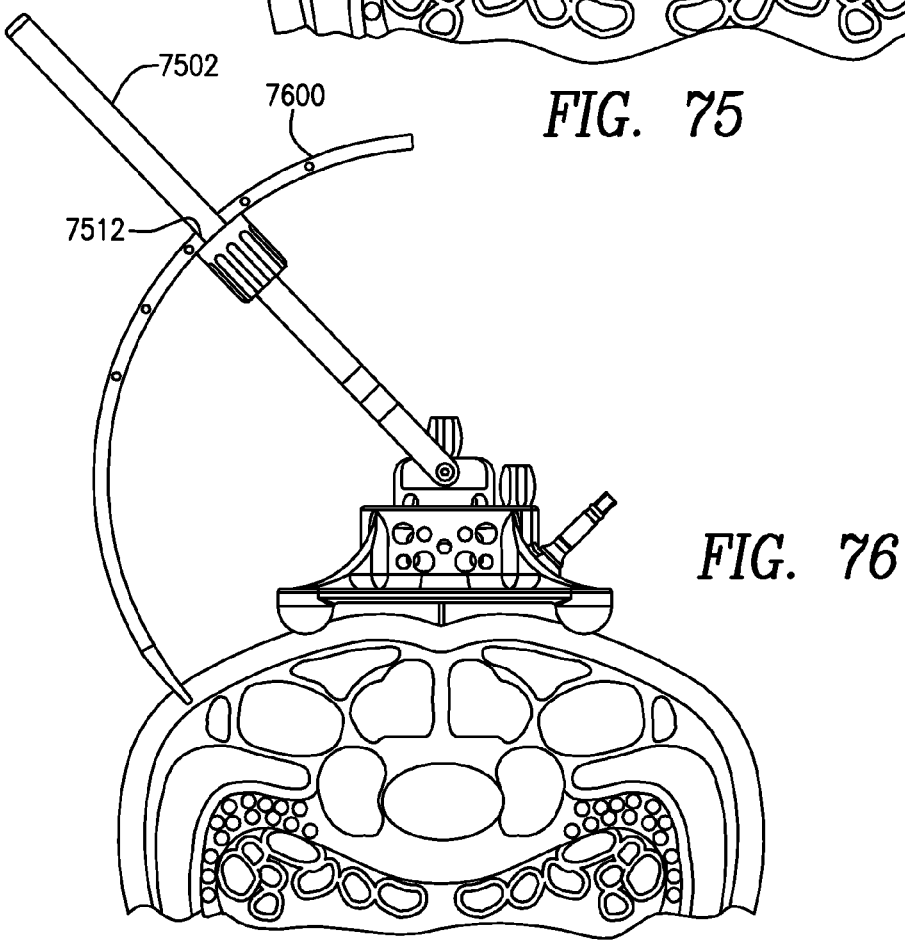
FIG. 76 illustrates the calibrated introducer loaded with a dilator and a cross-sectional view of the operative space, according to some embodiments of the present invention.
Figure 77:
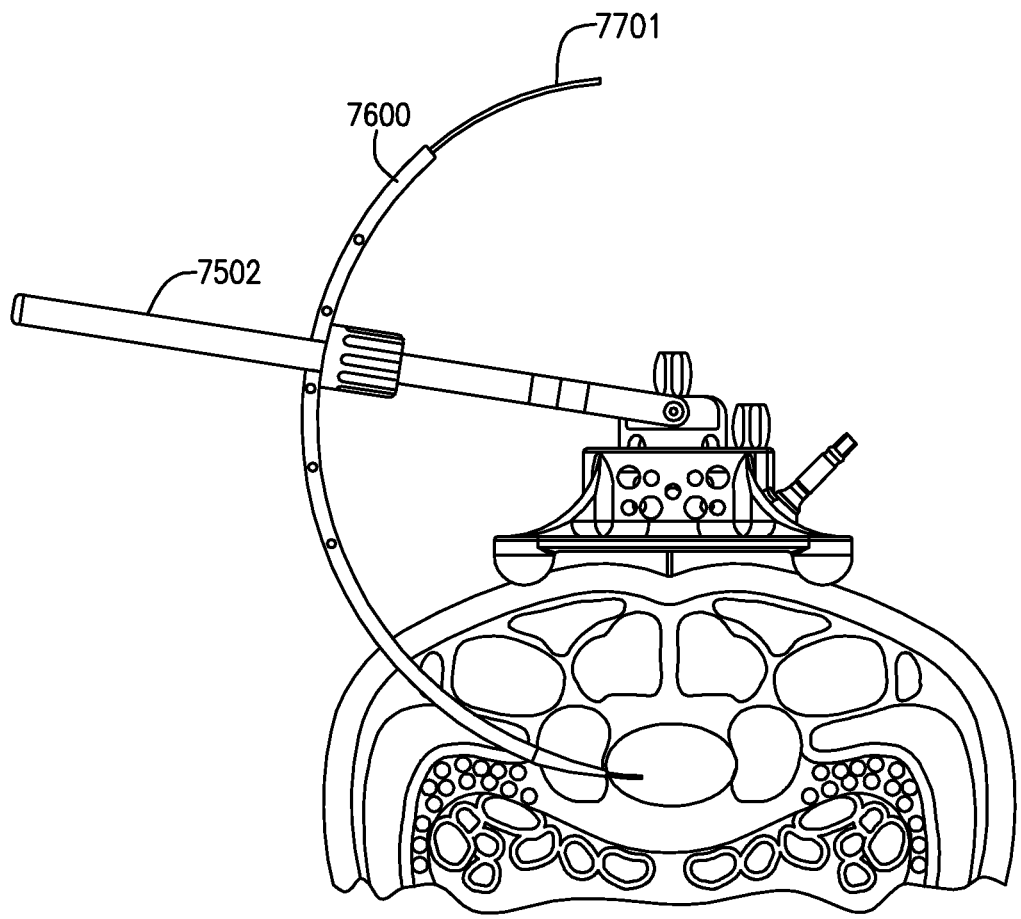
FIG. 77 illustrates the calibrated introducer loaded with a dilator and a cross-sectional view of the operative space, according to some embodiments of the present invention.
Figure 78:
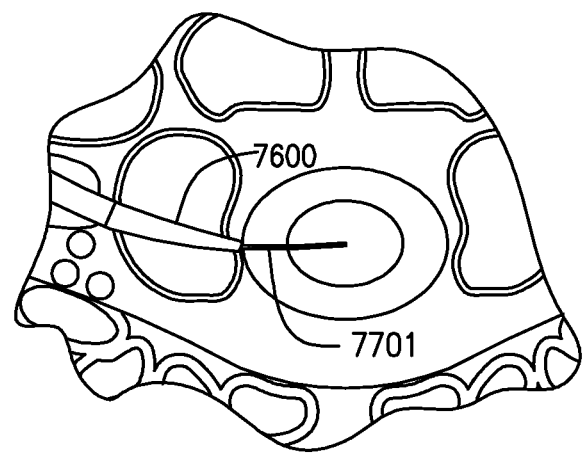
FIG. 78 is a detailed sectional view of the dilator shown in FIGS. 76 and 77 and a guidewire entering the intervertebral space, according to some embodiments of the present invention.
Figure 79:
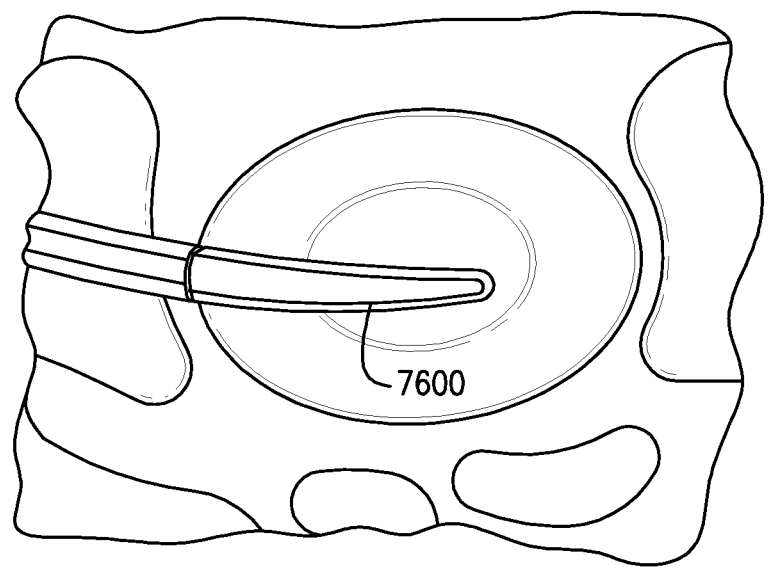
FIG. 79 is detailed sectional view of the dilator shown in FIGS. 76 and 77 entering the intervertebral space, according to some embodiments of the present invention.

FIG. 74-77 show one embodiment of using a locating pin 7400 and calibrated introducer 7402. FIG. 74 illustrates an exemplary locating pin 7400 which is placed at the desired vertebral level, for example, directly posterior to the center of the disc space. The locating pin 7400 is utilized to properly seat the calibrated introducer 7402, which may be attached to a fixation arm 7401. As shown in FIG. 75 (and similar targeting device shown in FIGS. 56c-56h), the calibrated introducer 7402 includes a central channel 7501 (which can be seen in more detail on the bottom of FIG. 56d), a swing arm 7502, fixation arm connector 7503, two securing knobs 7504, 7505, an adjusting sleeve 7506, a vertical pin 7507, stabilizing feet 7508, 7509, 7510, 7511 (not pictured), attachment channel 7512, inner platform 7514 and outer platform 7515. The calibrated introducer 7402 is placed over the locating pin 7400 though the central channel 7501 of the calibrated introducer 7402. The vertical pin 7507 is slid onto the swing arm 7502 until it is approximately 1 cm away from the patient's skin. If necessary, securing knobs 7504 and 7505 allow the surgeon to properly line up the distal tip 7513 of the vertical pin 7507 with the center of the vertebral body, such as shown in FIG. 76. The angular adjusting knob 7504 allows the surgeon to adjust the angular relationship of the vertical pin 7507 with respect to the patient's vertebrae. The height adjusting knob 7505 raises and lowers the inner platform 7514 with respect to the outer platform 7515, which allows the surgeon to adjust the height of the vertical pin with respect to the patient's vertebrae. The inner platform 7514 also rotates 360 degrees within the outer platform 7515. FIGS. 77 and 78 illustrate additional views of the calibrated introducer 7402. Once the vertical pin 7507 is lined up with the center of the vertebral body, the adjusting sleeve 7506 is locked into place and the vertical pin 7507 is removed from the swing arm 7502.

The calibrated introducer 7402 is used, as described above, to properly locate the incision point. The calibrated introducer 7402 utilizes external reference points of a patient's body to determine the proper incision point, allowing for varying patient size. As shown in FIG. 76, dilator A 7600 is attached to the swing arm 7502 by threading dilator A 7600 through attachment channel 7512 and locked in place. The swing arm 7502 is then rotated until dilator A 7600 contacts the patient's skin; this is the incision point. Once the incision point is located, the surgeon makes the incision and finger palpates a surgical channel through the tissue. The surgeon then rotates swing arm 7502, advancing dilator A 7600 into the surgical incision until dilator A 7600 reaches the annular wall of the vertebrae, shown in FIG. 77.

As shown in FIGS. 77-78, a guidewire 7701 is delivered through a cannula of dilator A 7600 and inserted into the vertebral disc. Illustrated by FIG. 79, dilator A 7600 is then inserted into the vertebral body. An impactor or mallet of some type may be used to force the dilator 7600 and/or the guidewire 7701 into the vertebral body.

Figure 80:
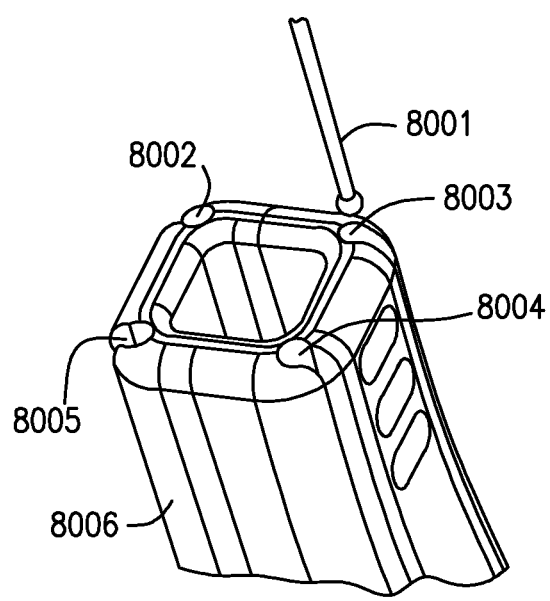
FIG. 80 illustrates an exemplary neuromonitoring probe and dilator configuration, according to some embodiments of the present invention.

As shown in FIG. 80, optionally, a neuromonitoring probe 8001 may be inserted into one of channels 8002, 8003, 8004 or 8005 of dilator B 8006, until the probe contacts a stop at the end of the dilator tip. These channels would be geometrically shaped to adapt a probe/lead which would be inserted and slid down one or more of the channels of the dilator. In other embodiments, a neuromonitoring probe may be used with the guidewire, any of the dilators, or the portal.

FIG. 81 shows dilator B 8006 placed over dilator A 7600. Dilator B 8006 is advanced into the incision until it abuts the annular wall of the vertebral body. If it was used, the neuromonitoring probe 8001 is now removed from dilator B 8006. FIG. 81 also illustrates the dilator impactor tool 8101. The impactor 8101 provides surface area and may be used to impact any one of the dilators from lateral to medial towards intervertebral space.

Figure 83:
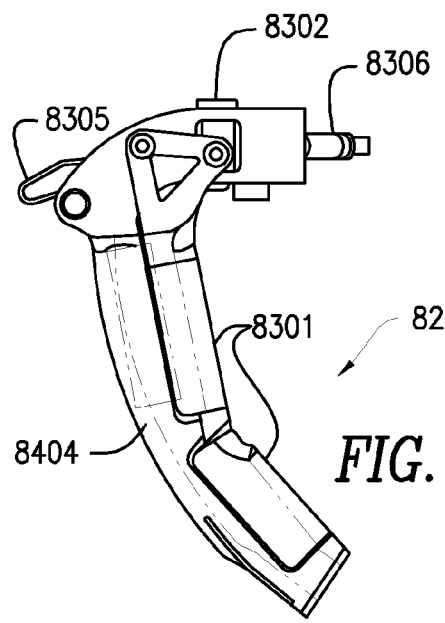
FIG. 83 illustrates an exemplary curved portal in the closed configuration, according to some embodiments of the present invention.
Figure 84:
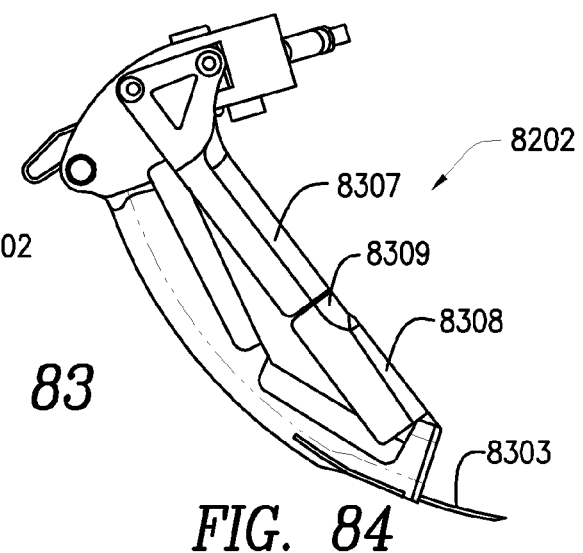
FIG. 84 illustrates an exemplary curved portal in the open configuration, according to some embodiments of the present invention.

Any number of additional dilators may be used. In the embodiment shown in FIG. 82, insert dilator C 8201 is placed over dilator 8006, and the curved portal 8202 is placed over dilator C 8201. Once the curved portal 8202 is inserted, all dilators may be removed. As illustrated by FIGS. 83-85, the curved portal 8202 includes a moveable top 8301, lid extension screw 8302, anterior awl 8303, portal slide 8304, impacting surface 8305 and fixation arm attachment 8306. The moveable top 8301 is coupled to the lid extension screw 8302 such that rotation of the lid extension screw 8302 opens or closes the movable top 8301 with respect to the portal slide. The moveable top 8301 comprises a proximal portion 8307, a distal portion 8308, and a hinge 8309. In this particular embodiment, the proximal and distal portions 8307, 8308 are moved for expansion of the working portal, however, one skilled in the art would understand that other means of expansion are possible by means such as a roll top or use of a malleable material.

Figure 85A:
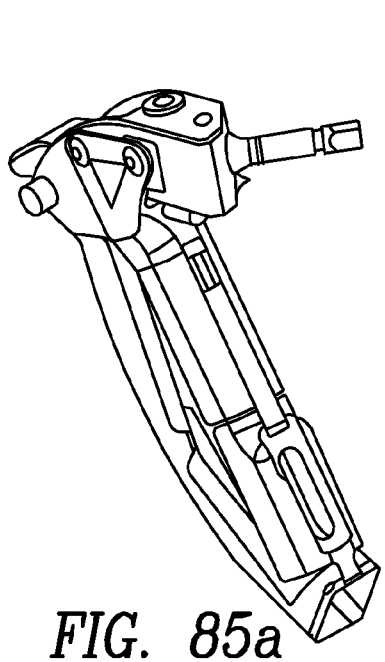
FIGS. 85a-85b illustrates an isometric view and an exploded view, respectively, of an exemplary curved portal, as shown in FIG. 85, according to some embodiments of the present invention.
Figure 85B:
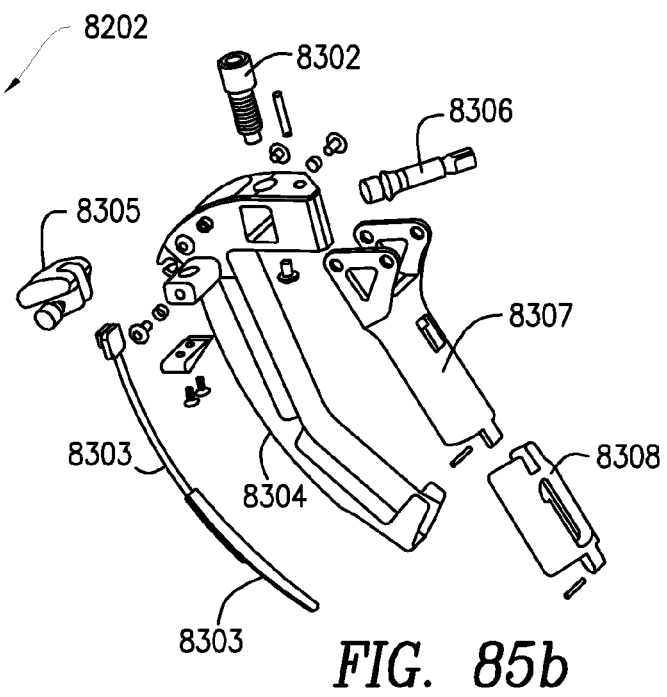

FIG. 83 shows the portal 8202 with the movable top 8301 in a closed position, where the movable top 8301 blocks direct visualization between the proximal end and the distal end of the portal. This closed position of the portal 8202 is used primarily during insertion and removal of the portal 8202 from the patient. FIG. 84 shows the portal 8202 the movable top 8301 in a fully open position, where the movable top 8301 allows direct visualization between the proximal end and the distal end of the portal. FIG. 85a is an isometric view of the portal 8202. FIG. 85b is an exploded view of the portal 8202. In the embodiment shown in FIG. 86, the top 8301 may expanded or opened by rotating an expansion screw 8302 using the toeing wrench 8601 or twisting by hand with a knob (not shown). In other embodiments, the top may be opened with an actuation screw or screw actuator coupled to the top. After the top 8301 is expanded and the portal 8202 has been opened, either partially or completely per the surgeon's discretion, the surgeon distally extends the anterior awl 8310 along the slide 8311 of the curved portal 8202. The anterior awl 8310 is used to extend the anterior tab 8312 into the annulus of the vertebral body which aids in docking the portal 8202 to the vertebral body.

The moveable top 8301 and portal slide 8304 may be made from metal, plastic, polymer, polyetheretherketone ("PEEK") or other suitable material. The impacting surface 8305 and fixation arm attachment 8306 may also be made from metal, plastic, polymer, or other suitable material.

Figure 89:
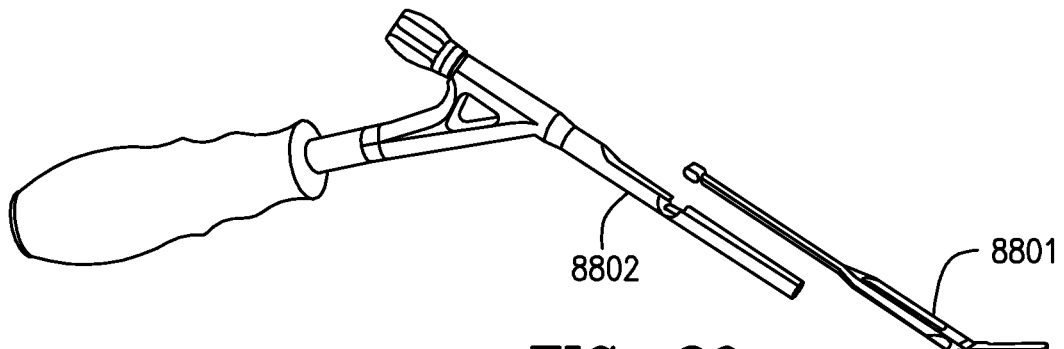
FIG. 89 is an exploded view of a posterior tab inserter coupled with the posterior tab of FIG. 88, according to some embodiments of the present invention.
Figure 90:
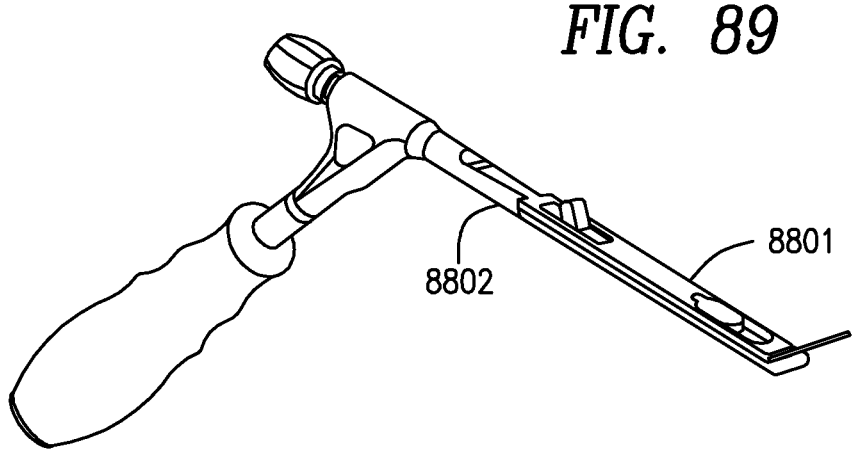
FIG. 90 is a posterior tab inserter coupled with the posterior tab of FIG. 88, according to some embodiments of the present invention.
Figure 91:
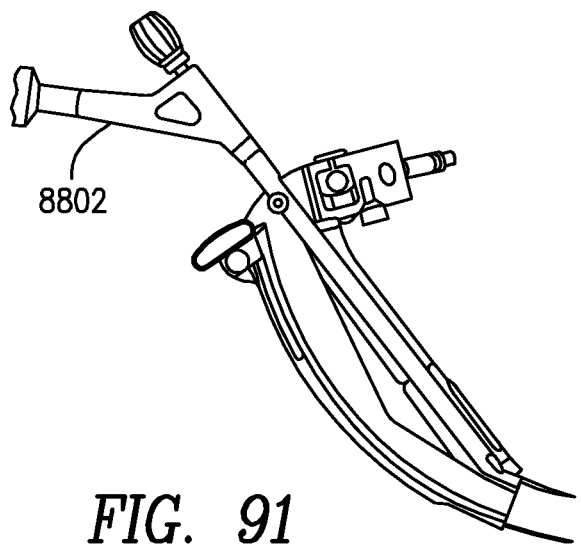
FIG. 91 shows a posterior tab inserter coupled with the posterior tab of FIG. 88 as inserted into the curved portal, according to some embodiments of the present invention.
Figure 92:
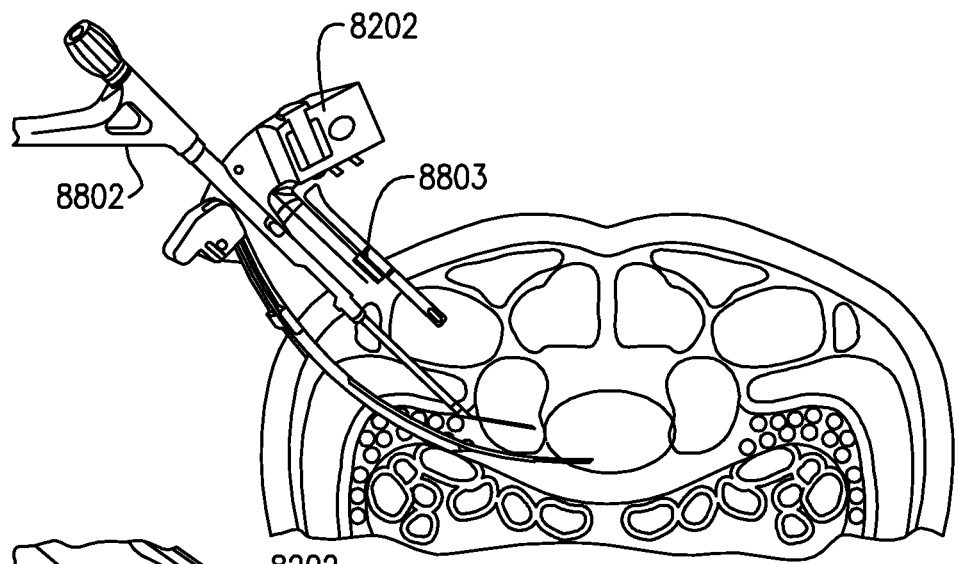
FIG. 92 shows cross-sectional view of the operative space a posterior tab inserter coupled with the posterior tab of FIG. 88 is inserted into the curved portal, according to some embodiments of the present invention.
Figure 93:
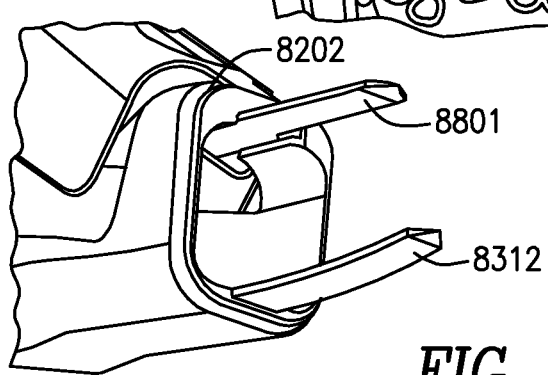
FIG. 93 is a detailed view of the posterior tab and the anterior awl attached to the proximal end of the curved portal.

FIGS. 88-93 show embodiments of using a posterior tang or posterior tab 8801 with portal 8202. The surgeon next inserts the posterior tang or posterior tab 8801, shown in FIG. 88, into the portal 8202. The posterior tang or posterior tab 8801 is used to sweep the portal clear of tissue and hold back nerve roots and tissue. The posterior tang or posterior tab 8801 is inserted into the portal with the tab inserter tool 8802, as shown in FIGS. 89 and 90. The posterior tang or posterior tab 8801 is attached to the tab inserter tool 8802 as shown in FIG. 90, and inserted into the portal 8202, as shown in FIG. 91. The posterior tang or posterior tab 8801 is attached to the portal 8202 with at least one connection point 8803, as shown in FIG. 92, to insure that it slides down the curved portal 8202 in a controlled manner. The posterior tang or posterior tab 8801 may feature a positive spring loaded catch which interfaces with a cutout in portal lid. As shown in FIG. 93, the portal now has two tabs, anterior tab 8312 and posterior tang or posterior tab 8801, protruding from the distal end of the portal 8202.

Figure 94:
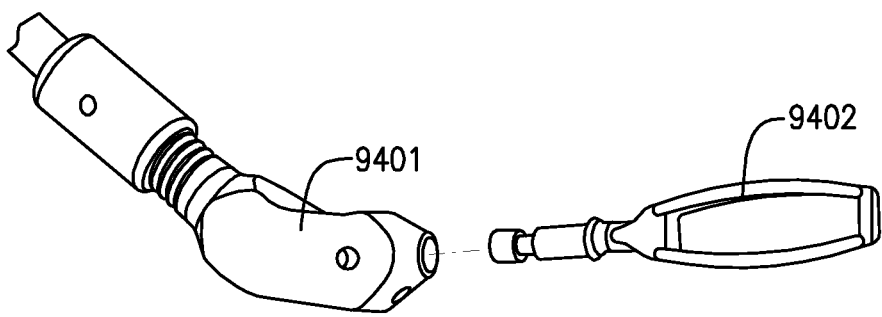
FIG. 94 is a detailed view of the rotating actuator and shaver blades, according to some embodiments of the present invention.
Figure 95:
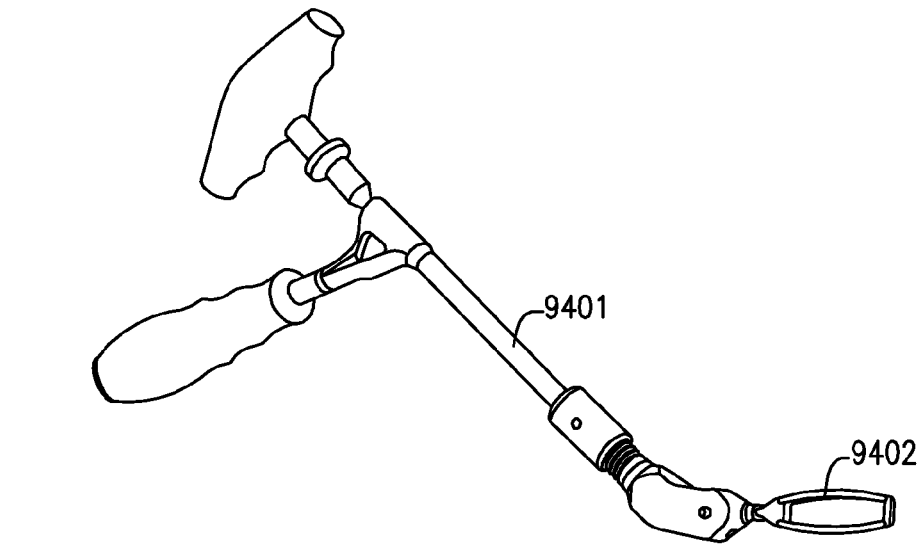
FIG. 95 is a view of the rotating actuator and shaver blades.
Figure 96:
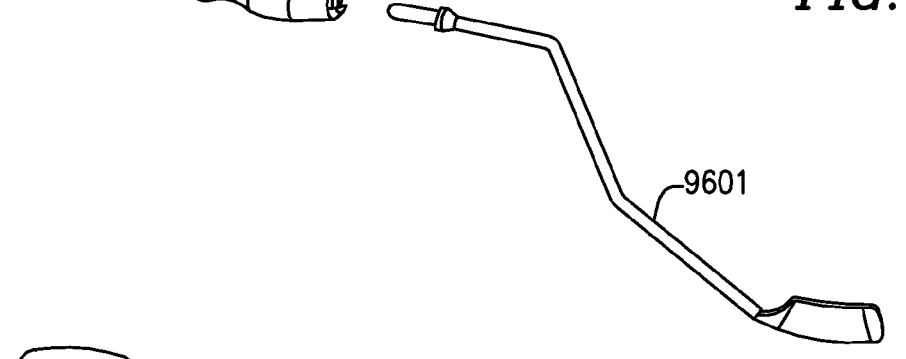
FIG. 96 illustrates an exemplary implant trial, according to some embodiments of the present invention.
Figure 97:
FIG. 97 illustrates exemplary implant trial usage with respect to the vertebral disc, according to some embodiments of the present invention.

Once the working portal of portal 8202 is in the open configuration, the surgeon may now perform the desired procedure which may include the implantation of an implant, such as those discussed above with reference to FIGS. 69c-72c, or other suitable implants. In the performance of the desire procedure, the surgeon may choose to use the tools illustrated in FIGS. 94-98. FIGS. 94 and 95 illustrate an exemplary rotating actuator 9401 and shaver blade attachment 9402. FIG. 96 illustrates an exemplary implant trial 9601, according to some embodiments of the present invention. FIG. 97 illustrates exemplary implant trial usage with respect to the vertebral disc, according to some embodiments of the present invention. FIG. 98 illustrates the implant 9801 and implant inserter 9802 with respect to the vertebral body, according to some embodiments of the present invention.

In some embodiments, the guided lumbar interbody fusion system can also implement tools such as a curved wedge distracter, a self-distracting implant inserter, a curved probe, a curved tamp, as well as other instruments and tools.

In some embodiments, where the present invention's device and instrumentation are used for implant delivery, the implants may include, but are not limited to: bone screws, plates, interbody devices, artificial discs, or any other implants. Further, the present invention's device and methodology can be used in any number of surgical procedures, including nucleus replacement, total disc replacement, interbody fusion, discectomy, neural decompression, implant delivery (whether for fixation purposes and/or stabilization), or any other procedure.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A curvilinear access device having an expandable working portal comprising:
   a slide having a channel with an open top; and
   a movable top sized to cover the open top of the channel forming the expandable working portal with a proximal end and a distal end;
   wherein the movable top is movable between a closed position and an open position, wherein in the closed position the movable top blocks direct visualization between the proximal end and the distal end of the expandable working portal, and in the open position the movement of the movable top results in direct visualization from the proximal end to the distal end of the expandable working portal;
   wherein the movable top includes a proximal end and distal end, the proximal end being pivotally secured near the proximal end of the working portal and the distal end being pivotally secured near the distal end of the working portal.

2. The device of claim 1, wherein the movable top is positioned proximate the open top channel in the closed position and portions of the movable top are positioned away from the open top channel in the open position.

3. The device of claim 1, further comprising opening means coupled to the movable top, the opening means configured to move the movable top between the closed and open positions.

4. The device of claim 3, wherein the opening means is selected from a group consisting of an actuation screw, screw actuator, expansion screw, a handle and push buttons.

5. The device of claim 1, wherein the movable top is in the closed position during insertion of the device to a surgical site.

6. The device of claim 1, wherein the channel is substantially curved.

7. The device of claim 1, wherein the device is used to access a surgical site, the device having a distal end configured to be disposed at the surgical site and a proximal end disposed away from the surgical site, and wherein the open position allows direct visualization of the surgical site through the expandable working portal.

8. The device of claim 1, wherein the channel includes a back portion with side portions and an open top.

9. The device of claim 1, wherein the expandable working portal has a width in a range of 5 mm to 30 mm and a range of heights from 5 mm to 30 mm.

10. The device of claim 1, wherein the expandable working portal has a cross-section selected from the group consisting of: square, rectangular, oval, polygonal.

11. The device of claim 1, wherein the device is used in a surgical procedure selected from a group consisting of nucleus replacement, total disc replacement, interbody fusion, discectomy, neural decompression, implant delivery and any other surgical procedure.

12. The device of claim 1, further comprising an anterior awl having an anterior tang slidaby coupled to the slide, the anterior tab configured to extend distally proximate a lower portion of the expandable working portal.

13. The device of claim 12, further comprising a posterior tab slidaby coupled to the slide or top and configured to extend distally proximate an upper portion of the expandable working portal.

14. The device of claim 1, further comprising a post configured to engage a holding arm assembly.

15. The device of claim 1, wherein the slide and/or top are made from metal, plastic, polymer, or other suitable material.

16. The device of claim 1, wherein the slide and/or top are made from polyetheretherketone ("PEEK").

17. A curvilinear access device having an expandable working portal comprising:
   a slide having a channel with an open top; and
   a movable top sized to cover the open top of the channel forming the expandable working portal with a proximal end and a distal end;
   wherein the movable top is movable between a closed position and an open position, wherein in the closed position the movable top blocks direct visualization between the proximal end and the distal end of the expandable working portal, and in the open position the movement of the movable top results in direct visualization from the proximal end to the distal end of the expandable working portal;
   wherein the expandable working portal is configured to allow advancement of at least one surgical tool and/or at least one implant toward a surgical site in the open position;
   wherein the movable top comprises a proximal portion pivotally secured to a distal portion.

18. A device for performing a procedure on the spine of a patient, comprising:
   a working portal configured to be advanced toward a surgical site of the spine of the patient including
     a distal end and a proximal end;
     a working portal housing having an interior channel with an open top disposed between the distal end and the proximal end;
     a movable top configured to be secured to the working portal housing;
     the distal end is configured to be disposed at the surgical site and the proximal end is disposed away from the surgical site;
     the housing has a curved shape defined between the proximal end and the distal end;
     the movable top is configured to cover the open top of the interior channel of the working portal housing;

the working channel is configured to allow advancement of at least one surgical tool and/or at least one implant toward the surgical site; and an anterior awl configured to be advanced toward the surgical site along the working portal housing and further configured to anchor the working portal at the surgical site.

19. The device of claim 18, wherein the proximal end is disposed at an angle with respect to the distal end.

20. The device of claim 18, wherein the movable top includes a proximal portion and distal portion; the proximal portion is pivotally secured to the proximal end of the working portal housing and the distal portion is pivotally secured to the distal end of the working portal housing; and the proximal portion is pivotally secured to the distal portion.

21. The device of claim 18, wherein the working portal housing includes at least one actuation means configured to open and close the movable top.

22. The device of claim 18, wherein the surgical procedure is selected from a group consisting of: nucleus replacement, total disc replacement, interbody fusion, discectomy, neural decompression, implant delivery and any other surgical procedure.

* * * * *